United States Patent [19]

Flaugh et al.

[11] Patent Number: 5,814,653

[45] Date of Patent: Sep. 29, 1998

[54] PHARMACEUTICAL METHOD USING 6-SUBSTITUTED-1, 2, 3, 4-TETRAHYDRO-9H-CARBAZOLES AND 7-SUBSTITUTED-10H-CYCLOHEPTA (7, 6-B) INDOLES

[75] Inventors: Michael Edward Flaugh; Anton Daniel Kiefer, Jr.; Clint Duane Walker, all of Indianapolis; Yao-Chang Xu, Fishers, all of Ind.

[73] Assignee: Eli Lilly and Company, Indianapolis, Ind.

[21] Appl. No.: 992,320

[22] Filed: Dec. 17, 1997

Related U.S. Application Data

[62] Division of Ser. No. 671,465, Jun. 27, 1996, Pat. No. 5,708,187.

[51] Int. Cl.$^6$ ...................................................... A61K 31/40
[52] U.S. Cl. .............................................................. 514/411
[58] Field of Search ............................................... 514/411

[56] References Cited

U.S. PATENT DOCUMENTS

| | | |
|---|---|---|
| 3,642,816 | 2/1972 | Mooradian . |
| 3,959,309 | 5/1976 | Mooradian . |
| 4,775,680 | 10/1988 | Gillard et al. . |
| 4,827,032 | 5/1989 | Böshagen et al. . |
| 4,988,820 | 1/1991 | Böshagen et al. . |
| 5,039,670 | 8/1991 | Böshagen et al. . |
| 5,223,517 | 6/1993 | Müller et al. . |
| 5,464,864 | 11/1995 | King et al. . |

FOREIGN PATENT DOCUMENTS

WO 93/00086   1/1973   WIPO .

OTHER PUBLICATIONS

J. Med. Chem., Frank D. King, et al., 36, 1993, pp. 1918–1919.

Prog. Neuro–Psychopharmacol. & Biol. Psychiat, Paul L. Wood, et al., "Ciclindole and Flucindole: Novel Tetrahydrocarbazolamine Neuroleptics", vol. 8, 1984, pp. 773–777.

Journal of Neurochemistry, Eitan Friedman, et al., "Effects of Conformationally Restrained Analogues of Serotonin on Its Updake and Binding in Rat Brain", 36(3), 1981, pp. 931–937.

Journal of Neurochemistry, E. Meller, et al., "Tetrahydro–β–Carbolines: Specific Inhibitors of Type A Monoamine Oxidase in Rat Brain", vol. 28, 1977, pp. 995–1000.

Journal of Medicinal Chemistry, A. Mooradian, et al., "Communications to the Editor: Hydroxylated 2,3,4, 9–Tetrahycro–1H–Carbazol–3–Amines. A New Class of Experimental Cardiotonic Drugs", 1975, vol. 18, No. 6, pp. 640–641.

Journal of Medicinal Chemistry, A. Mooradian, et al., "3–Aminotetrahydrocarbazoles as a New Series of Central Nervous System Agents", 1977, vol. 20, No. 4, pp. 487–492.

J. Chem. Soc. (C), Org., "Synthesis of 3–Amino–1,2,3, 4–Tetrahydro–6–Hydroxycarbazole, Analogue of 5–Hydroxytryptamine", G. E. A. Coombes, et al., 1970, pp. 325–326.

*Primary Examiner*—Robert W. Ramsuer
*Attorney, Agent, or Firm*—Robert D. Titus; David E. Boone

[57] ABSTRACT

This invention provides novel 6-substituted-1,2,3,4-tetrahydro-9H-carbazoles and 7-substituted-10H-cyclohepta [7,6-b]indoles. These compounds are 5-HT$_{1F}$ agonists which are useful for the treatment of migraine and associated disorders.

3 Claims, No Drawings

PHARMACEUTICAL METHOD USING 6-SUBSTITUTED-1, 2, 3, 4-TETRAHYDRO-9H-CARBAZOLES AND 7-SUBSTITUTED-10H-CYCLOHEPTA (7, 6-B) INDOLES

This application is a divisional of application Ser. No. 08/671,465 filed Jun. 27, 1996, now U.S. Pat. No. 5,708,187.

BACKGROUND OF THE INVENTION

Theories regarding the pathophysiology of migraine have been dominated since 1938 by the work of Graham and Wolff (*Arch. Neurol. Psychiatry*, 39, 737–63 (1938)). They proposed that the cause of migraine headache was vasodilatation of extracranial vessels. This view was supported by knowledge that ergot alkaloids and sumatriptan, a hydrophilic 5-$HT_1$ agonist which does not cross the blood-brain barrier, contract cephalic vascular smooth muscle and are effective in the treatment of migraine. (Humphrey, et al., *Ann. NY Acad. Sci.*, 600, 587–600 (1990)). Recent work by Moskowitz has shown, however, that the occurrence of migraine headaches is independent of changes in vessel diameter (*Cephalalgia*, 12, 5–7, (1992)).

Moskowitz has proposed that currently unknown triggers for pain stimulate trigeminal ganglia which innervate vasculature within the cephalic tissue, giving rise to release of vasoactive neuropeptides from axons on the vasculature. These released neuropeptides then activate a series of events, a consequence of which is pain. This neurogenic inflammation is blocked by sumatriptan and ergot alkaloids by mechanisms involving 5-HT receptors, believed to be closely related to the 5-$HT_{1D}$ subtype, located on the trigeminovascular fibers (*Neurology*, 43(suppl. 3), S16–S20 (1993)).

Serotonin (5-HT) exhibits diverse physiological activity mediated by at least four receptor classes, the most heterogeneous of which appears to be 5-$HT_1$. A human gene which expresses a fifth 5-$HT_1$ subtype, named 5-$HT_{1F}$, was isolated by Kao and coworkers (*Proc. Natl. Acad. Sci. USA*, 90, 408–412 (1993)). This 5-$HT_{1F}$ receptor exhibits a pharmacological profile distinct from any serotonergic receptor yet described. The high affinity of sumatriptan at this subtype, $K_i$=23 nM, suggests a role of the 5-$HT_{1F}$ receptor in migraine.

This invention provides novel 5-$HT_{1F}$ agonists which inhibit peptide extravasation due to stimulation of the trigeminal ganglia, and are therefore useful for the treatment of migraine and associated disorders.

SUMMARY OF THE INVENTION

The present invention provides novel 6-substituted-1,2,3,4-tetrahydro-9H-carbazoles and 7-substituted-10H-cyclohepta[7,6-b]indoles of Formula I:

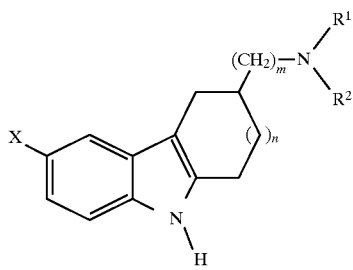

wherein:

$R^1$ and $R^2$ are independently hydrogen, $C_1$–$C_4$ alkyl, or —$CH_2CH_2$-Aryl where Aryl is phenyl, phenyl monosubstituted with halo, or 1-($C_1$–$C_6$ alkyl)pyrazol-4-yl;

X is —OH, —NHC(O)$R^3$, —NHC(Y)NH$R^4$, —NHC(O)O$R^5$, —C(O)$R^6$ or —NHSO$_2R^7$;

$R^3$ is $C_1$–$C_6$ alkyl, $C_2$–$C_6$ alkenyl, $C_3$–$C_8$ cycloalkyl, phenyl, substituted phenyl, naphthyl, ($C_1$–$C_4$ alkylene) phenyl, thienylmethyl, or a heterocycle;

$R^4$ is $C_1$–$C_6$ alkyl, phenyl, or phenyl disubstituted with halo;

$R^5$ is $C_1$–$C_6$ alkyl, $C_2$–$C_6$ alkenyl, benzyl or phenyl monosubstituted with halo;

$R^6$ is $C_1$–$C_6$ alkyl, phenyl, or phenyl monosubstituted with halo or $C_1$–$C_4$ alkoxy;

$R^7$ is dimethylamino, phenyl or phenyl monosubstituted with halo or $C_1$–$C_4$ alkyl;

m is 0 or 1;

n is 1 or 2; and

Y is S or O; and pharmaceutically acceptable salts and hydrates thereof, providing:

X is not —OH when m is 0, n is 1, and $R^1$ and $R^2$ are independently hydrogen or $C_1$–$C_6$ alkyl; and $R^3$ is not $C_1$–$C_6$ alkyl when m is 0, n is 1, and $R^1$ and $R^2$ are independently hydrogen or $C_1$–$C_6$ alkyl.

A further embodiment of this invention is a method for increasing activation of the 5-$HT_{1F}$ receptor by administering a compound of Formula II:

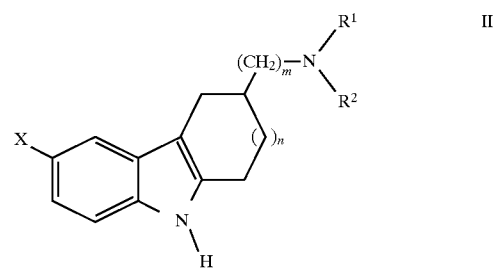

wherein:

$R^1$ and $R^2$ are independently hydrogen, $C_1$–$C_4$ alkyl, or —$CH_2CH_2$-Aryl where Aryl is phenyl, phenyl monosubstituted with halo, or 1-($C_1$–$C_6$ alkyl)pyrazol-4-yl;

X is —OH, —NHC(O)$R^3$, —NHC(Y)NH$R^4$, —NHC(O)O$R^5$, —C(O)$R^6$, —NHSO$_2R^7$;

$R^3$ is $C_1$–$C_6$ alkyl, $C_2$–$C_6$ alkenyl, $C_3$–$C_8$ cycloalkyl, phenyl, substituted phenyl, naphthyl, ($C_1$–$C_4$ alkylene) phenyl, thienylmethyl, or a heterocycle;

$R^4$ is $C_1$–$C_6$ alkyl, phenyl, or phenyl disubstituted with halo;

$R^5$ is $C_1$–$C_6$ alkyl, $C_2$–$C_6$ alkenyl, benzyl or phenyl monosubstituted with halo;

$R^6$ is $C_1$–$C_6$ alkyl, phenyl, or phenyl monosubstituted with halo or $C_1$–$C_4$ alkoxy;

$R^7$ is dimethylamino, phenyl or phenyl monosubstituted with halo or $C_1$–$C_4$ alkyl;

m is 0 or 1;

n is 1 or 2; and

Y is S or O; and pharmaceutically acceptable salts and hydrates thereof.

Activation of the 5-$HT_{1F}$ receptor provides a method for treating a variety of disorders which have been linked to decreased neurotransmission of serotonin in mammals. Included among these disorders are depression, migraine pain, bulimia, premenstrual syndrome or late luteal phase syndrome, alcoholism, tobacco abuse, panic disorder, anxiety, post-traumatic syndrome, memory loss, dementia of aging, social phobia, attention deficit hyperactivity disorder, disruptive behavior disorders, impulse control disorders, borderline personality disorder, obsessive compulsive disorder, chronic fatigue syndrome, premature ejaculation, erectile difficulty, anorexia nervosa, disorders of sleep, autism, mutism or trichotillomania. Any of these methods employ a compound of Formula II.

DETAILED DESCRIPTION OF THE INVENTION

The general chemical terms used in the formulae above have their usual meanings. For example, the terms "alkyl, alkoxy and alkylthio" include such groups as methyl, ethyl, n-propyl, isopropyl, n-butyl, isobutyl, sec-butyl, tert-butyl, pentyl, 2-pentyl-, 3-pentyl-, neopentyl, hexyl, heptyl, and the like. The term "alkenyl" includes allyl, 1-buten-4-yl, 2-methyl-1-buten-4-yl, 2-buten-4-yl, 1-penten-5-yl, 4-methyl-2-penten-5-yl, 2-penten-5-yl, 3-penten-5-yl, 1-hexen-6-yl, 2-hexen-6-yl, 3-hexen-6-yl, 4-hexen-6-yl and the like. The term "acyl" includes formyl, acetyl, propanoyl, butanoyl, and 2-methylpropanoyl. The term "cycloalkyl" includes such groups as cyclopropyl, cyclobutyl, cyclopentyl, cyclohexyl, cycloheptyl and cyclooctyl. The term "($C_1$–$C_4$ alkylene)phenyl" includes such groups as benzyl, phenethyl, 1-phenyl-2-methylpropyl, phenpropyl and phenbutyl. The term "($C_1$–$C_4$ alkyl)sulfonyl" includes methanesulfonyl, ethanesulfonyl, propanesulfonyl, isopropanesulfonyl, butanesulfonyl and the like. The term "halo" includes fluoro, chloro, bromo and iodo.

The term "substituted phenyl" is taken to mean a phenyl group substituted with one substituent selected from the group consisting of halo, $C_1$–$C_4$ alkyl, $C_1$–$C_8$ alkoxy, $C_1$–$C_4$ alkylthio, nitro, cyano, di($C_1$–$C_4$ alkyl)amino, trifluoromethyl, trifluoromethoxy, phenyl, $C_1$–$C_4$ acyl, benzoyl or ($C_1$–$C_4$ alkyl)sulfonyl, or two to three substituents independently selected from the group consisting of halo, nitro, $C_1$–$C_4$ alkyl, or $C_1$–$C_4$ alkoxy.

The term "heterocycle" is taken to mean furyl, thienyl, pyridinyl, pyrrolyl, N-methylpyrrolyl, oxazolyl, isoxazolyl, pyrazolyl, imidazolyl, triazolyl, oxadiazolyl, thiadiazolyl, pyrimidinyl, pyrazinyl, pyridazinyl, quinolinyl, benzofuranyl, thionaphthyl, or indolyl all optionally substituted with halo, $C_1$–$C_4$ alkyl or $C_1$–$C_4$ alkoxy.

The compounds of the present invention possess an asymmetric carbon labelled with an asterisk in the following formula:

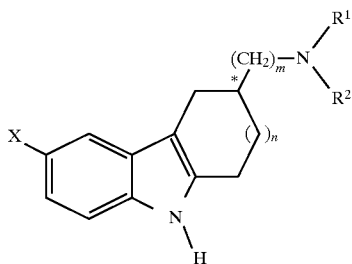

As such, each of the compounds of the present invention exists not only as the racemate but as individual d- and l-enantiomers as well:

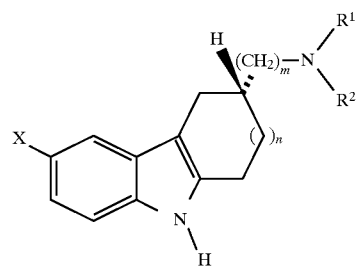

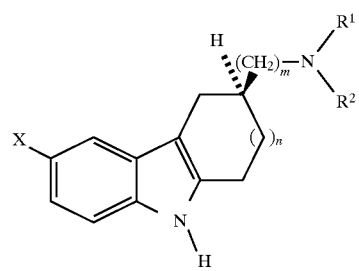

The compounds of the present invention include not only the dl-racemates, but also their respective optically active d- and l-enantiomers. Particularly useful chiral intermediates for the preparation of the compounds of this invention are those compounds where X is Br.

While all of the compounds of this invention are useful as 5-$HT_{1F}$ agonists, certain classes are preferred. The following paragraphs describe such preferred classes.

aa) $R^1$ is hydrogen;
ab) $R^1$ is $C_1$–$C_6$ alkyl;
ac) $R^1$ is ethyl;
ad) $R^1$ is methyl;
ae) $R^1$ is —$CH_2CH_2$—Ar where Ar is 1 -($C_1$–$C_6$ alkyl)-pyrazol-4-yl;
af) $R^1$ is —$CH_2CH_2$—Ar where Ar is 1-methylpyrazol-4-yl;
ag) $R^1$ is —$CH_2CH_2$—Ar where Ar is 1-isopropylpyrazol-4-yl;
ah) $R^2$ is hydrogen;
ai) $R^2$ is $C_1$–$C_6$ alkyl;
aj) $R^2$ is ethyl;
ak) $R^2$ is methyl;
al) $R^2$ is —$CH_2CH_2$—Ar where Ar is 1-($C_1$–$C_6$ alkyl)pyrazol-4-yl;
am) $R^2$ is —$CH_2CH_2$—Ar where Ar is 1-methylpyrazol-4-yl;
an) $R^2$ is —$CH_2CH_2$—Ar where Ar is 1-isopropylpyrazol-4-yl;
ao) X is —OH;
ap) X is —NHC(O)$R^3$;
aq) X is —NHC(Y)NH$R^4$;
ar) X is —NHC(O)O$R^5$;
as) X is —C(O)$R^6$;
at) X is —NHSO$_2R^7$;
au) $R^3$ is $C_1$–$C_6$ alkyl;
av) $R^3$ is $C_2$–$C_6$ alkenyl;
aw) $R^3$ is $C_3$–$C_6$ cycloalkyl;
ax) $R^3$ is cyclobutyl;
ay) $R^3$ is cyclopropyl;
az) $R^3$ is phenyl;

ba) $R^3$ is phenyl monosubstituted with halo;
bb) $R^3$ is phenyl monosubstituted with fluoro;
bc) $R^3$ is phenyl monosubstituted with chloro;
bd) $R^3$ is 4-fluorophenyl;
be) $R^3$ is 2-chlorophenyl;
bf) $R^3$ is phenyl monosubstituted with $C_1$–$C_4$ alkoxy;
bg) $R^3$ is phenyl monosubstituted with $C_1$–$C_4$ alkyl;
bh) $R^3$ is phenyl monosubstituted with methyl;
bi) $R^3$ is 2-methylphenyl;
bj) $R^3$ is phenyl disubstituted with halo;
bk) $R^3$ is 2-chloro-4-fluorophenyl;
bl) $R^3$ is a heterocycle;
bm) $R^3$ is furyl optionally substituted with $C_1$–$C_4$ alkyl, $C_1$–$C_4$ alkoxy, or halo;
bn) $R^3$ is 2-furyl;
bo) $R^3$ is 3-furyl;
bp) $R^3$ is thienyl optionally substituted with $C_1$–$C_4$ alkyl or $C_1$–$C_4$ alkoxy;
bq) $R^3$ is 2-thienyl;
br) $R^3$ is 3-thienyl;
bs) $R^3$ is pyridinyl optionally substituted with halo, $C_1$–$C_4$ alkyl or $C_1$–$C_4$ alkoxy;
bt) $R^3$ is 3-pyridinyl;
bu) $R^3$ is 4-pyridinyl;
bv) $R^3$ is 6-halo-3-pyridinyl;
bw) m is 0;
bx) m is 1;
by) n is 1;
bz) n is 2;
ca) Y is S;
cb) Y is O;
cc) The compound is a racemate;
cd) The compound is the 1-enantiomer;
ce) The compound is the d-enantiomer;
cf) The compound is a free base;
cg) The compound is a salt;
ch) The compound is the hydrochloride salt;
ci) The compound is the fumarate salt;
cj) The compound is the oxalate salt.

It will be understood that the above classes may be combined to form additional preferred classes.

The compounds of this invention are useful in a method for increasing activation of the 5-HT$_{1F}$ receptor for treating a variety of disorders which have been linked to decreased neurotransmission of serotonin in mammals. It is preferred that the mammal to be treated by the administration of compounds of this invention is human.

Since the compounds of this invention are amines, they are basic in nature and accordingly react with any of a number of inorganic and organic acids to form pharmaceutically acceptable acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as p-toluene-sulfonic acid, methanesulfonic acid, oxalic acid, p-bromo-phenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, b-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid, oxalic acid or fumaric acid.

The following group is illustrative of compounds contemplated within the scope of this invention:

6-propanoyl-3-(methyl)amino-1,2,3,4-tetrahydro-9H-carbazole hydrobromide 6-(2-methylpropanoyl)-3-(butyl)amino-1,2,3,4-tetrahydro-9H-carbazole fumarate 6-butanoyl-3-(isobutyl)amino-1,2,3,4-tetrahydro-9H--carbazole N-methyl-N-propyl-6-(sec-butanoyl)-3-amino-1,2,3,4-tetrahydro-9H-carbazole maleate 6-(2-methylbutanoyl)-3-(isopropyl)amino-1,2,3,4-tetrahydro-9H-carbazole 6-(3,3-dimethylbutanoyl)-3-(tert-butyl)amino-1,2,3,4-tetrahydro-9H-carbazole oxalate 6-(3-chlorobenzoyl)-3-(dipropyl)amino-1,2,3,4-tetrahydro-9H-carbazole methanesulfonate (+)-6-(2-bromobenzoyl)-3-(diethyl)amino-1,2,3,4-tetrahydro-9H-carbazole p-toluenesulfonate 6-(2-ethoxybenzoyl)-3-(isobutyl)amino-1,2,3,4-tetrahydro-9H-carbazole tartarate 6-(3-propoxybenzoyl)-3-(2-(1-methyl-1H-pyrazol-4-yl)ethyl)amino-1,2,3,4-tetrahydro-9H-carbazole trifluoromethanesulfonate N-(2-(1-isopropyl-1H-pyrazol-4-yl)ethyl)-N-ethyl-6-(3-butoxybenzoyl)-3-amino-1,2,3,4-tetrahydro-9H-carbazole 6-propanoyl-3-(methyl)aminomethyl-1,2,3,4-tetrahydro-9H-carbazole hydrobromide (−)-6-(2-methylpropanoyl)-3-(isobutyl)aminomethyl-1,2,3,4-tetrahydro-9H-carbazole fumarate 6-butanoyl-3-(isobutyl)aminomethyl-1,2,3,4-tetrahydro-9H-carbazole N-methyl-N-propyl-6-(sec-butanoyl)-3-aminomethyl-1,2,3,4-tetrahydro-9H-carbazole maleate 6-(2-methylbutanoyl)-3-(isopropyl)aminomethyl-1,2,3,4-tetrahydro-9H-carbazole 6-(3,3-dimethylbutanoyl)-3-(tert-butyl)amino-1,2,3,4-tetrahydro-9H-carbazole oxalate 6-(3-chlorobenzoyl)-3-(dimethyl)aminomethyl-1,2,3,4-tetrahydro-9H-carbazole methanesulfonate 6-(2-bromobenzoyl)-3-(diethyl)aminomethyl-1,2,3,4-tetrahydro-9H-carbazole p-toluenesulfonate 6-(2-ethoxybenzoyl)-3-(isobutyl)aminomethyl-1,2,3,4-tetrahydro-9H-carbazole tartarate 6-(3-propoxybenzoyl)-3-(2-(1-methyl-1H-pyrazol-4-yl)ethyl)aminomethyl-1,2,3,4-tetrahydro-9H-carbazole trifluoromethanesulfonate (+)-N-(2-(1-isopropyl-1H-pyrazol-4-yl)ethyl)-N-ethyl-6-(3-butoxybenzoyl)-3-aminomethyl-1,2,3,4-tetrahydro-9H-carbazole brosylate 7-propanoyl-4-(methyl)aminocyclohepta[7,6-b]indole hydrobromide 7-(2-methylpropanoyl)-4-(isopropyl)aminocyclohepta[7,6-b]indole fumarate 7-butanoyl-4-(isobutyl)aminocyclohepta[7,6-b]indole N-methyl-N-propyl-7-(sec-butanoyl)-4-aminocyclohepta[7,6-b]indole maleate 7-(2-methylbutanoyl)-4-(isopropyl)aminocyclohepta[7,6-b]indole 7-(3,3-dimethylbutanoyl)-4-(tert-butyl)aminocyclohepta[7,6-b]indole oxalate 7-(3-chlorobenzoyl)-4-(ethyl)aminocyclohepta[7,6-b]indole methanesulfonate 7-(2-bromobenzoyl)-4-(diethyl)aminocyclohepta[7,6-b]indole p-toluenesulfonate 7-(2-ethoxybenzoyl)-4-(isobutyl)aminocyclohepta[7,6-b]indole tartarate 7-(3-propoxybenzoyl)-4-(2-(1-methyl-1H-pyrazol-4-yl)ethyl)aminocyclohepta[7,6-b]indole trifluoromethanesulfonate (−)-N-(2-(1-isopropyl-1H-pyrazol-4-yl)ethyl)-N-ethyl-7-(3-butoxybenzoyl)-4-aminocyclohepta[7,6-b]indole 7-propanoyl-4-(methyl)aminomethylcyclohepta[7,6-b]indole hydrobromide 7-(2-methylpropanoyl)-4-(isopropyl)aminomethylcyclohepta[7,6-b]indole fumarate 7-butanoyl-4-(isobutyl)aminomethylcyclohepta[7,6-b]indole N-methyl-N-propyl-7-(sec-butanoyl)-4-aminocyclohepta[7,6-b]indole maleate 7-(2-methylbutanoyl)-4-(isopropyl)aminomethylcyclohepta[7,6-b]indole 7-(3,3-dimethylbutanoyl)-4-(tert-butyl)aminomethylcyclohepta[7,6-b]indole oxalate 7-(3-chlorobenzoyl)-4-(butyl)aminomethylcyclohepta[7,6-b]indole methanesulfonate 7-(2-bromobenzoyl)-4-(diethyl)aminomethylcyclohepta[7,6-b]indole p-toluenesulfonate 7-(2-ethoxybenzoyl)-4-(isobutyl)aminomethylcyclohepta[7,6-b]indole tartarate 7-(3-propoxybenzoyl)-4-(2-(1-methyl-1H-pyrazol-4-yl)ethyl)aminomethylcyclohepta[7,6-b]indole trifluoromethanesulfonate N-(2-(1-isopropyl-1H-pyrazol-4-yl)ethyl)-N-ethyl-7-(3-butoxybenzoyl)-4-aminomethylcyclohepta[7,6-b]indole 6-isopropoxycarbonylamino-3-(ethyl)amino-1,2,3,6-tetrahydropyridin-4-yl)-2-ethyl-1H-indole phosphate 6-(1-buten-4-yloxy)carbonylamino-3-(isopropyl)amino-1,2,3,4-tetrahydro-9H-carbazole maleate 6-(1-penten-5-yloxy)carbonylamino-3-(isobutyl)amino-1,2,3,4-tetrahydro-9H-carbazole malonate N-isopropyl-N-methyl-6-(1-buten-4-yloxy)carbonylamino-3-amino-1,2,3,4-tetrahydro-9H-carbazole benzoate 6-(3-penten-5-yloxy)carbonylamino-3-(tert-butyl)amino-1,2,3,4-tetrahydro-9H-carbazole 6-(2-hexen-6-yloxy)carbonylamino-3-(2-pentyl)amino-1,2,3,4-tetrahydro-9H-carbazole 4-chlorobenzoate 6-(2-chlorophenoxy)carbonylamino-3-(2-(1-isopropyl-1H-pyrazol-4-yl)ethyl)amino-1,2,3,4-tetrahydro-9H-carbazole glycollate (+)-6-(3-fluorophenoxy)carbonylamino-3-(2-(1-isopropyl-1H-pyrazol-4-yl)ethyl)amino-1,2,3,4-tetrahydro-9H-carbazole 6-(4-bromophenoxy)carbonylamino-3-(methyl)amino-1,2,3,4-tetrahydro-9H-carbazole hippurate 6-isopropoxycarbonylamino-3-(ethyl)aminomethyl-1,2,3,4-tetrahydro-9H-carbazole phosphate 6-(1-buten-4-yloxy)carbonylamino-3-(isopropyl)aminomethyl-1,2,3,4-tetrahydro-9H-carbazole maleate 6-(1-penten-5-yloxy)carbonylamino-3-(isobutyl)aminomethyl-1,2,3,4-tetrahydro-9H-carbazole malonate N-isopropyl-N-methyl-6-(1-buten-4-yloxy)carbonylamino-3-aminomethyl-1,2,3,4-tetrahydro-9H-carbazole benzoate 6-(3-penten-5-yloxy)carbonylamino-3-(tert-butyl)aminomethyl-1,2,3,4-tetrahydro-9H-carbazole 6-(2-hexen-6-yloxy)carbonylamino-3-(isobutyl)aminomethyl-1,2,3,4-tetrahydro-9H-carbazole 4-chlorobenzoate 6-(2-chlorophenoxy)carbonylamino-3-(2-(1-isopropyl-1H-pyrazol-4-yl)ethyl)aminomethyl-1,2,3,4-tetrahydro-9H-carbazole glycollate 6-(3-fluorophenoxy)carbonylamino-3-(2-(1-isopropyl-1H-pyrazol-4-yl)ethyl)aminomethyl-1,2,3,4-tetrahydro-9H-carbazole 6-(4-bromophenoxy)carbonylamino-3-(methyl)aminomethyl-1,2,3,4-tetrahydro-9H-carbazole hippurate 7-isopropoxycarbonylamino-4-(ethyl)amino-cyclohepta[7,6-b]indole phosphate (−)-7-(1-buten-4-yloxy)carbonylamino-4-(isopropyl)amino-cyclohepta[7,6-b]indole maleate 7-(1-penten-5-yloxy)carbonylamino-4-(isobutyl)amino-cyclohepta[7,6-b]indole malonate N-isopropyl-N-methyl-7-(1-buten-4-yloxy)carbonylamino-4-amino-cyclohepta[7,6-b]indole benzoate 7-(3-penten-5-yloxy)carbonylamino-4-(tert-butyl)amino-cyclohepta[7,6-b]indole 7-(2-hexen-6-yloxy)carbonylamino-4-amino-cyclohepta[7,6-b]indole 4-chlorobenzoate 7-(2-chlorophenoxy)carbonylamino-4-(2-(1-isopropyl-1H-pyrazol-4-yl)ethyl)amino-cyclohepta[7,6-b]indole glycollate 7-(3-fluorophenoxy)carbonylamino-4-(2-(1-methyl-1H-pyrazol-4-yl)ethyl)amino-cyclohepta[7,6-b]indole 7-(4-bromophenoxy)carbonylamino-4-(methyl)aminocyclohepta[7,6-b]indole hippurate 7-isopropoxycarbonylamino-4-(ethyl)aminomethylcyclohepta[7,6-b]indole phosphate 7-(1-buten-4-yloxy)carbonylamino-4-(isopropyl)aminomethylcyclohepta[7,6-b]indole maleate 7-(1-penten-5-yloxy)carbonylamino-4-(isobutyl)aminomethylcyclohepta[7,6-b]indole malonate N-isopropyl-N-methyl-7-(1-buten-4-yloxy)carbonylamino-4-aminomethylcyclohepta[7,6-b]indole benzoate 7-(3-penten-5-yloxy)carbonylamino-4-(tert-butyl)aminomethylcyclohepta[7,6-b]indole (+)-7-(2-hexen-7-yloxy)carbonylamino-4-aminomethylcyclohepta[7,6-b]indole 4-chlorobenzoate 7-(2-chlorophenoxy)carbonylamino-4-(2-(1-isopropyl-1H-pyrazol-4-yl)ethyl)aminomethylcyclohepta[7,6-b]indole glycollate 7-(3-fluorophenoxy)carbonylamino-4-(2-(1-isopropyl-1H-pyrazol-4-yl)ethyl)aminomethylcyclohepta[7,6-b]indole 7-(4-bromophenoxy)carbonylamino-4-(methyl)aminomethylcyclohepta[7,6-b]indole hippurate N-ethyl-N'-(3-(methyl)amino-1,2,3,4-tetrahydro-9H-carbazol-6-yl)thiourea citrate N-isopropyl-N'-(3-(sec-butyl)amino-1,2,3,4-tetrahydro-9H-carbazol-6-yl)thiourea acetate N-propyl-N'-(3-(isobutyl)amino-1,2,3,4-tetrahydro-9H-carbazol-6-yl)thiourea decanoate N-butyl-N'-(3-(isopropyl)amino-1,2,3,4-tetrahydro-9H-carbazol-6-yl)thiourea formate N-pentyl-N'-(3-(2-(1-isopropyl-1H-pyrazol-4-yl)ethyl)amino-1,2,3,4-tetrahydro-9H-carbazol-6-yl)urea caproate N-(3-chloro)phenyl-N'-(dipropyl)amino-1,2,3,4-tetrahydro-9H-carbazol-6-yl)urea N-(4-bromo)phenyl-N'-(3-((sec-butyl)amino-1,2,3,4-tetrahydro-9H-carbazol-6-yl)urea (−)-N-hexyl-N'-(3-amino-1,2,3,4-tetrahydro-9H-carbazol-6-yl)urea N-ethyl-N'-(3-(methyl)aminomethyl-1,2,3,4-tetrahydro-9H-carbazol-6-yl)thiourea citrate N-isopropyl-N'-(3-(sec-butyl)aminomethyl-1,2,3,4-tetrahydro-9H-carbazol-6-yl)thiourea acetate N-propyl-N'-(3-(diethyl)aminomethyl-1,2,3,4-tetrahydro-9H-carbazol-6-yl)thiourea decanoate N-butyl-N'-(3-(isopropyl)aminomethyl-1,2,3,4-tetrahydro-9H-carbazol-6-yl)thiourea formate N-pentyl-N'-(3-(2-(1-isopropyl-1H-pyrazol-4-yl)ethyl)aminomethyl-1,2,3,4-tetrahydro-9H-carbazol-6-yl)urea caproate N-(3-chloro)phenyl-N'-(dipropyl)aminomethyl-1,2,3,4-tetrahydro-9H-carbazol-6-yl)urea N-(4-bromo)phenyl-N'-(3-((sec-butyl)aminomethyl-1,2,3,4-tetrahydro-9H-carbazol-6-yl)urea N-hexyl-N'-(3-aminomethyl-1,2,3,4-tetrahydro-9H-carbazol-6-yl)urea N-ethyl-N'-(4-(methyl)aminocyclohepta[7,6-b]indol-7-yl)thiourea citrate N-isopropyl-N'-(4-(sec-butyl)aminocyclohepta[7,6-b]indol-7-yl)thiourea acetate N-propyl-N'-(4-(isobutyl)aminocyclohepta[7,6-b]indol-7-yl)thiourea decanoate N-butyl-N'-(4-(isopropyl)aminocyclohepta[7,6-b]indol-7-yl)thiourea formate N-pentyl-N'-(4-(2-(1-isopropyl-1H-pyrazol-4-yl)ethyl)aminocyclohepta[7,6-b]indol-7-yl)urea caproate N-(3-chloro)phenyl-N'-(4-(dipropyl)aminocyclohepta[7,6-b]indol-7-yl)urea N-(4-bromo)phenyl-N'-(4-((sec-butyl)aminocyclohepta[7,6-b]indol-7-yl)urea N-hexyl-N'-(4-aminocyclohepta[7,6-b]indol-7-yl)urea N-ethyl-N'-(4-(methyl)aminomethylcyclohepta[7,6-b]indol-7-yl)thiourea citrate (+)-N-isopropyl-N'-(4-(sec-butyl)aminomethylcyclohepta[7,6-b]indol-7-yl)thiourea acetate N-propyl-N'-(4-(dibutyl)aminomethylcyclohepta[7,6-b]indol-7-yl)thiourea decanoate N-butyl-N'-(4-(isopropyl)aminomethylcyclohepta[7,6-b]indol-7-yl)thiourea formate N-pentyl-N'-(4-(2-(1-isopropyl-1H-pyrazol-4-yl)ethyl)aminomethylcyclohepta[7,6-b]indol-7-yl)urea caproate N-(3-chloro)phenyl-N'-(4-(dipropyl)aminomethylcyclohepta[7,6-b]indol-7-yl)urea (−)-N-(4-bromo)phenyl-N'-(4-((sec-butyl)aminomethylcyclohepta[7,6-b]indol-7-yl)urea N-hexyl-N'-(4-aminomethylcyclohepta[7,6-b]indol-7-yl)urea 6-(acetyl)amino-3-amino-1,2,3,4-tetrahydro-9H-carbazole phenylacetate 6-(butyroyl)amino-3-(diethyl)amino-1,2,3,4-tetrahydro-9H-carbazole bisulfate 6-(pentanoyl)amino-3-(propyl)amino-1,2,3,4-tetrahydro-9H-carbazole hydrochloride 6-(2-methylbutanoyl)amino-3-(1-phenyleth-2-yl)amino-1,2,3,4-tetrahydro-9H-carbazole hydrochloride 6-(2,2-dimethylpropanoyl)amino-3-(isobutyl)amino-1,2,3,4-tetrahydro-9H-carbazole phthalate 6-(heptanoyl)amino-3-(isopropyl)amino-1,2,3,4-tetrahydro-9H-carbazole hydrobromide 6-(4-phenylbutanoyl)amino-3-(dipropyl)amino-1,2,3,4-tetrahydro-9H-carbazole xylenesulfonate 6-(phenoxyacetyl)amino-3-(1-(2-chlorophenyl)eth-2-yl)amino-1,2,3,4-tetrahydro-9H-carbazole mandelate 6-(phenoxybutanoyl)amino-3-(1-(3-iodophenyl)eth-2-yl)amino-1,2,3,4-tetrahydro-9H-carbazole 6-(butoxyacetyl)amino-3-(1-(4-bromophenyl)eth-2-yl)amino-1,2,3,4-tetrahydro-9H-carbazole 6-(butoxycarbonylacetyl)amino-3-(2-(1-isopropyl-1H-pyrazol-4-yl)ethyl)amino-1,2,3,4-tetrahydro-9H-carbazole N-methyl-N-propyl-6-(4-fluorobenzoyl)amino-3-amino-1,2,3,4-tetrahydro-9H-carbazole 6-(2-chlorobenzoyl)amino-3-(diethyl)amino-1,2,3,4-tetrahydro-9H-carbazole 6-(3-ethylbenzoyl)amino-3-(propyl)amino-1,2,3,4-tetrahydro-9H-carbazole naphthalene-1-sulfonate 6-(4-ethoxybenzoyl)amino-3-(sec-butyl)amino-1,2,3,4-tetrahydro-9H-carbazole (+)-N-methyl-N-(2-(1-ethyl-1H-pyrazol-4-yl)ethyl)-6-(2-butoxybenzoyl)amino-3-amino-1,2,3,4-tetrahydro-9H-carbazole 6-(3-thiomethylbenzoyl)amino-3-(isopropyl)amino-1,2,3,4-tetrahydro-9H-carbazole 6-(4-thiopropylbenzoyl)amino-3-amino-1,2,3,4-tetrahydro-9H-carbazole 6-(2-nitrobenzoyl)amino-3-(isopropyl)amino-1,2,3,4-tetrahydro-9H-carbazole 6-(2-cyanobenzoyl)amino-3-(dimethyl)amino-1,2,3,4-tetrahydro-9H-carbazole 6-(2-(dimethylamino)benzoyl)amino-3-amino-1,2,3,4-tetrahydro-9H-carbazole 6-(2-trifluoromethoxybenzoyl)amino-3-(diethyl)amino-1,2,3,4-tetrahydro-9H-carbazole 6-(3-trifluoromethoxybenzoyl)amino-3-amino-1,2,3,4-tetrahydro-9H-carbazole hydroiodide 6-(2-thienoyl)amino-3-(phenethyl)amino-1,2,3,4-tetrahydro-9H-carbazole 6-(3-thienoyl)amino-3-(dimethyl)amino-1,2,3,4-tetrahydro-9H-carbazole 6-(2-furoyl)amino-3-(propyl)amino-1,2,3,4-tetrahydro-9H-carbazole 6-(3-furoyl)amino-3-(diethyl)amino-1,2,3,4-tetrahydro-9H-carbazole 6-(2-chloro-4-fluoro)benzoyl-3-(methyl)amino-1,2,3,4-tetrahydro-9H-carbazole 6-(3-pyridinoyl)amino-3-(diethyl)amino-1,2,3,4-tetrahydro-9H-carbazole 6-(3-chloro-2-pyridinoyl)amino-3-(diethyl)amino-1,2,3,4-tetrahydro-9H-carbazole 6-(acetyl)amino-3-(methyl)aminomethyl-1,2,3,4-tetrahydro-9H-carbazole phenylacetate 6-(butyroyl)amino-3-(butyl)aminomethyl-1,2,3,4-tetrahydro-9H-carbazole bisulfate 6-(pentanoyl)amino-3-(phenethyl)aminomethyl-1,2,3,4-tetrahydro-9H-carbazole hydrochloride 6-(2-methylbutanoyl)amino-3-(1-phenyleth-2-yl)aminomethyl-1,2,3,4-tetrahydro-9H-carbazole hydrochloride 6-(2,2-dimethylpropanoyl)amino-3-(isobutyl)aminomethyl-1,2,3,4-tetrahydro-9H-carbazole phthalate (−)-6-(heptanoyl)amino-3-(isopropyl)aminomethyl-1,2,3,4-tetrahydro-9H-carbazole hydrobromide 6-(4-phenylbutanoyl)amino-3-(dipropyl)aminomethyl-1,2,3,4-tetrahydro-9H-carbazole xylenesulfonate 6-(phenoxyacetyl)amino-3 (phenethyl)aminomethyl-1,2,3,4-tetrahydro-9H-carbazole mandelate 6-(phenoxybutanoyl)amino-3-(isopropyl)aminomethyl-1,2,3,4-tetrahydro-9H-carbazole 6-(butoxyacetyl)amino-3-(1-(4-bromophenyl)eth-2-yl)aminomethyl-1,2,3,4-tetrahydro-9H-carbazole 6-(butoxycarbonylacetyl)amino-3-(2-(1-isopropyl-1H-pyrazol-4-yl)ethyl)aminomethyl-1,2,3,4-tetrahydro-9H-carbazole N-methyl-N-propyl-6-(4-fluorobenzoyl)amino-3-aminomethyl-1,2,3,4-tetrahydro-9H-carbazole 6-(2-chlorobenzoyl)amino-3-(diethyl)aminomethyl-1,2,3,4-tetrahydro-9H-carbazole 6-(3-ethylbenzoyl)amino-3-(propyl)aminomethyl-1,2,3,4-tetrahydro-9H-carbazole naphthalene-1-sulfonate 6-(4-ethoxybenzoyl)amino-3-(sec-butyl)aminomethyl-1,2,3,4-tetrahydro-9H-carbazole N-methyl-N-(2-(1-ethyl-1H-pyrazol-4-yl)ethyl)-6-(2-butoxybenzoyl)amino-3-aminomethyl-1,2,3,4-tetrahydro-9H-carbazole 6-(3-thiomethylbenzoyl)amino-3-(isopropyl)aminomethyl-1,2,3,4-tetrahydro-9H-carbazole 6-(4-thiopropylbenzoyl)amino-3-aminomethyl-1,2,3,4-tetrahydro-9H-carbazole 6-(2-nitrobenzoyl)amino-3-(isopropyl)aminomethyl-1,2,3,4-tetrahydro-9H-carbazole 6-(2-cyanobenzoyl)amino-3-(dimethyl)aminomethyl-1,2,3,4-tetrahydro-9H-carbazole 6-(2-(dimethylamino)benzoyl)amino-3-(dipropyl)aminomethyl-1,2,3,4-tetrahydro-9H-carbazole 6-(2-trifluoromethoxybenzoyl)amino-3-(diethyl)aminomethyl-1,2,3,4-tetrahydro-9H-carbazole 6-(3-trifluoromethoxybenzoyl)amino-3-aminomethyl-1,2,3,4-tetrahydro-9H-carbazole hydroiodide 6-(2-thienoyl)amino-3-(propyl)aminomethyl-1,2,3,4-tetrahydro-9H-carbazole (+) -6-(3-thienoyl)amino-3-(dimethyl)aminomethyl-1,2,3,4-tetrahydro-9H-carbazole 6-(2-furoyl)amino-3-(propyl)aminomethyl-1,2,3,4-tetrahydro-9H-carbazole 6-(3-furoyl)amino-3-(diethyl)aminomethyl-1,2,3,4-tetrahydro-9H-carbazole 6-(2-chloro-4-fluoro)benzoyl-3-(methyl)aminomethyl-1,2,3,4-tetrahydro-9H-carbazole 6-(3-pyridinoyl)amino-3-(diethyl)aminomethyl-1,2,3,4-tetrahydro-9H-carbazole 6-(3-chloro-2-pyridinoyl)amino-3-(diethyl)aminomethyl-1,2,3,4-tetrahydro-9H-carbazole 7-(acetyl)amino-4-(phenethyl)aminocyclohepta[7,6-b]indole phenylacetate 7-(butyroyl)amino-4-aminocyclohepta[7,6-b]indole bisulfate 7-(pentanoyl)amino-4-aminocyclohepta[7,6-b]indole hydrochloride 7-(2-methylbutanoyl)amino-4-(1-phenyleth-2-yl)aminocyclohepta[7,6-b]indole hydrochloride 7-(2,2-dimethylpropanoyl)amino-4-(isobutyl)aminocyclohepta[7,6-b]indole phthalate 7-(heptanoyl)amino-4-(isopropyl)aminocyclohepta[7,6-b]indole hydrobromide 7-(4-phenylbutanoyl)amino-4-(dipropyl)aminocyclohepta[7,6-b]indole xylenesulfonate 7-(phenoxyacetyl)amino-4-aminocyclohepta[7,6-b]indole mandelate 7-(phenoxybutanoyl)amino-4-(methyl)aminocyclohepta[7,6-b]indole 7-(butoxyacetyl)amino-4-(1-(4-bromophenyl)eth-2-yl)aminocyclohepta[7,6-b]indole 7-(butoxycarbonylacetyl)amino-4-(2-(1-isopropyl-1H-pyrazol-4-yl)ethyl)aminocyclohepta[7,6-b]indole N-methyl-N-propyl-7-(4-fluorobenzoyl)amino-4-aminocyclohepta[7,6-b]indole (+)-7-(2-chlorobenzoyl)amino-4-(diethyl)aminocyclohepta[7,6-b]indole 7-(3-ethylbenzoyl)amino-4-(propyl)aminocyclohepta[7,6-b]indole naphthalene-1-sulfonate 7-(4-ethoxybenzoyl)amino-4-(sec-butyl)aminocyclohepta[7,6-b]indole N-methyl-N-(2-(1-ethyl-1H-pyrazol-4-yl)ethyl)-7-(2-butoxybenzoyl)amino-4-aminocyclohepta[7,6-b]indole 7-(3-thiomethylbenzoyl)amino-4-(isopropyl)aminocyclohepta[7,6-b]indole 7-(4-thiopropylbenzoyl)amino-4-aminocyclohepta[7,6-b]indole 7-(2-nitrobenzoyl)amino-4-(isopropyl)aminocyclohepta[7,6-b]indole 7-(2-cyanobenzoyl)amino-4-(dimethyl)aminocyclohepta[7,6-b]indole 7-(2-(dimethylamino)benzoyl)amino-4-(isobutyl)aminocyclohepta[7,6-b]indole 7-(2-trifluoromethoxybenzoyl)amino-4-(diethyl)aminocyclohepta[7,6-b]indole 7-(3-trifluoromethoxybenzoyl)amino-4-aminocyclohepta[7,6-b]indole hydroiodide (−)-7-(2-thienoyl)amino-4-(methyl)aminocyclohepta[7,6-b]indole
7-(3-thienoyl)amino-4-(dimethyl)aminocyclohepta[7,6-b]indole
7-(2-furoyl)amino-4-(propyl)aminocyclohepta[7,6-b]indole
7-(3-furoyl)amino-4-(diethyl)aminocyclohepta[7,6-b]indole
7-(2-chloro-4-fluoro)benzoyl-4-(methyl)aminocyclohepta[7,6-b]indole
7-(3-pyridinoyl)amino-4-(diethyl)aminocyclohepta[7,6-b]indole
7-(3-chloro-2-pyridinoyl)amino-4-(diethyl)aminocyclohepta[7,6-b]indole
7-(acetyl)amino-4-(phenethyl)aminomethylcyclohepta[7,6-b]indole phenylacetate
7-(butyroyl)amino-4-(sec-butyl)aminomethylcyclohepta[7,6-b]indole bisulfate
7-(pentanoyl)amino-4-aminomethylcyclohepta[7,6-b]indole hydrochloride
7-(2-methylbutanoyl)amino-4-(1-phenyleth-2-yl)aminomethylcyclohepta[7,6-b]indole hydrochloride
7-(2,2-dimethylpropanoyl)amino-4-(isobutyl)aminomethylcyclohepta[7,6-b]indole phthalate
7-(heptanoyl)amino-4-(isopropyl)aminomethylcyclohepta[7,6-b]indole hydrobromide
7-(4-phenylbutanoyl)amino-4-(dipropyl)aminocyclohepta[7,6-b]indole xylenesulfonate
N-methyl-N-propyl-7-(phenoxyacetyl)amino-4-aminomethylcyclohepta-[7,6-b]indole mandelate
7-(butanoyl)amino-4-aminomethylcyclohepta-[7,6-b]indole
7-(acetyl)amino-4-(1-(4-bromophenyl)eth-2-yl)aminomethylcyclohepta[7,6-b]indole
7-(acetyl)amino-4-(2-(1-isopropyl-1H-pyrazol-4-yl)ethyl)aminomethylcyclohepta[7,6-b]indole
N-methyl-N-propyl-7-(4-fluorobenzoyl)amino-4-aminomethylcyclohepta[7,6-b]indole
7-(2-chlorobenzoyl)amino-4-(diethyl)aminomethylcyclohepta[7,6-b]indole
7-(3-ethylbenzoyl)amino-4-(propyl)aminomethylcyclohepta[7,6-b]indole naphthalene-1-sulfonate
(+)-7-(4-ethoxybenzoyl)amino-4-(sec-butyl)aminocyclohepta[7,6-b]indole
N-methyl-N-(2-(1-ethyl-1H-pyrazol-4-yl)ethyl)-7-(2-butoxybenzoyl)amino-4-aminomethylcyclohepta[7,6-b]indole
7-(3-thiomethylbenzoyl)amino-4-(isopropyl)aminomethylcyclohepta[7,6-b]indole
7-(4-thiopropylbenzoyl)amino-4-aminomethylcyclohepta[7,6-b]indole
7-(2-nitrobenzoyl)amino-4-(isopropyl)aminocyclohepta[7,6-b]indole
7-(2-cyanobenzoyl)amino-4-(dimethyl)aminomethylcyclohepta[7,6-b]indole
7-(2-(dimethylamino)benzoyl)amino-4-(t-butyl)aminomethylcyclohepta[7,6-b]indole
7-(2-trifluoromethoxybenzoyl)amino-4-(diethyl)aminomethylcyclohepta[7,6-b]indole
7-(3-trifluoromethoxybenzoyl)amino-4-aminocyclohepta[7,6-b]indole hydroiodide
7-(2-thienoyl)amino-4-(butyl)aminomethylcyclohepta[7,6-b]indole
7-(3-thienoyl)amino-4-(dimethyl)aminomethylcyclohepta[7,6-b]indole
(+)-7-(2-furoyl)amino-4-(propyl)aminomethylcyclohepta[7,6-b]indole
7-(3-furoyl)amino-4-(diethyl)aminomethylcyclohepta[7,6-b]indole
7-(2-chloro-4-fluoro)benzoyl-4-(methyl)aminocyclohepta[7,6-b]indole
7-(3-pyridinoyl)amino-4-(diethyl)aminomethylcyclohepta[7,6-b]indole
7-(3-chloro-2-pyridinoyl)amino-4-(diethyl)aminocyclohepta[7,6-b]indole The compounds of this invention are prepared by methods well known to one of ordinary skill in the art. Compounds of the present invention where m is 0 and n is 1 are members of the class commonly known as 6-substituted-3-amino-1,2,3,4-tetrahydro-9H-carbazoles. Members of this class are conveniently prepared by the Fischer indole synthesis as illustrated in Synthetic Scheme I. X' is bromo, benzyloxy, $R^3C(O)NH—$, $R^4NHC(Y)NH—$, $R^5OC(O)NH—$, or $R^7SO_2NH—$; $R^1$ and $R^2$ are independently $C_1$–$C_6$ alkyl, benzyl or, together with the nitrogen, form a phthalimido group; and Y, $R^3$, $R^4$, $R^5$ and $R^7$ are as previously defined.

Synthetic Scheme I

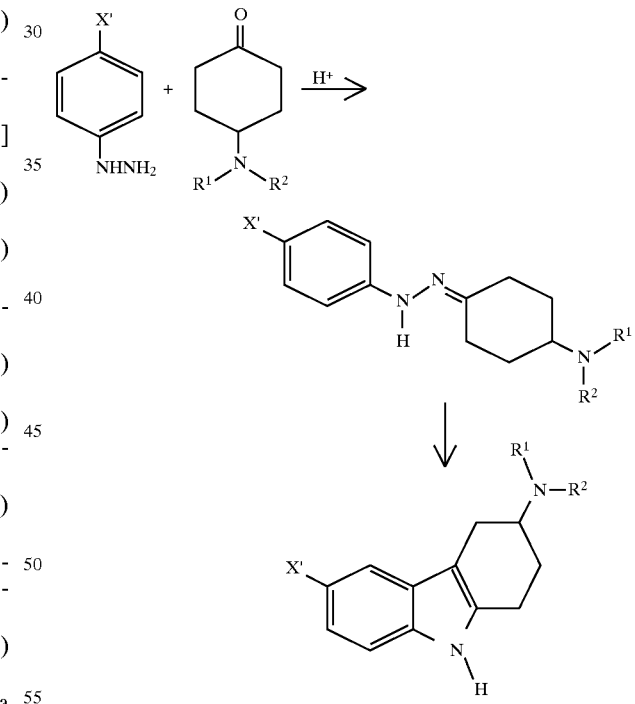

The phenylhydrazine and 4-aminocyclohexanone are condensed together in a suitable solvent, typically a lower alkanol such as ethanol, in the presence of a catalytic amount of acid, such as hydrogen chloride, to give the resultant phenylhydrazone. The reaction is typically performed at from about room temperature to reflux for from about 1 to 24 hours. Once the condensation is complete, the resulting phenylhydrazone may be isolated from the reaction mixture by the addition of water or an aqueous solution of a base such as potassium carbonate if desired. The product separates from the mixture as an oil or a solid. The product may be extracted with a water immiscible solvent, typically dichloromethane, or filtered if appropriate. The product may be used in the next step with or without further purification. The phenylhydrazone undergoes a Fischer indole cyclization in the presence of excess acid. This may be accomplished by dissolving the phenylhydrazone in a neat acid, for example, acetic acid. Alternatively, the phenyl hydrazone may be dissolved in a lower alkanol which has been treated with an acid, for example, ethanolic hydrogen chloride. If the phenylhydrazone prepared as described above requires no further purification, the original reaction mixture may conveniently be treated with an appropriate acid without isolation of the phenylhydrazone. Many times, the Fischer indole cyclization occurs upon formation of the phenylhydrazone, giving the desired product in one step. The reaction is performed at from about room temperature to reflux for from about 1 to 24 hours. The reaction product may be recovered by direct filtration, or by extraction after removal of solvent and neutralization of acid by the addition of aqueous base. The product may be purified by recrystallization or chromatography as required.

The phenylhydrazines required for the preparation of compounds of the invention are either commercially available or may be prepared by methods well known to those skilled in the art. Phenylhydrazines where X' is $R^3C(O)NH—$, $R^4NHC(Y)NH—$, $R^5OC(O)NH—$ and $R^7SO_2NH—$ are prepared from 4-nitroaniline as described in Synthetic Scheme II. Y, $R^3$, $R^4$ $R^5$ and $R^7$ are as previously defined.

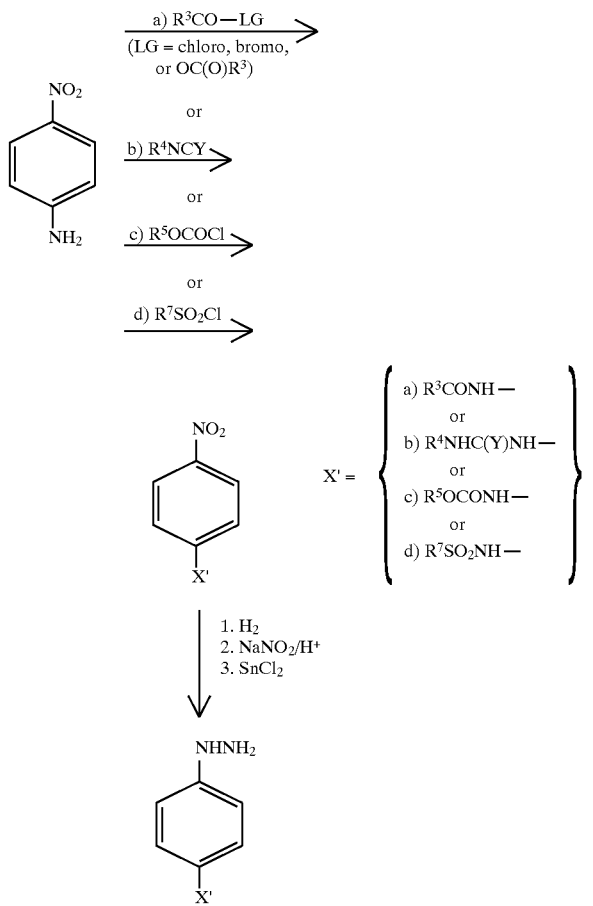

Compounds where X' is $R^4NHC(Y)NH—$ are prepared by treating a solution of 4-nitroaniline in a suitable solvent, such as chloroform or dichloromethane, with an appropriate isocyanate or isothiocyanate. If necessary, an excess of the isocyanate or isothiocyanate is employed to ensure complete reaction of the starting amine. The reactions are performed at about ambient to about 45° C., for from about three hours to about three days. Typically, the product may be isolated by washing the reaction with water and concentrating the remaining organics under reduced pressure. When an excess of isocyanate or isothiocyanate has been used, however, a polymer bound primary or secondary amine, such as an aminomethylated polystyrene, may be conveniently added to react with the excess reagent. Isolation of products from reactions where a polymer bound reagent has been used is greatly simplified, requiring only filtration of the reaction mixture and then concentration of the filtrate under reduced pressure. The product from these reactions may be purified chromatographically or recrystallized from a suitable solvent if desired.

Substituted nitroanilines where X' is $R^5OC(O)NH—$ are prepared by treating a solution of 4-nitroaniline in a suitable solvent, such as chloroform or dichloromethane, with an appropriate chloroformate in the presence of a base, or by treatment with an appropriate carbonate of structure $(R^5O)_2C(O)$. Suitable bases include amines typically used as acid scavengers, such as pyridine or triethylamine, or commercially available polymer bound bases such as polyvinylpyridine. Likewise, substituted nitroanilines where X' is $R^3C(O)NH—$ or $R^7SO_2NH—$ are prepared by reacting 4-nitroaniline with an appropriate carboxylic acid or sulfonyl chloride, bromide or anhydride, optionally in the presence of an acylation catalyst such as dimethylaminopyridine, in the presence of a suitable base, such as those described supra.

Alternatively, substituted nitroanilines where X' is $R^3C(O)NH—$ are prepared by reacting 4-nitroaniline with an appropriate carboxylic acid in the presence of typical peptide coupling reagents such as N,N'-carbonyldiimidazole (CDI), N,N'-dicyclohexylcarbodiimide (DCC) and 1-(3-dimethylaminopropyl)-3-ethylcarbodiimide hydrochloride (EDC). A polymer supported form of EDC has been described (*Tetrahedron Letters*, 34(48), 7685 (1993)) and is very useful for the preparation of the compounds of the present invention. The product from these reactions is isolated and purified as described above.

The substituted nitroanilines are hydrogenated over a precious metal catalyst, preferably platinum on carbon, and hydrogenated at about ambient temperature at an initial pressure of about 60 p.s.i. for from about 1 to 24 hours in a suitable solvent, such as a lower alkanol or tetrahydrofuran, to give the corresponding amino derivative. This amino derivative is then dissolved in a concentrated acid, such as phosphoric, hydrochloric or hydrobromic acid, and treated with sodium nitrite at a temperature about or below 0° C. After stirring for about an hour, the reaction mixture is added to a solution of tin(II) chloride in concentrated hydrochloric acid and the mixture stirred at about 0° C. for about an hour. The product is isolated by treating the reaction mixture with an aqueous base until it is strongly basic and then extracting with a water immiscible solvent such as ethyl acetate. The hydrazine product may be further purified by chromatography or crystallization prior to further reaction if desired.

The 4-substituted cyclohexanones required for the preparation of compounds of the invention are available by methods well known in the art as illustrated in Synthetic Scheme III. $R^1$ and $R^2$ independently hydrogen, $C_1$–$C_6$ alkyl or benzyl.

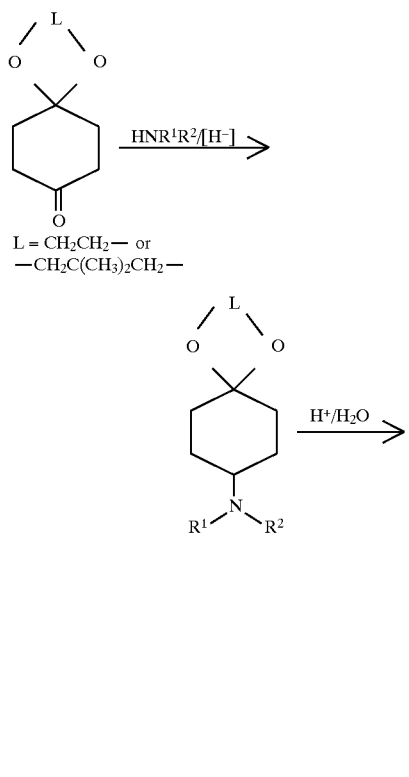

Synthetic Scheme III

L = CH$_2$CH$_2$— or
—CH$_2$C(CH$_3$)$_2$CH$_2$—

The 1,4-cyclohexanedione monoketal is reductively aminated with an appropriate amine under standard conditions to give the corresponding 4-aminocyclohexanone ketal. The ketal is then deprotected under aqueous acid conditions to prepare the corresponding 4-aminocyclohexanone.

Compounds of the invention where $R^1=R^2=H$ are prepared from 4-(1-phthlimidyl)cyclohexanone which is available by methods well known in the art, for example, King et al. (*Journal of Medicinal Chemistry*, 36, 1918 (1993)). Briefly, 4-aminocyclohexanol is reacted first with N-carbethoxyphthalimide and the resulting 4-(1-phthalimidyl)cyclohexanol treated with pyridinium chlorochromate to give the desired ketone. The resultant 4-(1-phthlimidyl)cyclohexanone is then reacted with an appropriate phenylhydrazine followed by Fischer indole cyclization to prepare the corresponding 3-(1-phthalimidyl) carbazole. The phthalimide is then removed by reaction with hydrazine at a convenient point after the Fischer indole synthesis to provide compounds of the invention where $R^1=R^2=H$.

Compounds of the invention where m=0 and n=1 are 7-substituted-4-amino-10H-cyclohepta[6,7-b]indoles. These compounds are prepared substantially as described for the 6-substituted-3-amino-1,2,3,4-tetrahydro-9H-carbazoles as illustrated in Synthetic Scheme I, except that a 4-aminocycloheptanone replaces the 4-aminocyclohexanone in the synthesis. The 4-aminocycloheptanones required for the synthesis of compounds of the present invention may be prepared as described in Synthetic Scheme IV. $R^1$ and $R^2$ are independently $C_1$–$C_6$ alkyl or benzyl, or together with the nitrogen form the phthalimide moiety.

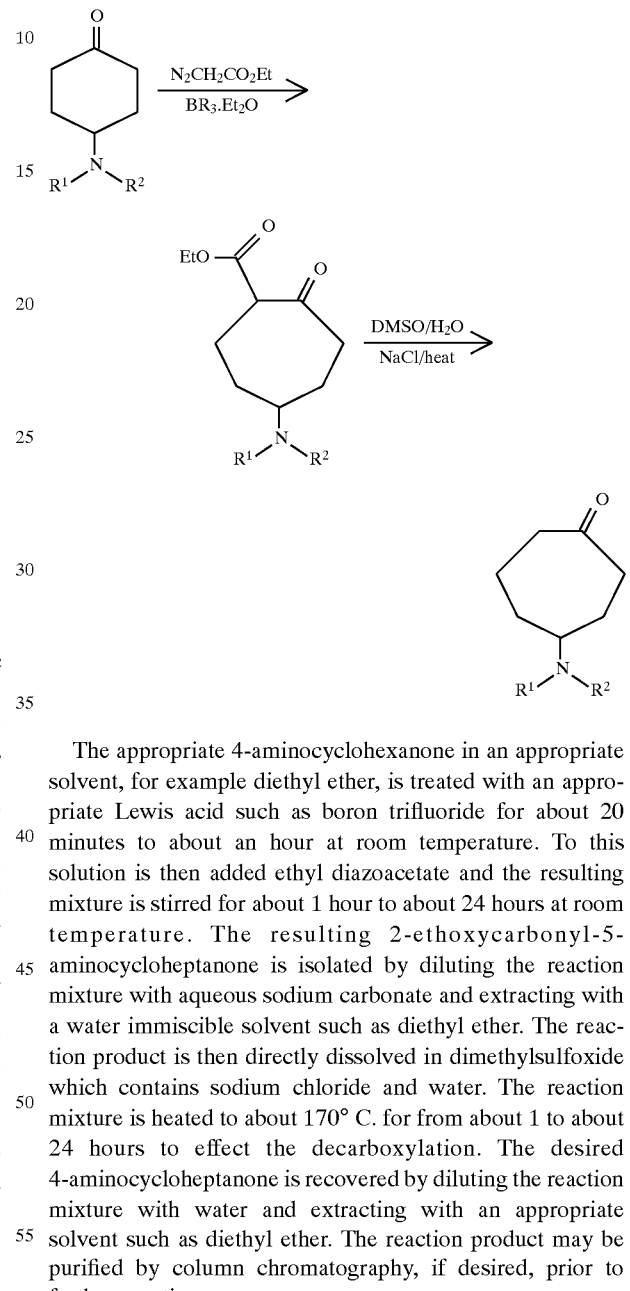

Synthetic Scheme IV

The appropriate 4-aminocyclohexanone in an appropriate solvent, for example diethyl ether, is treated with an appropriate Lewis acid such as boron trifluoride for about 20 minutes to about an hour at room temperature. To this solution is then added ethyl diazoacetate and the resulting mixture is stirred for about 1 hour to about 24 hours at room temperature. The resulting 2-ethoxycarbonyl-5-aminocycloheptanone is isolated by diluting the reaction mixture with aqueous sodium carbonate and extracting with a water immiscible solvent such as diethyl ether. The reaction product is then directly dissolved in dimethylsulfoxide which contains sodium chloride and water. The reaction mixture is heated to about 170° C. for from about 1 to about 24 hours to effect the decarboxylation. The desired 4-aminocycloheptanone is recovered by diluting the reaction mixture with water and extracting with an appropriate solvent such as diethyl ether. The reaction product may be purified by column chromatography, if desired, prior to further reaction.

After reaction with an appropriate phenylhydrazine, the corresponding 4-aminocycloheptanonephenylhydrazone is subjected to the same Fischer indole cyclization conditions as described above. The asymmetry in the cycloheptanone, however, leads to the production of the following two isomers:

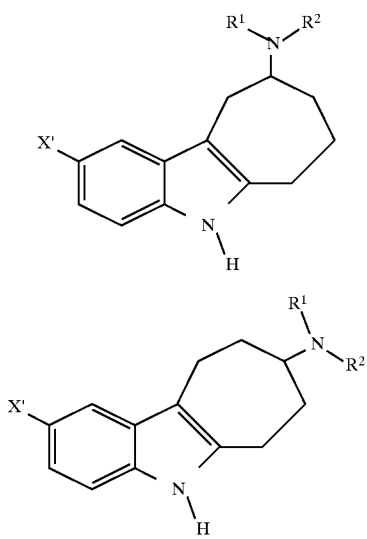

ISOMER A

ISOMER B

Isomers A and B may be separated by crystallization or chromatography at any convenient point in the synthesis of the compounds of the invention.

Compounds of the invention where m=1 and n=1 are conveniently prepared by the procedure described in Synthetic Scheme V. $R^1$ and $R^2$ are independently $C_1$–$C_6$ alkyl or benzyl; and X' is benzyloxy or bromo.

viously. The resultant ethyl 3-carboxy-6-substituted-9H-1,2,3,4-tetrahydrocarbazole is subjected to basic ester hydrolysis conditions and the carboxylate subsequently protonated to give the corresponding carboxylic acid. The carboxylic acid is coupled to an amine of structure $HNR^1R^2$ under any of the amide forming conditions described earlier. The resulting amide is reduced with an appropriate hydride reducing agent, such as lithium aluminum hydride or diborane, under standard conditions to give the corresponding N-substituted-3-methylamino-6-substituted-9H-1,2,3,4-tetrahydrocarbazole. This product may be used as is, or may be purified by chromatography or crystallization as desired prior to further reaction.

The skilled artisan will appreciate that ethyl 4-carboxycyclohexanone may undergo the ring expansion described above to give the corresponding ethyl 4-carboxycycloheptanone. This substrate may then be subjected to the same sequence of steps described in Synthetic Scheme V to give the corresponding 3- and 4-aminomethylcyclohepta[7,6-b]indoles. The isomers may be separated at any convenient point in the synthesis after the Fischer indolization step.

Compounds of the invention where X is bromo are useful intermediates for the introduction of a variety of substituents into the 6- or 7-position of the corresponding tetrahydrocarbazole or cyclohepta[7,6-b]indole nuclei respectively. Prior to manipulation of the bromo substituent, however, the Synthetic Scheme V

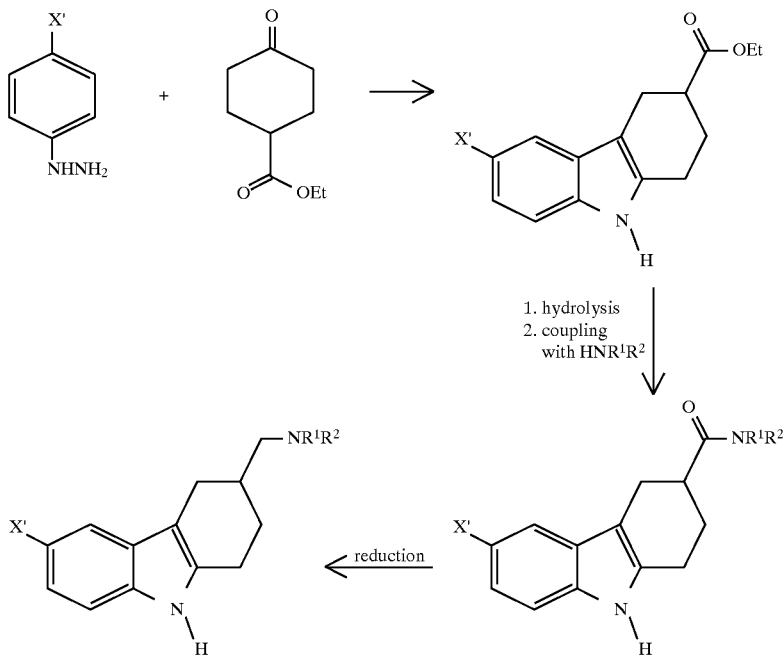

The appropriate phenylhydrazine and ethyl cyclohexanone-4-carboxylate are condensed together to prepare the corresponding phenylhydrazone which is then subjected to Fischer indolization conditions as described previously.

indole nitrogen must first be protected as illustrated in Synthetic Scheme VI. $R^1$ and $R^2$ are $C_1$–$C_6$ alkyl or benzyl; and Ar is phenyl or 2,4,6-triisopropylphenyl.

Synthetic Scheme VI

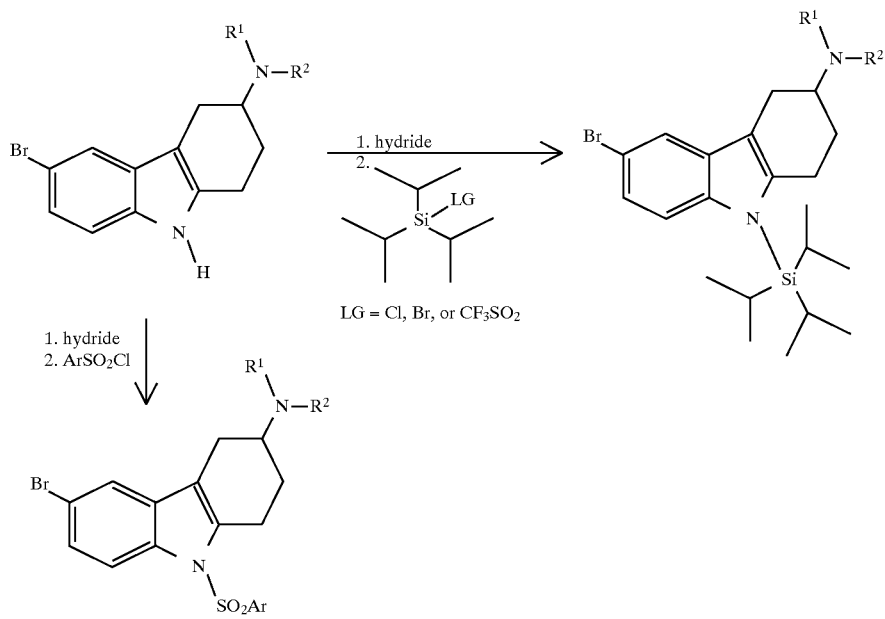

A solution of the starting material in an a suitable solvent, such as tetrahydrofuran or diethyl ether, are added to a suspension of an alkali metal hydride, preferably potassium hydride, in the same solvent. The deprotonation is performed at from about −10° C. to about ambient temperature for about an hour. To this solution is then added an appropriate arylsulfonyl chloride, triisopropylsilyl halide, or triisopropylsilyl triflate and the reaction is allowed to proceed for from about 1 to 24 hours. The indole nitrogen protected derivative is isolated by treating the reaction mixture with ice to decompose any unreacted hydride, diluting the reaction mixture with water, and then extracting the product with a water immiscible solvent such as dichloromethane, diethyl ether or ethyl acetate. The isolated product may be used as recovered for further reactions, or purified by crystallization or chromatography as desired. The bromo substituted substrate so protected may be used to provide compounds of the invention where X is $R^6C(O)$— as described in Synthetic Scheme VII. $R^1$ and $R^2$ are $C_1$–$C_6$ alkyl or benzyl; and Z is phenylsulfonyl, 2,4,6-triisopropylphenylsulfonyl, or triisopropylsilyl; and $R^6$ is as previously defined.

Synthetic Scheme VII

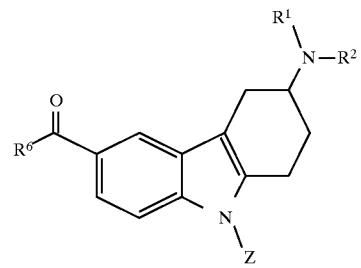

-continued
Synthetic Scheme VII

A solution of the bromo compound in an appropriate solvent, such as tetrahydrofuran or diethyl ether, is treated with an alkyllithium, such as n-butyl- or t-butyllithium, at a temperature of about −70° C. for about an hour to effect a hologen-metal exchange. The resultant anion solution is added to a solution of the appropriate N-methyl-N-methoxyamide in an appropriate solvent, such as tetrahydrofuran or diethyl ether, at a temperature of about −70° C. The reaction mixture is then allowed to warm gradually to room temperature over from about 1 hour to about 24 hours. The resulting product is isolated by diluting the reaction mixture with water or aqueous ammonium chloride and extracting with a water immiscible solvent such as dichloromethane. The product may be further purified by chromatography or recrystallization as necessary.

The N-methyl-N-methoxyamides are conveniently prepared by reacting a carboxylic acid of formula $R^6$—$CO_2H$ with oxalyl chloride or thionyl chloride under standard conditions to prepare the corresponding acid chloride. This acid chloride is then treated with N-methoxymethylamine to prepare the required amide.

Alternatively, the compounds where X is $R^6C(O)$— may be prepared by the procedure illustrated in Synthetic Scheme VIII. $R^1$ and $R^2$ are $C_1$–$C_6$ alkyl or benzyl; and Z is phenylsulfonyl, 2,4,6-triisopropylphenylsulfonyl, or triisopropylsilyl; and $R^6$ is as previously defined.

Synthetic Scheme VIII

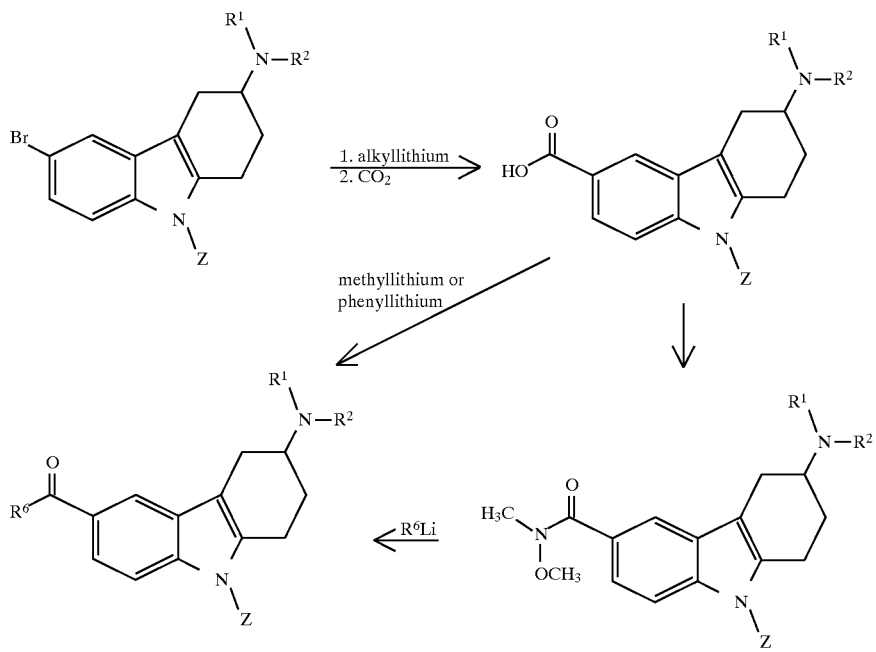

The anion solution is prepared as previously described and is then saturated with carbon dioxide to prepare the corresponding carboxylic acid. This is acid may then be treated directed with an alkyllithium, such as methyllithium, to prepare compounds where $R^6$ is $C_1$–$C_4$ alkyl. Alternatively, the carboxylic acid may be converted to its corresponding N-methyl-N-methoxyamide using the procedures previously described. This amide is then treated with a compound of formula $R^6Li$ to give the desired compound. Compounds of formula $R^6Li$ are commercially available or may be prepared by halogen-metal exchange from an $R^6$-halide under the conditions previously described.

The final step in the sequence requires deprotection of the indolic nitrogen to give the compounds of the invention as illustrated in Synthetic Scheme IX. $R^1$ and $R^2$ are independently hydrogen, $C_1$–$C_6$ alkyl or benzyl; Z is phenylsulfonyl, 2,4,6-triisopropylphenylsulfonyl, or triisopropylsilyl; and $R^6$ is as previously defined.

Synthetic Scheme IX

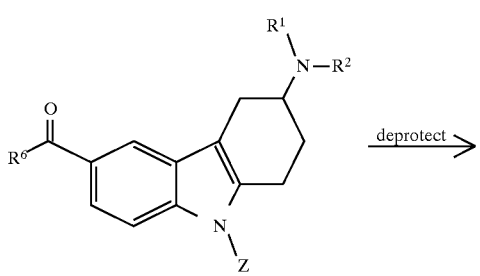

-continued
Synthetic Scheme IX

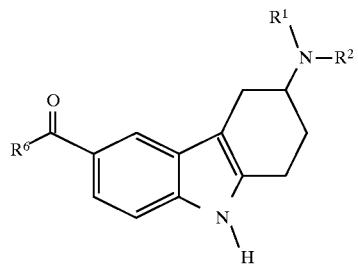

When Z is arylsulfonyl, the protecting group may be removed by basic hydrolysis in a lower alkanol such as methanol or ethanol. When Z is triisopropylsilyl, deprotection is conveniently effected by treatment with a fluoride anion reagent, preferably tetrabutylammonium fluoride, under standard conditions.

Compounds of the invention where X is $R^6C(O)$— and $R^1$ and $R^2$ are independently hydrogen are available by subjecting the corresponding 3-benzylamino compounds to catalytic hydrogenation conditions over a precious metal catalyst, such as palladium or platinum on carbon, or over Raney nickel. These reactions are typically performed in a lower alkanol or tetrahydrofuran at room temperature to about 60° C., for from about 1 hour to 24 hours, at a hydrogen pressure of about 60 p.s.i. This hydrogenolysis may be performed before or after the deprotection of the indole nitrogen as desired. Additionally, compounds of the invention where X is —OH are prepared by hydrogenolysis of the corresponding benzyl ether under the same conditions as described above.

The protected bromo compounds described in Synthetic Scheme VI are also useful for the preparation of the corresponding amine derivatives as described in Synthetic Scheme X. $R^1$ and $R^2$ are independently $C_1$–$C_6$ alkyl or benzyl; and Z is phenylsulfonyl, 2,4,6-triisopropylphenylsulfonyl, or triisopropylsilyl.

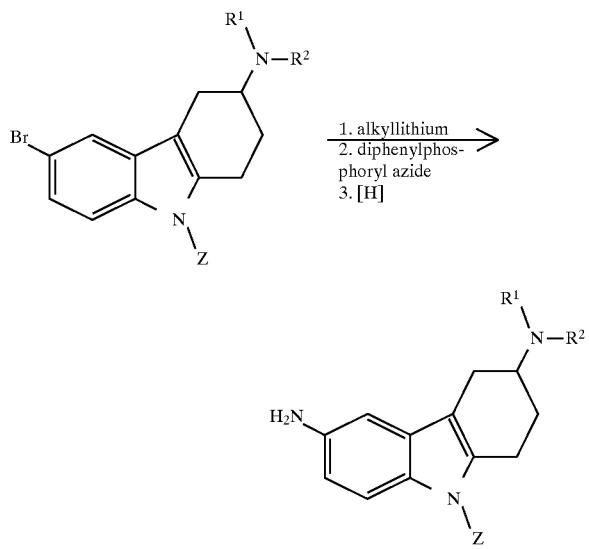

The anion is prepared according to the procedure previously described. The anion solution is then added to a solution of diphenylphosporyl azide in an appropriate solvent, such as such as tetrahydrofuran or diethyl ether, at a temperature of about −70° C. The reaction mixture is maintained at this temperature for about two hours and is then treated with an appropriate hydride reducing agent, such as sodium bis(2-methoxyethoxy)aluminum hydride in toluene. The resulting reaction mixture is allowed to warm to room temperature over about an hour. The amine product is isolated by first treating the reaction mixture with ice to destroy any excess hydride reagent, filtering any solid which has formed, diluting the filtrate with water and extracting the product into a water immiscible solvent such as dichloromethane. The amine product prepared by this procedure is useful for preparation of compounds where X is $R^3C(O)NH$—, $R^4NHC(Y)NH$—, $R^5OC(O)NH$—, or $R^7SO_2NH$— by the reaction conditions described previously for the functionalization of nitroanilines in Synthetic Scheme II. Alternatively, compounds where X is $R^3C(O)NH$— or $R^5OC(O)NH$— may be subjected to acidic or basic hydrolysis conditions to prepare the corresponding amine, which may then be converted to other compounds of the invention.

Compounds where either or both of $R^1$ or $R^2$ are hydrogen may be further functionalized to prepare other compounds of the invention by reductive alkylation. Under these conditions the primary or secondary amine is reacted with an appropriate aldehyde or ketone to prepare the corresponding imine or enamine. The imine or enamine is then reduced to the desired compound by catalytic hydrogenation or by reduction with an appropriate hydride reducing reagent in the presence of an acid. Preferably, the transformation is performed by direct alkylation as illustrated in Synthetic Scheme XI. $R^1$ is hydrogen or $C_1$–$C_6$ alkyl; $R^{2*}$ is $C_1$–$C_6$ alkyl or arylethyl; and X and arylethyl are as previously defined.

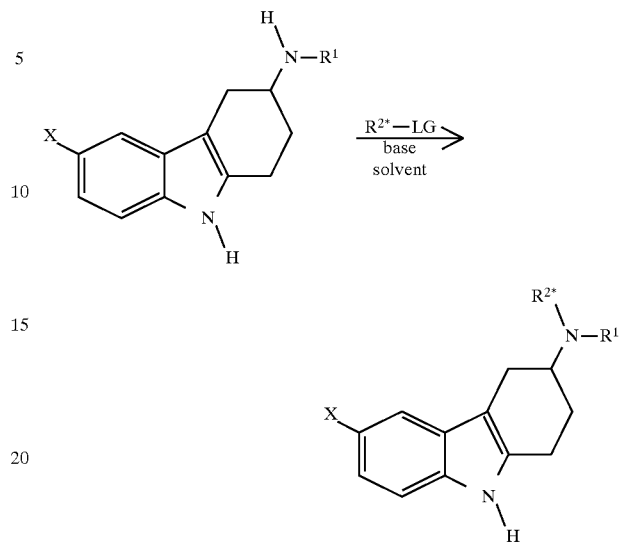

The starting amine and a base are combined in the reaction solvent followed by the addition of the alkylating agent. The reaction solvent may be any non-reactive solvent typically used for alkylations of this type such as acetonitrile, dimethylformamide or N-methyl-2-pyrrolidinone, limited by the solubility of the substrates. The base must be sufficiently basic to neutralize the acid generated during the progress of the reaction but not so basic as to deprotonate other sites in the substrate giving rise to other products. Additionally, the base must not compete to any great extent with the substrate for the alkylating agent. Bases typically used for these reactions are sodium carbonate or potassium carbonate. The reaction mixture is typically stirred at room temperature to 80° C., for about 8 hours to 3 days. The alkylated products are isolated by concentration of the reaction mixture under reduced pressure followed by partitioning of the resultant residue between water and a suitable organic solvent such as ethyl acetate, diethyl ether, dichloromethane, ethylene chloride, chloroform or carbon tetrachloride. The isolated product may be purified by chromatography, crystallization from a suitable solvent, salt formation or a combination of these techniques.

The leaving group (LG) of the alkylating agents may be chloro, bromo, iodo, methanesulfonyloxy, trifluoromethanesulfonyloxy, 2,2,2-trifluoroethanesulfonyloxy, benzenesulfonyloxy, p-bromobenzenesulfonyloxy, p-nitrobenzenesulfonyloxy or p-toluenesulfonyloxy, all of which are useful for the preparation of compounds of this invention. The specific alkylating agent employed is determined by its commercial availability or a convenient synthesis from commercially available starting materials. The preferred alkylating agents for synthesis of compounds of this invention are selected from those where the leaving group is chloro, bromo, iodo or methanesulfonyloxy. Alkylating agents where the leaving group is chloro are prepared from the corresponding alcohol by standard methods, preferably by treating the alcohol with neat thionyl chloride at ambient temperature. Alkylating agents where the leaving group is methanesulfonyloxy are prepared from the corresponding alcohols as described below.

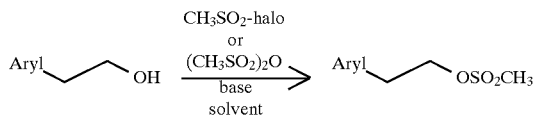

The alcohol is dissolved in a suitable anhydrous solvent such as tetrahydrofuran, diethyl ether, p-dioxane or acetonitrile which contains the base. The base must be sufficiently basic to neutralize the acid generated during the progress of the reaction but not so basic as to deprotonate other sites in the substrate giving rise to other products. Additionally, the base must not compete to any great extent with the substrate for the sulfonating reagent and must have sufficient solubility in the reaction solvent. Bases typically used in these reactions are tertiary amines such as pyridine, triethylamine or N-methylmorpholine. To the reaction mixture is then added the sulfonating reagent with cooling. The sulfonating reagent may be a methanesulfonyl halide such as the chloride, or methanesulfonic anhydride. The reaction mixture is allowed to react from 1 hour to 24 hours at ambient temperature. The product is isolated by concentrating the reaction mixture under reduced pressure followed by partitioning the residue between water and an appropriate organic solvent such as dichloromethane, ethylene chloride, chloroform or carbon tetrachloride. The isolated product is used directly in the alkylation step.

The starting alcohols required for the synthesis of compounds of this invention are either commercially available or may be prepared by employing well established synthetic methodology. A general scheme for the synthesis of a number of the required alcohols is described below.

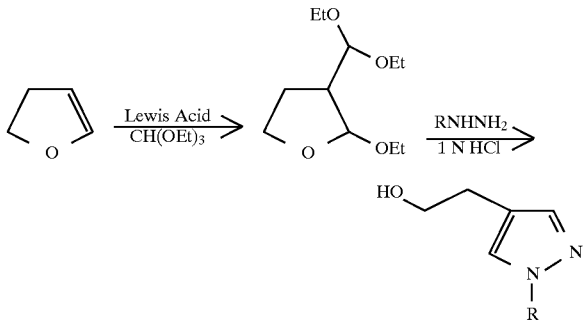

4,5-Dihydrofuran or 3,4-dihydro-2H-pyran is treated with triethylorthoformate in the presence of a Lewis acid, preferably boron trifluoride diethyl etherate, for from 1 to 4 days at ambient temperature. After treating the reaction mixture with an anhydrous base such as potassium carbonate the intermediate diacetal is distilled from the reaction mixture. This diacetal is now treated with an appropriate hydrazine, typically commercially available or synthesized by standard techniques, in aqueous acid at reflux for 4–24 hours. The product is recovered by treatment of the reaction mixture with base and extraction of the base into methylene chloride. The alcohol so recovered is suitable for use without further purification. When R is hydrogen, the alcohol can be further modified by direct alkylation of one of the pyrazole nitrogens as described below.

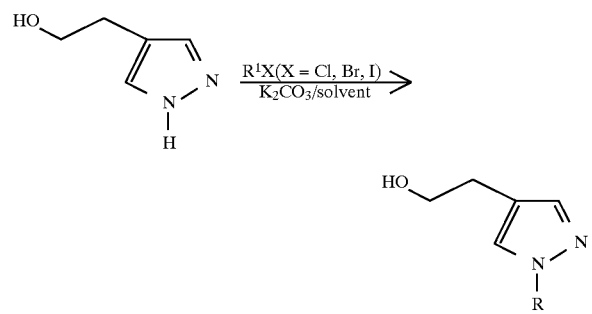

The alkylation is performed in a suitable solvent, typically dimethylformamide, acetonitrile or acetone, with potassium carbonate and the desired alkylating agent. The alkylating agent is a lower alkyl halide, preferably the bromide or iodide. The reaction is performed at ambient to reflux temperature for 1 hour to 3 days.

The compounds of the present invention possess a chiral center, and as such exist as racemic mixtures or individual enantiomers. As stated above, racemates and the individual enantiomers are all part of the present invention. The individual enantiomers may be resolved by fractional crystallization of salts of the racemic bases and enantiomerically pure acids, for example, ditolyltartaric acid. Alternatively, the individual enantiomers may be prepared by the use of a chiral auxiliary during the preparation of the compound as described in the following Synthetic Scheme XII. X is bromo, benzyloxy, nitro, $R^3C(O)NH-$, $R^4NHC(Y)NH-$, $R^5OC(O)NH-$, or $R^7SO_2NH-$; and Y, $R^3$, $R^4$, $R^5$ and $R^7$ are as previously defined.

Synthetic Scheme XII

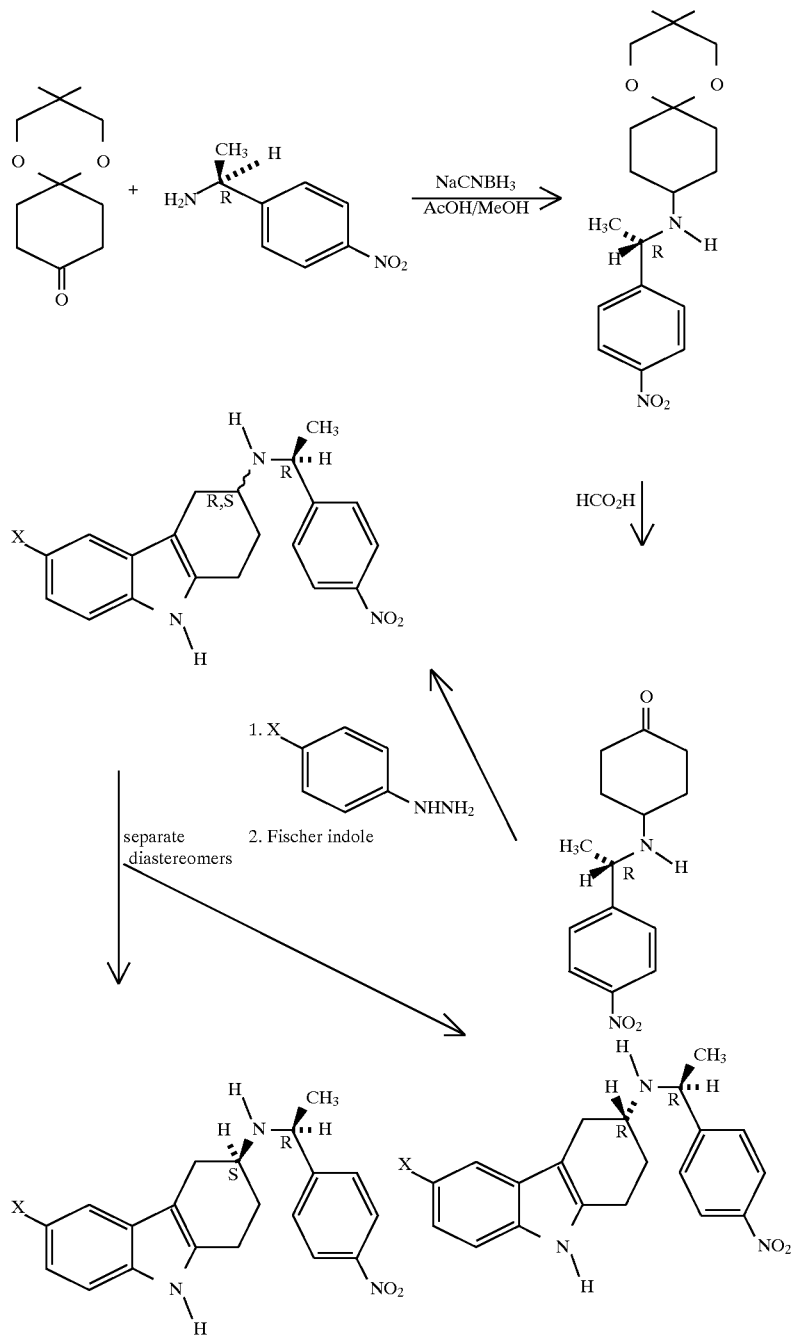

1,4-cyclohexanedione mono-(2,2-dimethylpropane-1,3-diol)ketal is reductively aminated under standard conditions with an enantiomer of a-methyl-(4-nitrophenyl)ethylamine (Synthetic Scheme XII illustrates the use of the R-(+)-enantiomer). The ketal is removed as described previously and the resulting aminocyclohexanone is subjected to the reaction conditions described for Synthetic Scheme I to give a diastereomeric mixture. The diastereomers are then separated by chromatography or fractional crystallization. The amine may then be treated, if desired, with an appropriate alkylating agent, for example an appropriate alkyl halide, to prepare the corresponding quaternary salt prior to cleavage of the a-methyl-(4-nitrophenyl)ethyl moiety.

Cleavage of the a-methyl-(4-nitrophenyl)ethyl moiety is achieved by reduction of the 4-nitro group followed by acid catalyzed solvolysis of the resulting a-methyl-(4-aminophenyl)ethyl moiety. Reduction of the nitro group can be accomplished by a wide range of reducing agents including, for example, titanium tetrachloride, lithium aluminum hydride, or zinc/acetic acid, or by catalytic hydrogenation. Solvolytic cleavage takes place when the monohydrochloride (or other monobasic salt) of the reduction product is treated with water or an alcohol at room temperature or, in some instances, at elevated temperatures. A particularly convenient condition for removing the a-methyl-(4-nitrophenyl)ethyl moiety is hydrogenation of the amine monohydrochloride in methanol over a platinum catalyst.

The reactions as illustrated in Synthetic Schemes VI–XII are for the compounds of the invention which are carbazoles. The skilled artisan, however, will appreciate that the chemistry illustrated is applicable to the other classes of compounds of the invention as well. The skilled artisan will also appreciate that the order in which the steps are performed to prepare the compounds of the present invention are not important in many cases.

Preparation I 6-bromo-3-dimethylamino-9-triisopropylsilyl-1,2,3,
4-tetrahydro-9H-carbazole 4-dimethylaminocyclohexanone(2,2-dimethylpropane-1,3-diol)ketal To a solution of 25.0 gm (554.6 mMol) dimethylamine in 500 mL methanol were added 50.0 gm (252.2 mMol) 1,4-cyclohexanedione mono-2,2-dimethylpropane-1,3-diol ketal and the reaction mixture was allowed to stir for 2 hours at room temperature. To this solution were then gradually added 31.69 gm (504.3 mMol) sodium cyanoborohydride. Once this addition was complete, acetic acid was added to adjust the mixture to a pH of about 6. The pH was monitored periodically and acetic acid additions continued to maintain the pH at about 6. When the addition of acetic acid no longer resulted in gas evolution, the reaction mixture was allowed to stir at room temperature for 18 hours. The reaction mixture was then concentrated under reduced pressure to a volume of about 100 mL and was then partitioned between 1N sodium hydroxide and dichloromethane. The remaining aqueous phase was treated with saturated aqueous sodium chloride and was again extracted with dichloromethane. These organic phases were combined, dried over sodium sulfate and concentrated under reduced pressure to give 40.15 gm (70%) of the desired compound as a yellow oil.

MS(m/e): 228(M+1)

4-dimethylaminocyclohexanone

A solution of 18.4 gm (81 mMol) 4-dimethylaminocyclohexanone(2,2-dimethylpropane-1,3-diol)ketal in 250 mL 90% formic acid were heated at reflux for 3 hours. The reaction mixture was then stirred at room temperature for 3 days. The reaction mixture was then diluted with 250 mL water and was concentrated to a volume of about 250 mL on a rotary evaporator. The dilution/concentration sequence was then repeated two more times. The residue was then further concentrated to a volume of about 50 mL, made basic with 5N sodium hydroxide and extracted with dichloromethane. The organic phases were combined, dried over sodium sulfate and concentrated under reduced pressure to give 11.8 gm (100%) of the desired compound as a yellow oil.

MS(m/e): 141 (M+)

NMR(CDCl$_3$): d 2.50 (m, 2H), 2.28 (m, 2H), 2.28 (m, 6H), 2.01 (m, 2H) , 1.80 (m, 2H).

4-dimethylaminocyclohexanone 4-bromophenylhydrazone

To a mixture of 6.0 gm (42.0 mMol) 4-dimethylaminocyclohexanone and 9.5 gm (42.0 mMol) 4-bromophenylhydrazine hydrochloride in 100 mL ethanol were added 3.4 mL (42 mMol) pyridine. The resultant mixture was then heated at reflux for 2 hours and then stirred at ambient temperature for 18 hours. The reaction mixture was then treated with aqueous potassium carbonate and extracted well with dichloromethane. The organic phases were combined, dried over sodium sulfate and concentrated under reduced pressure. The resultant residue was treated with toluene and concentrated again under reduced pressure to give 11.3 gm (87%) of the desired compound.

6-bromo-3-(dimethyl)amino-1,2,3,4-tetrahydro-9H-carbazole hydrochloride

A solution of 11.3 gm (36.4 mMol) 4-dimethylaminocyclohexanone 4-bromophenylhydrazone in 250 mL 4M ethanolic hydrogen chloride were heated to reflux under nitrogen for 3 hours. The reaction mixture was allowed to cool to room temperature and was then concentrated under reduced pressure. The residual paste was dissolved in 200 mL water and to this solution were then added 50 mL 6M hydrochloric acid. The mixture was cooled to 0° C. for 18 hours. The desired product which had crystallized was filtered and dried to give 8.66 gm (72%).

Silylation 8.66 gm (26.2 mMol) 6-bromo-3-(dimethyl)amino-1,2,3,4-tetrahydro-9H-carbazole hydrochloride were partitioned between 1N sodium hydroxide and dichloromethane. The organic phase was dried over sodium sulfate and concentrated under reduced pressure. The residue was dissolved in 50 mL tetrahydrofuran and the resultant solution was added to a suspension of 8.0 gm (40 mMol) potassium hydride (20% in mineral oil) in 100 mL tetrahydrofuran cooled to about 0° C. The resultant mixture was stirred for an hour at this temperature and then to it were added 8.0 mL (30 mMol) triisopropylsilyltriflate and the mixture was allowed to warm gradually to room temperature. After 18 hours the reaction mixture was treated with ice to decompose excess potassium hydride. Once all of the hydride had been destroyed, the reaction mixture was diluted with 200 mL of water and was then extracted well with dichloromethane. The organic phases were combined, dried over sodium sulfate and concentrated under reduced pressure. The residual oil was subjected to silica gel chromatography, eluting sequentially with toluene, 9:1 toluene:ethyl acetate, 4:1 toluene:ethyl acetate, 1:1 toluene:ethyl acetate, and ethyl acetate. The ethyl acetate fractions were combined and concentrated under reduced pressure to give 7.08 gm (60%) of the title compound as a solid.

m.p.=92°–93° C.

NMR(CDCl$_3$): d 7.52 (d, 1H), 7.39 (dd, 1H), 7.13 (d, 1H), 3.04 (br dd, 1H), 2.88 (m, 2H), 2.70 (m, 1H), 2.58 (dd, 1H), 2.41 (s, 6H), 2.20 (d, 1H), 1.78 (m, 3H), 1.70 (m, 1H), 1.14 (m, 18H).

All N-methyl-N-methoxyamides useful for the preparation of the compounds of this invention are available by substituting an appropriate carboxylic acid for 4-chlorobenzoic acid in the following procedure.

Preparation II 4-chloro-N-methyl-N-methoxybenzamide

To a solution 11.38 gm (116.7 mMol) N-methoxy-N-methyl amine hydrochloride in 700 mL 1N sodium hydroxide was added a solution of 18.56 gm (106.04 mMol) 4-chlorobenzoyl chloride in 200 mL dichloromethane and the mixture was stirred at ambient temperature. After 18 hours the phases were separated and the remaining aqueous was extracted well with dichloromethane. All organic phases are combined, dried over sodium sulfate and concentrated under reduced pressure to give 27.9 gm (95%) of the title compound as a clear oil.

MS(m/e): 199(M+)

IR: 3011, 2974, 2938, 1634 cm$^{-1}$

Preparation III 6-amino-3-(dimethyl)amino-1,2,3,4-tetrahydro-9H-carbazole hydrochloride 6-(t-butoxycarbonyl)amino-3-(dimethyl)amino-9-trimethylsilyl-1,2,3,4-tetrahydro-9H-carbazole To a solution of 0.898 gm (2.0 mMol) 6-bromo-3-(dimethyl)amino-9-triisopropylsilyl-1,2,3,4-tetrahydro-9H-carbazole in 20 mL tetrahydrofuran at −70° C. were added 1.56 mL (2.2 mMol) n-butyllithium (1.41M in hexane). The solution was allowed to stir at this temperature for 45 minutes and then it was siphoned over 15 minutes into a solution of 0.50 mL (2.3 mMol) diphenylphosphoryl azide in 20 mL tetrahydrofuran at −70° C. The wine red solution was maintained at −70° C. for 2 hours at which point the reaction mixture was treated with 2.5 mL (8.9 mMol) sodium bis(2-methoxyethoxy)aluminum hydride (65% in toluene). The reaction mixture was allowed to warm to 0° C. during which time gas evolution was observed and the reaction mixture became pale yellow. After 30 minutes at 0° C. the reaction mixture was allowed to warm to room temperature. After 30 minutes at room temperature the reaction mixture was again cooled to 0° C. and was cautiously treated with ice to decompose excess hydride. The reaction mixture was then filtered to remove the precipitate that had formed and the precipitate was washed thoroughly with diethyl ether. The combined filtrates were washed sequentially with dilute aqueous sodium hydroxide and saturated aqueous sodium chloride, dried over sodium sulfate and concentrated under reduced pressure to a viscous oil. This oil was then dissolved in 10 mL dichloromethane and to it were added 0.50 gm (2.3 mMol) di-(t-butyl)carbonate. The resulting solution was then stirred for 18 hours at room temperature. The reaction mixture was then concentrated under reduced pressure. The residue was then dissolved in toluene and concentrated under reduced pressure to remove and residual t-butanol. The residue was then subjected to column chromatography, eluting with a gradient of chloroform (2–8% 95:5 methanol:ammonium hydroxide) to give 0.45 gm (46%) of the desired compound as a colorless glass.

MS(m/e): 486(M$^+$)

Calculated for $C_{28}H_{47}N_3OSi$: Theory: C, 69.23; H, 9.75; N, 8.65. Found: C, 68.93; H, 9.50; N, 8.44.

6-(t-butoxycarbonyl)amino-3-(dimethyl)amino-1,2,3,4-tetrahydro-9H-carbazole

To a solution of 0.44 gm (0.91 mMol) 6-(t-butoxycarbonyl)amino-3-(dimethyl)amino-9-triisopropylsilyl-1,2,3,4-tetrahydro-9H-carbazole in 10 mL tetrahydrofuran at 0° C. were added 0.30 gm boric acid followed by 1.5 mL 1M aqueous tetrabutylammonium fluoride. After 3 hours the reaction mixture was added to dilute aqueous tartaric acid and the resulting mixture extracted several times with dichloromethane. The remaining aqueous phase was made basic with dilute aqueous sodium hydroxide and extracted well with dichloromethane. This organic phase was dried over sodium sulfate and concentrated under reduced pressure. This residue was subjected to radial chromatography (2 mm silica gel), eluting with 96:4 chloroform::methanol containing 5% ammonium hydroxide. Fractions shown to contain product were combined and concentrated under reduced pressure to give 0.246 gm (83%) of the desired product.

MS(m/e): 330(M$^+$)

Deprotection of 6-amino group 0.385 gm (1.17 mMol) 6-(t-butoxycarbonyl)amino-3-(dimethyl)amino-1,2,3,4-tetrahydro-9H-carbazole were dissolved in 10 mL trifluoroacetic acid and the mixture allowed to stir for 1 hour at room temperature. The reaction mixture was then concentrated under reduced pressure and the residue dissolved in dichloromethane. The organic phase was washed with aqueous potassium carbonate, dried over sodium sulfate and concentrated under reduced pressure to give 0.261 gm (97%) of the title compound as a grayish-tan foam.

The phenylhydrazines required for the synthesis of the compounds of the invention may be prepared by the procedure described in detail in Preparation IV.

Preparation IV 4-(4-fluorobenzoyl)aminophenylhydrazine
4-(4-fluorobenzoyl)aminonitrobenzene To a suspension of 30.0 gm (0.217 mole) 4-nitroaniline in 225 mL dichloromethane were added 17.57 mL (0.217 mole) pyridine. The suspension was cooled to 0° C. and then 25.66 mL (0.217 mole) 4-fluorobenzoyl chloride were added slowly. Within 15 minutes the reaction mixture became homogeneous and was allowed to warm to room temperature. After an hour an additional 2.56 mL (21.7 mMol) 4-fluorobenzoyl chloride and 1.75 mL (21.7 mMol) pyridine were added and the reaction continued at room temperature for an additional hour. The reaction mixture was then washed with 200 mL water at which point a precipitate formed. The solid was filtered, washed with 100 mL hexane, washed with 200 mL water and dried under reduced pressure at 60° C. to give 56.6 gm (100%) of the desired compound.

4-(4-fluorobenzoyl)aminoaniline

To a solution of 56.6 gm (0.217 mole) 4-(4-fluorobenzoyl)aminonitrobenzene in 875 mL tetrahydrofuran were added 5.7 gm 5% platinum on carbon. The reaction mixture was hydrogenated at room temperature for 18 hours at initial hydrogen pressure of 60 p.s.i. The reaction mixture was then filtered and the filtrate concentrated under reduced pressure to give 49.3 gm (98.5%) of the desired compound.

Diazotization/Reduction

To a suspension of 1.00 gm (4.34 mMol) 4-(4-fluorobenzoyl)aminoaniline in 4.25 mL concentrated hydrochloric acid at 0C. were added very slowly a solution of 0.329 gm (4.77 mMol) sodium nitrite in 3.2 mL water. The mixture was stirred at this temperature for 10 minutes and was then cannulated into a solution of 3.917 gm (17.36 mMol) stannous chloride dihydrate in 4.25 mL concentrated hydrochloric acid at 0° C. The resultant suspension was stirred at this temperature for 1 hour. The reaction was then treated with 50 mL 5N sodium hydroxide and was extracted well with ethyl acetate. The organic extracts were combined, dried over magnesium sulfate and concentrated under reduced pressure to give 0.90 gm (82%) of the title compound.

MS(m/e): 245(M$^+$)

The reaction described in Preparation V is representative of the Fischer Indole conditions for the preparation of the compounds of the invention.

Preparation V 6-(4-fluorobenzoyl)amino-3-(1-phthalimidiyl)-1,2,3,4-tetrahydro-9H-carbazole A suspension of 0.28 gm (1.11 mMol) 4-(1-phthalimidyl) cyclohexanone and 0.256 gm (1.05 mMol) 4-(4-fluorobenzoyl)aminophenylhydrazine in 8.0 mL ethanol were heated to reflux for 1 hour. To this mixture were then added 10 drops concentrated hydrochloric acid. The resulting mixture was heated to reflux for 18 hours. The reaction mixture was then cooled to room temperature and was diluted with 10 mL diethyl ether followed by 30 mL hexanes. The resulting solid was filtered and dried under vacuum to give 0.288 gm of the title compound. The filtrate was concentrated under reduced pressure and the residue subjected to silica gel chromatography, eluting with 40:60:5 ethyl acetate:hexane:methanol, to give an additional 0.128 gm of product. Total yield: 0.416 gm (87%).

Preparation VI

4-(1-phthalimidyl)cycloheptanone

To a stirred solution of 5.00 gm (20.55 mMol) 4-(1-phthalimidyl)cyclohexanone in 30 mL diethyl ether were added 3.79 mL (30.8 mMol) boron trifluoride ethereate. After stirring for 20 minutes at room temperature, 3.24 mL (30.8 mMol) ethyl diazoacetate were added dropwise. The resultant solution was stirred for 16 hours at room temperature. The reaction mixture was diluted with saturated aqueous sodium carbonate and was then extracted with diethyl ether. The combined organic extracts were dried over sodium sulfate and concentrated under reduced pressure. The residue was dissolved in 15 mL dimethylsulfoxide. To this wolution was added 1.3 mL water and 1.5 gm sodium chloride. The resulting mixture was heated at 170° C. for 7 hours. The reaction mixture was then cooled, poured into 150 mL water and extracted well with diethyl ether. The combined organic phases were washed sequentially with water and saturated aqueous sodium chloride, dried over sodium sulfate and concentrated under reduced pressure. The residue was subjected to silica gel chromatography, eluting with 6:4 hexane:ethyl acetate. Fractions shown to contain product were combined and concentrated under reduced pressure to give 4.17 gm (79%) of the title compound.

MS(m/e): 257(M$^+$)

Preparation VII

7-(benzyloxycarbonyl)amino-3- and 4-(1-phthalimidyl)cyclohepta[7,6-b]indole

A suspension of 1.09 gm (4,25 mMol) 4-(1-phthalimidyl)cycloheptanone and 1.60 gm (6.2 mMol) 4-(benzyloxycarbonyl)aminophenylhydrazine in 40.0 mL ethanol were heated to reflux for 1 hour. To this mixture were then added 0.2 mL concentrated hydrochloric acid. The resulting mixture was heated to reflux for 18 hours. The reaction mixture was then concentrated under reduced pressure and the residue subjected to silica gel chromatography, eluting with 40% ethyl acetate in hexane. Fractions containing product were combined and concentrated under reduced pressure to give 1.61 gm (79%) of the title compound.

MS(m/e): 479(M$^+$)

Preparation VIII

6-benzyloxy-3-carboxy-1,2,3,4-tetrahydro-9H-carbazole

Ethyl 6-benzyloxy-3-carboxy-1,2,3,4-tetrahydro-9H-carbazole

To a suspension of 3.242 gm (12.93 mMol) 4-benzyloxyphenylhydrazine hydrochloride in 80 mL ethanol were added 1.05 mL (12.93 mMol) pyridine. The resulting mixture was heated to 50° C. for about 20 minutes and then 1.87 mL (11.75 mMol) ethyl 4-oxocyclohexanecarboxylate were added. The resulting mixture was stirred at reflux for 18 hours. The reaction mixture was then concentrated under reduced pressure and the residue partitioned between water and ethyl acetate. The organic phase was separated, washed with water, dried over magnesium sulfate and concentrated under reduced pressure. The residue was subjected to silica gel chromatography, eluting with 35% ethyl acetate in hexane. Fractions containing product were combined and concentrated under reduced pressure to give 3.38 gm (83%) of the desired compound.

Hydrolysis

To a suspension of 3.107 gm (8.9 mMol) ethyl 6-benzyloxy-3-carboxy-6-benzyloxy-1,2,3,4-tetrahydro-9H-carbazole in 100 mL 2N sodium hydroxide were added 100 mL methanol and the reaction mixture stirred at reflux for 3.5 hours. The reaction mixture was concentrated to about half volume and the pH adjusted to between 5 and 7 by the addition of concentrated hydrochloric acid. The mixture was extracted well with 4:1 dichloromethane:isopropanol. The organic phases were combined, dried over sodium sulfate and concentrated under reduced pressure to give 2.71 gm (95%) of the title compound.

Preparation IX

2-(1-methyl-1H-pyrazol-3-yl)-1-ethanol

To a mixture of 200 gm (2.85 mole) 2,3-dihydrofuran and 800 mL (4.81 mole) triethylorthoformate were added 0.8 mL (6.5 mMol) boron trifluoride diethyl etherate dropwise. After an initial exotherm the reaction mixture was allowed to stir at ambient temperature for four days. To the reaction mixture was then added 4.0 gm potassium carbonate and the reaction mixture was distilled under 6.0 mm Hg. Fractions distilling between 60° C. and 130° C. were collected to give 261.64 gm (42.1%) of a light yellow oil.

MS(m/e): 219(M$^+$)

To a solution of 87.2 gm (0.40 mole) of the previously prepared yellow oil in 787 mL 1N HCl were added 21.3 mL (0.40 mole) methyl hydrazine and the reaction mixture was stirred at reflux for four hours. The reaction mixture was cooled to ambient temperature and the volatiles were removed under reduced pressure. The residual oil was treated with 2N NaOH until basic and the aqueous extracted well with dichloromethane. The combined organic extracts were dried over sodium sulfate and concentrated under reduced pressure to give 32.15 gm (64.5%) of the title compound as a brown oil.

MS(m/e): 126(M$^+$)

$^1$H-NMR(DMSO-d6): d7.45 (s, 1H); 7.25 (s, 1H); 4.65 (t, 1H); 3.75 (s,3H); 3.55 (m, 2H); 2.55 (t, 2H).

Preparation X

2-(1-isopropyl-1H-pyrazol-3-yl)-1-ethanol

To a solution of 1.0 gm (9.0 mMol) 2-(3-pyrazolyl)-1-ethanol in 36 mL dimethylformamide were added 2.38 gm (22.5 mMol) sodium carbonate followed by the dropwise addition of a solution of 0.89 mL (9.0 mMol) 2-iodopropane in 8 mL dimethylformamide. The reaction mixture was heated to 100° C. for 18 hours. The reaction mixture was then cooled to ambient and then concentrated under reduced pressure. The residue was partitioned between water and dichloromethane. The organic phase was then washed with water followed by saturated aqueous sodium chloride and was then dried over sodium sulfate. The remaining organics were concentrated under reduced pressure to give 0.36 gm (26.0%) of the title compound as a brown oil.

$^1$H-NMR(DMSO-d6): d7.50 (s, 1H); 7.25 (s, 1H); 4.60 (t, 1H); 4.40 (m, 1H); 3.50 (m, 2H); 2.55 (t, 2H); 1.35(d, 6H).

Preparation XI

2-(4-chloro)phenyl-1-mesyloxyethane

To a stirring solution of 3.00 mL (22.16 mMol) 2-(4-chloro)phenyl-1-ethanol in 75 mL tetrahydrofuran at 0° C.

were added 4.63 mL (33.24 mMol) triethylamine followed by 1.89 mL (24.38 mMol) methanesulfonyl chloride. The reaction mixture was allowed to stir at room temperature for 18 hours. The reaction mixture was then poured into water and extracted well with ethyl acetate. The organic phases were combined, washed with water, dried over sodium sulfate and concentrated under reduced pressure to give 5.18 gm (99.6%) of the title compound.

EXAMPLE 1

6-acetyl-3-(dimethyl)amino-1,2,3,4-tetrahydro-9H-carbazole 6-carboxy-3-(dimethyl)amino-9-triisopropylsilyl-1,2,3,4-tetrahydro-9H-carbazole To a solution of 2.95 gm (6.56 mMol) 6-bromo-3-(dimethyl)amino-9-triisopropylsilyl-1,2,3,4-tetrahydro-9H-carbazole in 150 mL tetrahydrofuran at −78° C. were added 16.4 mL (26.24 mMol) t-butyllithium (1.6M in pentane). The dark solution was allowed to stir at this temperature for 1 hour and then carbon dioxide gas was bubbled through the solution until the dark color discharged to light yellow. After allowing the reaction mixture to warm to room temperature it was poured into water, the pH adjusted to about 7, and the mixture extracted well with dichloromethane. The organic phases were combined, dried over magnesium sulfate and concentrated under reduced pressure. The residue was triturated with hexane to give 2.31 gm (85%) of the desired compound as a tan foam.

IR: 3022, 2958, 2871, 1465, 1249 cm$^{-1}$

MS(m/e): 414(M$^+$)

6-acetyl-3-(dimethyl)amino-6-acetyl-9-triisopropylsilyl-1,2,3,4-tetrahydro-9H-carbazole To a solution of 2.0 gm (4.8 mMol) 6-carboxy-3-(dimethyl)amino-6-carboxy-9-triisopropylsilyl-1,2,3,4-tetrahydro-9H-carbazole in 100 mL diethyl ether at 0° C. were added 8 mL (9.6 mMol) methyllithium (1.2M in diethyl ether) over a 15 minute period. After an hour an additional 0.4 mL of the methyllithium solution were added. 0.4 mL additions were continued until all of the starting material had reacted. The reaction mixture was then allowed to warm to room temperature and to it was first added ice and then the reaction mixture was diluted with 100 mL of water. The mixture was shaken and the phases separated. The aqueous phase was twice extracted with 100 mL aliquots of fresh diethyl ether. All of the organic extracts were combined, washed with saturated aqueous sodium chloride and concentrated under reduced pressure. The residue was subjected to florisil chromatography, eluting sequentially with toluene, 9:1 toluene:ethyl acetate, 4:1 toluene:ethyl acetate, 1:1 toluene:ethyl acetate, and ethyl acetate. Fractions containing product were combined and concentrated under reduced pressure to give 1.37 gm (69%) of the desired product as a solid.

MS(m/e): 412(M$^+$)

Calculated for C$_{25}$H$_{40}$N$_2$OSi: Theory: C, 72.76; H, 9.77; N, 6.79. Found: C, 72.65; H, 9.84; N, 6.74.

Deprotection

To a solution of 1.37 m (3.29 mMol) 6-acetyl-3-(dimethyl)amino-6-acetyl-9-triisopropylsilyl-1,2,3,4-tetrahydro-9H-carbazole in 25 mL tetrahydrofuran at 0° C. containing 1.5 gm boric acid were added 5 mL 1M aqueous tetrabutylammonium fluoride. After 1 hour the reaction mixture was added to dilute aqueous tartaric acid and the resulting mixture extracted several times with dichloromethane. The remaining aqueous phase was made basic and was then extracted well with dichloromethane. This organic phase was dried over sodium sulfate and concentrated under reduced pressure to give a clear oil. This oil was crystallized from toluene 0.72 gm (86%) of the title compound as a crystalline solid.

m.p.=181°–182° C.

MS(m/e): 256(M$^+$)

Calculated for C$_{16}$H$_{20}$N$_2$O: Theory: C, 74.97; H, 7.86; N, 10.93. Found: C, 74.71; H, 7.91; N, 10.76.

EXAMPLE 2

6-benzoyl-3-(dimethyl)amino-1,2,3,4-tetrahydro-9H-carbazole 6-benzoyl-3-(dimethyl)amino-9-triisopropylsilyl-1,2,3,4-tetrahydro-9H-carbazole To a solution of 0.50 gm (1.11 mMol) 6-bromo-3-(dimethyl)amino-9-triisopropylsilyl-1,2,3,4-tetrahydro-9H-carbazole in 50 mL tetrahydrofuran at −78° C. were added 1.96 mL (3.33 mMol) t-butyllithium (1.7M in pentane) and the resulting dark solution was allowed to stir for 30 minutes. To this mixture were then added 0.20 gm (1.22 mMol) N-methyl-N-methoxybenzamide and the reaction mixture was allowed to warm to room temperature over 1 hour. The reaction mixture was then treated with 0.1N sodium hydroxide and then extracted well with chloroform. The organic phases were combined, dried over potassium carbonate and concentrated under reduced pressure to give 0.48 gm (91%) of the desired compound as a red-orange oil.

MS(m/e): 474(M$^+$)

Deprotection

To a solution of 1.00 gm (2.11 mMol) 6-benzoyl-3-(dimethyl)amino-9-triisopropylsilyl-1,2,3,4-tetrahydro-9H-carbazole in 50 mL tetrahydrofuran at 0° C. were added 5 mL tetrabutylammonium fluoride (1M in tetrahydrofuran) and 3 mL 1N boric acid. The reaction mixture was allowed to stir for 1 hour. The reaction mixture was then poured into dilute aqueous tartaric acid and the aqueous phase washed with dichloromethane. The remaining aqueous phase was made basic and was then extracted well with dichloromethane. This organic phase was dried over sodium sulfate and concentrated under reduced pressure. The residue was subjected to silica gel chromatography, eluting with dichloromethane containing from 0 to 20% methanol. Fractions containing product were combined and concentrated under reduced pressure to give 0.64 gm (96%) of the title compound as a tan foam.

MS(m/e): 319(M$^+$)

The compounds of Examples 3–4 were prepared by the procedure described in Example 2.

EXAMPLE 3

6-(4-methoxy)benzoyl-3-(dimethyl)amino-1,2,3,4-tetrahydro-9H-carbazole

Beginning with 1.0 gm (2.22 mMol) 6-bromo-3-(dimethyl)amino-9-triisopropylsilyl-1,2,3,4-tetrahydro-9H-carbazole, 0.08 gm (10%) of the title compound were recovered as a yellow foam.

MS(m/e): 348(M$^+$)

EXAMPLE 4

6-(4-chloro)benzoyl-3-(dimethyl)amino-1,2,3,4-tetrahydro-9H-carbazole

Beginning with 0.5 gm (1.11 mMol) 6-bromo-3-(dimethyl)amino-9-triisopropylsilyl-1,2,3,4-tetrahydro-9H-carbazole, 0.17 gm (43.7%) of the title compound were recovered as a yellow foam.

MS(m/e): 352(M$^+$)

EXAMPLE 5

6-(methoxycarbonyl)amino-3-(dimethyl)amino-1,2,
3,4-tetrahydro-9H-carbazole

To a mixture of 6.0 mg (0.026 mMol) 6-amino-3-(dimethyl)amino-1,2,3,4-tetrahydro-9H-carbazole and 8.0 mg (0.07 mMol) polyvinylpyridine in 3.0 mL dichloromethane were added 2.4 mg (0.0273 mMol) methyl chloroformate. The reaction mixture was mixed for 2 days at ambient temperature. To this mixture were then added 90 mg (0.073 mMol) aminomethylated polystyrene and the reaction mixed for an additional 18 hours. The reaction mixture was then filtered and the volatiles evaporated to give 4.0 mg (53%) of the title compound.

MS(m/e): 288(M$^+$)

The compounds of Examples 6–8 were prepared by the procedure described in detail in Example 5.

EXAMPLE 6

6-(ethoxycarbonyl)amino-3-(dimethyl)amino-1,2,3,
4-tetrahydro-9H-carbazole

Beginning with 6.0 mg (0.026 mMol) 6-amino-3-(dimethyl)amino-1,2,3,4-tetrahydro-9H-carbazole and 2.96 mg (0.0273 mMol) ethyl chloroformate, 4.1 mg (52%) of the title compound were recovered.

MS(m/e): 302(M$^+$)

EXAMPLE 7

6-(allyloxycarbonyl)amino-3-(dimethyl)amino-1,2,3,
4-tetrahydro-9H-carbazole

Beginning with 10.0 mg (0.0437 mMol) 6-amino-3-(dimethyl)amino-1,2,3,4-tetrahydro-9H-carbazole and 5.5 mg (0.0458 mMol) allyl chloroformate, 4.4 mg (33%) of the title compound were recovered.

MS(m/e): 313(M$^+$)

EXAMPLE 8

6-(4-fluorophenoxycarbonyl)amino-3-(dimethyl)
amino-1,2,3,4-tetrahydro-9H-carbazole Beginning with 6.0 mg (0.026 mMol) 6-amino-3-(dimethyl)amino-1,2,3,4-tetrahydro-9H-carbazole and 4.8 mg (0.0273 mMol) 4-fluorophenyl chloroformate, 3.8 mg (40%) of the title compound were recovered.

MS(m/e): 368(M$^+$)

EXAMPLE 9

N-methyl-N'-(3-(dimethyl)amino-1,2,3,4-tetrahydro-
9H-carbazol-6-yl)thiourea

To a solution of 10.0 mg (0.0437 mMol) 6-amino-3-(dimethyl)amino-1,2,3,4-tetrahydro-9H-carbazole in 3.0 mL dichloromethane were added 6.2 mg (0.0874 mMol) methyl isothiocyanate. The reaction was mixed for 48 hours and to it were then added 0.15 gm (0.0874 mMol) aminomethylated polystyrene and the reaction mixed for an additional 18 hours. The reaction mixture was then filtered and the volatiles evaporated to give 6.3 mg (48%) of the title compound.

MS(m/e): 302(M$^+$)

The compounds of Examples 10–11 were prepared according to the procedure described in detail in Example 9.

EXAMPLE 10

N-phenyl-N'-(3-(dimethyl)amino-1,2,3,4-tetrahydro-
9H-carbazol-6-yl)thiourea

Beginning with 10.0 mg (0.0437 mMol) 6-amino-3-(dimethyl)amino-1,2,3,4-tetrahydro-9H-carbazole and 11.8 mg (0.0874 mMol) phenyl isothiocyanate, 7.2 mg (39%) of the title compound were recovered.

MS(m/e): 364(M$^+$)

EXAMPLE 11

N-(2,3-dichloro)phenyl-N'-(3-(dimethyl)amino-1,2,
3,4-tetrahydro-9H-carbazol-6-yl)thiourea Beginning with 10.0 mg (0.0437 mMol) 6-amino-3-(dimethyl)amino-1,2,3,4-tetrahydro-9H-carbazole and 17.8 mg (0.0874 mMol) 2,3-dichlorophenyl isothiocyanate, 6.1 mg (33%) of the title compound were recovered.

MS(m/e): 432(M$^+$)

EXAMPLE 12

N-ethyl-N'-(3-(dimethyl)amino-1,2,3,4-tetrahydro-
9H-carbazol-6-yl)urea

To a solution of 10.0 mg (0.0437 mMol) 6-amino-3-(dimethyl)amino-1,2,3,4-tetrahydro-9H-carbazole in 3.0 mL dichloromethane were added 6.2 mg (0.0874 mMol) ethyl isocyanate. The reaction was mixed for 48 hours and to it were then added 0.15 gm (0.0874 mMol) aminomethylated polystyrene and the reaction mixed for an additional 18 hours. The reaction mixture was then filtered and the filtrate washed with 1N hydrochloric acid. The aqueous phase was washed several times with dichloromethane and was then made basic with dilute aqueous sodium hydroxide. The aqueous phase was then extracted several times with an equal volume of dichloromethane. These organic extracts were dried over sodium sulfate and then concentrated under reduced pressure to give 3.0 mg (23%) of the title compound.

MS(m/e): 300(M$^+$)

EXAMPLE 13

N-phenyl-N'-(3-(dimethyl)amino-1,2,3,4-tetrahydro-
9H-carbazol-6-yl)urea

Beginning with 10.0 mg (0.0437 mMol) 6-amino-3-(dimethyl)amino-1,2,3,4-tetrahydro-9H-carbazole and 10.4 mg (0.0874 mMol) phenyl isocyanate, 1.0 mg (7%) of the title compound was recovered using the procedure described in detail in Example 12.

MS(m/e): 348(M$^+$)

EXAMPLE 14

6-(3-methylbutanoyl)amino-3-(dimethyl)amino-6-(3-
methylbutanoyl)amino-1,2,3,4-tetrahydro-9H-
carbazole hydrochloride To a solution of 0.25 gm (1.091 mMol) 6-amino-3-(dimethyl)amino-1,2,3,4-tetrahydro-9H-carbazole and 0.115 μL (1.418 mMol) pyridine in 15 mL dichloromethane at 0° C. were added 0.160 mL (1.309 mMol) isovaleryl chloride. The reaction mixture was allowed to warm to room temperature. After about 40 minutes the reaction was partitioned between dichloromethane and 2N sodium hydroxide. The phases were separated and the organic phase was washed with saturated aqueous sodium chloride, dried over sodium sulfate and concentrated under reduced pressure. The residue was subjected to silica gel chromatography, eluting with dichloromethane containing 15% methanol and 1.5% ammonium hydroxide. Fractions shown to contain product were combined and concentrated under reduced pressure. The residue was converted to the hydrochloride salt which was crystallized from ethanol/diethyl ether to give 0.208 gm (54%) of the title compound.

m.p.=171° C. (decomp.)

Calculated for $C_{19}H_{27}N_3O \cdot HCl$: Theory: C, 65.22; H, 8.07; N, 12.01. Found: C, 64.94; H, 8.12; N, 11.90.

The compounds of Examples 15–19 are prepared by the procedure described in detail in Example 14.

EXAMPLE 15

6-(propanoyl)amino-3-(dimethyl)amino-6-(propanoyl)amino-1,2,3,4-tetrahydro-9H-carbazole hydrochloride Beginning with 0.25 gm (1.091 mMol) 6-amino-3-(dimethyl)amino-1,2,3,4-tetrahydro-9H-carbazole and 0.114 mL (1.309 mMol) propanoyl chloride, 0.268 gm of the title compound were recovered.

m.p.=279° C. (decomp.)

Calculated for $C_{17}H_{23}N_3O \cdot HCl$: Theory: C, 63.44; H, 7.52; N, 13.06. Found: C, 63.24; H, 7.65; N, 13.09.

EXAMPLE 16

6-(2-methylprop-1-en-3-oyl)amino-3-(dimethyl)amino-1,2,3,4-tetrahydro-9H-carbazole hydrobromide Beginning with 0.046 gm (0.20 mMol) 6-amino-3-(dimethyl)amino-1,2,3,4-tetrahydro-9H-carbazole and 0.023 mL (0.24 mMol) 2-methylprop-1-en-3-oyl chloride, 0.035 gm (59%) of 6-(2-methylprop-1-en-3-oyl)amino-3-(dimethyl)amino1,2,3,4-tetrahydro-9H-carbazole were recovered and then treated with hydrogen bromide to give the title compound.

m.p.=236°–238° C.

MS(m/e): 297(M⁺)

EXAMPLE 17

6-(cyclopropanoyl)amino-3-(dimethyl)amino-1,2,3,4-tetrahydro-9H-carbazole hydrobromide Beginning with 0.169 gm (0.74 mMol) 6-amino-3-(dimethyl)amino-1,2,3,4-tetrahydro-9H-carbazole and 0.077mL (0.85 mMol) cyclopropanoyl chloride, 0.195 gm (89%) of 6-(cyclopropanoyl)amino-3-(dimethyl)amino-1,2,3,4-tetrahydro-9H-carbazole were recovered and then treated with hydrogen chloride to give the title compound.

m.p.=216°–218° C.

MS(m/e): 297(M⁺)

Calculated for $C_{18}H_{23}N_3O \cdot HCl$: Theory: C, 64.76; H, 7.25; N, 12.59. Found: C, 64.52; H, 7.13; N, 12.35.

EXAMPLE 18

6-(cyclobutanoyl)amino-3-(dimethyl)amino-1,2,3,4-tetrahydro-9H-carbazole hydrobromide Beginning with 0.169 gm (0.74 mMol) 6-amino-3-(dimethyl)amino-1,2,3,4-tetrahydro-9H-carbazole and 0.097mL (0.85 mMol) cyclobutanoyl chloride, 0.230 gm (99%) of 6-(cyclobutanoyl)amino-3-(dimethyl)amino-1,2,3,4-tetrahydro-9H-carbazole were recovered and then treated with hydrogen chloride to give the title compound.

m.p.=214°–216° C.

MS(m/e): 311(M⁺)

EXAMPLE 19

6-(cyclohexanoyl)amino-3-(dimethyl)amino-1,2,3,4-tetrahydro-9H-carbazole hydrobromide Beginning with 0.132 gm (0.58 mMol) 6-amino-3-(dimethyl)amino-1,2,3,4-tetrahydro-9H-carbazole and 0.085 mL (0.635 mMol) cyclohexanoyl chloride, 0.173 gm (88%) of 6-(cyclohexanoyl)amino-3-(dimethyl)amino-1,2,3,4-tetrahydro-9H-carbazole were recovered and then treated with hydrogen chloride to give the title compound.

m.p.=224°–226° C.

MS(m/e): 340(M⁺)

Calculated for $C_{21}H_{29}N_3O \cdot HCl$: Theory: C, 67.09; H, 8.04; N, 11.17. Found: C, 66.89; H, 7.74; N, 11.40.

EXAMPLE 20

6-(4-chlorobenzoyl)amino-3-(dimethyl)amino-1,2,3,4-tetrahydro-9H-carbazole

To a mixture of 10.6 mg (0.046 mMol) 6-amino-3-(dimethyl)amino-1,2,3,4-tetrahydro-9H-carbazole and 14.0 mg (0.12 mMol) polyvinylpyridine in 3.0 mL dichloromethane were added 8.8 µL (0.069 mMol) 4-chlorobenzoyl chloride. The reaction mixture was mixed for 1 day at ambient temperature. To this mixture were then added 160 mg (0.128 mMol) aminomethylated polystyrene and the reaction mixed for an additional 18 hours. The reaction mixture was diluted with 1.0 mL methanol, treated with potassium carbonate, and filtered through a short column of sodium sulfate. The filtrate was then evaporated to give 2.9 mg (17%) of the title compound as a beige solid.

MS(m/e): 367(M⁺)

The compounds of Examples 21–51 were prepared by the procedure described in detail in Example 20.

EXAMPLE 21

6-(4-methoxybenzoyl)amino-3-(dimethyl)amino-1,2,3,4-tetrahydro-9H-carbazole

Beginning with 10.6 mg (0.046 mMol) 6-amino-3-(dimethyl)amino-1,2,3,4-tetrahydro-9H-carbazole and 8.8 µL (0.063 mMol) 4-methoxybenzoyl chloride, 6.9 mg (41%) of the title compound were recovered as a light brown foam.

MS(m/e): 363(M⁺)

EXAMPLE 22

6-(3-chlorobenzoyl)amino-3-(dimethyl)amino-1,2,3,4-tetrahydro-9H-carbazole

Beginning with 10.6 mg (0.046 mMol) 6-amino-3-(dimethyl)amino-1,2,3,4-tetrahydro-9H-carbazole and 8.8 µL (0.063 mMol) 3-chlorobenzoyl chloride, 4.2 mg (25%) of the title compound were recovered as a brown solid.

MS(m/e): 367(M⁺)

EXAMPLE 23

6-(3-methoxybenzoyl)amino-3-(dimethyl)amino-1,2,3,4-tetrahydro-9H-carbazole

Beginning with 10.6 mg (0.046 mMol) 6-amino-3-(dimethyl)amino-1,2,3,4-tetrahydro-9H-carbazole and 8.8 µL (0.063 mMol) 3-methoxybenzoyl chloride, 9.8 mg (59%) of the title compound were recovered as a brown foam.

MS(m/e): 363(M⁺)

EXAMPLE 24

6-(2-thienoyl)amino-3-(dimethyl)amino-1,2,3,4-tetrahydro-9H-carbazole

Beginning with 10.6 mg (0.046 mMol) 6-amino-3-(dimethyl)amino-1,2,3,4-tetrahydro-9H-carbazole and 8.8 µL (0.082 mMol) 2-thienoyl chloride, 9.7 mg (62%) of the title compound were recovered as a brown solid.

MS(m/e): 339(M$^+$)

EXAMPLE 25

6-(2-fluorobenzoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 5.4 mg (0.051 mMol) 2-fluorobenzoyl chloride, 11.6 mg (74%) of the title compound were recovered as a beige solid.

MS(m/e): 351(M$^+$)

EXAMPLE 26

6-(2-chlorobenzoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 5.7 mg (0.051 mMol) 2-chlorobenzoyl chloride, 12.3 mg (73%) of the title compound were recovered as a beige solid.

MS(m/e): 367(M$^+$)

EXAMPLE 27

6-(2-methoxybenzoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 8.6 µL (0.051 mMol) 2-methoxybenzoyl chloride, 13.4 mg (80%) of the title compound were recovered as a beige solid.

MS(m/e): 367(M$^+$)

EXAMPLE 28

6-(2-methylbenzoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 8.9 µL (0.051 mMol) 2-methylbenzoyl chloride, 11.3 mg (71%) of the title compound were recovered as a beige solid.

MS(m/e): 347(M$^+$)

EXAMPLE 29

6-(3-methylbenzoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 8.9 µL (0.051 mMol) 3-methylbenzoyl chloride, 12.3 mg (77%) of the title compound were recovered as a beige solid.

MS(m/e): 347(M$^+$)

EXAMPLE 30

6-(4-methylbenzoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 8.9 µL (0.051 mMol) 4-methylbenzoyl chloride, 14.6 mg (91%) of the title compound were recovered as a beige solid.

MS(m/e): 347(M$^+$)

EXAMPLE 31

6-(2,3-difluorobenzoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 8.6 µL (0.051 mMol) 2,3-difluorobenzoyl chloride, 13.4 mg (79%) of the title compound were recovered as a beige solid.

MS(m/e): 369(M$^+$)

EXAMPLE 32

6-(2,4-difluorobenzoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 8.6 µL (0.051 mMol) 2,4-difluorobenzoyl chloride, 13.8 mg (81%) of the title compound were recovered as a beige solid.

MS(m/e): 369(M$^+$)

EXAMPLE 33

6-(2,5-difluorobenzoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 8.6 µL (0.051 mMol) 2,5-difluorobenzoyl chloride, 13.3 mg (78%) of the title compound were recovered as a beige solid.

MS(m/e): 369(M$^+$)

EXAMPLE 34

6-(3,4-difluorobenzoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 8.6 µL (0.051 mMol) 3,4-difluorobenzoyl chloride, 7.2 mg (42%) of the title compound were recovered as a beige solid.

MS(m/e): 369(M$^+$)

EXAMPLE 35

6-(3,5-difluorobenzoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 8.6 µL (0.051 mMol) 3,5-difluorobenzoyl chloride, 6.2 mg (36%) of the title compound were recovered as a beige solid.

MS(m/e): 369(M$^+$)

EXAMPLE 36

6-(2,3-dichlorobenzoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 9.5 mg (0.051 mMol) 2,3-dichlorobenzoyl chloride, 14.1 mg (76%) of the title compound were recovered as a brown solid.

MS(m/e): 401(M$^+$)

EXAMPLE 37

6-(1-naphthoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 10.2 µL (0.051 mMol) 1-naphthoyl chloride, 13.8 mg (78%) of the title compound were recovered as a dark brown solid.

MS(m/e): 383(M$^+$)

EXAMPLE 38

6-(2-naphthoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 10.2 µL (0.051 mMol) 2-naphthoyl chloride, 12.6 mg (72%) of the title compound were recovered as a dark brown solid.

MS(m/e): 383(M$^+$)

EXAMPLE 39

6-(4-phenylbenzoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 15 mg (0.051 mMol) 4-phenylbenzoyl chloride, 13.4 mg (71%) of the title compound were recovered as a brown solid.

MS(m/e): 409(M$^+$)

EXAMPLE 40

6-(2-thionaphthoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 14 mg (0.051 mMol) 2-thionaphthoyl chloride, 14.8 mg (83%) of the title compound were recovered as a dark brown solid.

MS(m/e): 389(M$^+$)

EXAMPLE 41

6-(phenylacetyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 8.1 µL (0.051 mMol) phenylacetyl chloride, 13.6 mg (85%) of the title compound were recovered as a grey-brown solid.

MS(m/e): 348(M+1)

EXAMPLE 42

6-(2-thienylacetyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 8.1 µL (0.051 mMol) 2-thienylacetyl chloride, 13.7 mg (84%) of the title compound were recovered as a dark brown solid.

MS(m/e): 354(M+1)

EXAMPLE 43

6-(3-fluorobenzoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 8.1 µL (0.051 mMol) 3-fluorobenzoyl chloride, 10.8 mg (69%) of the title compound were recovered as a beige solid.

MS(m/e): 352(M+1)

EXAMPLE 44

6-(4-bromobenzoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 14.7 mg (0.051 mMol) 4-bromobenzoyl chloride, 3.6 mg (20%) of the title compound were recovered as a light beige solid.

MS(m/e): 413(M$^+$)

EXAMPLE 45

6-(4-iodobenzoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 17.9 mg (0.051 mMol) 4-iodobenzoyl chloride, the title compound was recovered as a light beige solid.

MS(m/e): 459(M$^+$)

EXAMPLE 46

6-(2,4-dichlorobenzoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 9.5 µL (0.051 mMol) 2,4-dichlorobenzoyl chloride, 12.8 mg (72%) of the title compound were recovered as a light beige solid.

MS(m/e): 401(M$^+$)

EXAMPLE 47

6-(benzenesulfonyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 8.6 µL (0.051 mMol) benzenesulfonyl chloride, 5.6 mg (34%) of the title compound were recovered as a light beige solid.

MS(m/e): 370(M$^+$)

EXAMPLE 48

6-(4-fluorobenzenesulfonyl)amino-3-(dimethyl)amino-1,2,3,4-tetrahydro-9H-carbazole Beginning with 10.4 mg (0.046 mMol) 6-amino-3-(dimethyl)amino-1,2,3,4-tetrahydro-9H-carbazole and 13.1 mg (0.067 mMol) 4-fluorobenzenesulfonyl chloride, the title compound was recovered as a light beige solid.

MS(m/e): 388(M$^+$)

EXAMPLE 49

6-(4-methylbenzenesulfonyl)amino-3-(dimethyl)amino-1,2,3,4-tetrahydro-9H-carbazole Beginning with 10.4 mg (0.046 mMol) 6-amino-3-(dimethyl)amino-1,2,3,4-tetrahydro-9H-carbazole and 12.8 mg (0.067 mMol) 4-methylbenzenesulfonyl chloride, 5.3 mg (31%) of the title compound were recovered as a light beige solid.

MS(m/e): 383(M$^+$)

EXAMPLE 50

6-(4-chlorobenzenesulfonyl)amino-3-(dimethyl)amino-1,2,3,4-tetrahydro-9H-carbazole Beginning with 10.4 mg (0.046 mMol) 6-amino-3-(dimethyl)amino-1,2,3,4-tetrahydro-9H-carbazole and 14.1 mg (0.067 mMol) 4-chlorobenzenesulfonyl chloride, 11.5 mg (64%) of the title compound were recovered as a light beige solid.

MS(m/e): 403(M$^+$)

EXAMPLE 51

6-(4-iodobenzenesulfonyl)amino-3-(dimethyl)amino-1,2,3,4-tetrahydro-9H-carbazole Beginning with 10.4 mg (0.046 mMol) 6-amino-3-(dimethyl)amino-1,2,3,4-tetrahydro-9H-carbazole and 20.3 mg (0.067 mMol) 4-iodobenzenesulfonyl chloride, 10.3 mg (47%) of the title compound were recovered as a light beige solid.

MS(m/e): 495(M$^+$)

EXAMPLE 52

6-(4-fluorobenzoyl)amino-3-(dimethyl)amino-1,2,3,4-tetrahydro-9H-carbazole oxalate hemihydrate A solution of 0.10 gm (0.30 mMol) 6-(t-butoxycarbonyl)amino-3-(dimethyl)amino-1,2,3,4-tetrahydro-9H-carbazole in 1.0 mL trifluoroacetic acid was stirred for 20 minutes at room temperature. The reaction mixture was then concentrated under reduced pressure. The residual oil was then dissolved in 5 mL tetrahydrofuran. To this solution was added 1.5 mL triethylamine followed by 5.0 μL (0.42 mMol) 4-fluorobenzoyl chloride and the solution was stirred for 1 hour at room temperature. The reaction mixture was concentrated under reduced pressure and the residue was dissolved in dichloromethane. This solution was washed with aqueous potassium carbonate and was then concentrated under reduced pressure. The residue was dissolved in dilute aqueous tartaric acid and the solution was extracted well with dichloromethane. The remaining aqueous phase was made basic with dilute aqueous sodium hydroxide and was extracted well with dichloromethane. These organic phases were combined, dried over sodium sulfate and concentrated under reduced pressure. The residue was subjected to silica gel chromatography, eluting with 95:5 chloroform:5% ammonium hydroxide in methanol. Fractions containing the product were combined and concentrated under reduced pressure to give 0.102 gm (95%) of 6-(4-fluorobenzoyl)amino-3-(dimethyl)amino-1,2,3,4-tetrahydro-9H-carbazole.

MS(m/e): 351(M$^+$)

Calculated for C$_{21}$H$_{22}$N$_3$OF: Theory: C, 71.27; H, 6.31; N, 11.96. Found: C, 71.47; H, 6.32; N, 11.86.

A solution of 0.82 mg (0.23 mMol) 6-(4-fluorobenzoyl)amino-3-(dimethyl)amino-1,2,3,4-tetrahydro-9H-carbazole in 1 mL ethyl acetate were added to a solution of 0.21 mg (0.23 mMol) oxalic acid in 1 mL ethyl acetate. The solid which formed was filtered, washed with ethyl acetate and dried to give 0.77 mg (75%) of the title compound.

m.p.>150° C. (decomp.)

The compounds of Examples 53–55 were prepared by the procedure described in detail in Example 52.

EXAMPLE 53

6-(benzoyl)amino-3-(dimethyl)amino-1,2,3,4-tetrahydro-9H-carbazole

Beginning with 0.198 gm (0.60 mMol) 6-(t-butoxycarbonyl)amino-3-(dimethyl)amino-1,2,3,4-tetrahydro-9H-carbazole and 9.7 μL (0.84 mMol) benzoyl chloride, 0.075 gm (38%) of the title compound were prepared as a light grey foam.

MS(m/e): 333(M$^+$)

Calculated for C$_{21}$H$_{23}$N$_3$O: Theory: C, 75.65; H, 6.95; N, 12.60. Found: C, 75.35; H, 6.97; N, 12.50.

EXAMPLE 54

6-(2-furoyl)amino-3-(dimethyl)amino-1,2,3,4-tetrahydro-9H-carbazole oxalate hemihydrate Beginning with 0.10 gm (0.30 mMol) 6-(t-butoxycarbonyl)amino-3-(dimethyl)amino-1,2,3,4-tetrahydro-9H-carbazole and 5.0 μL (0.51 mMol) 2-furoyl chloride, 0.080 gm (82%) of 6-(2-furoyl)amino-3-(dimethyl)amino-1,2,3,4-tetrahydro-9H-carbazole were prepared.

MS(m/e): 323(M$^+$)

Calculated for C$_{19}$H$_{21}$N$_3$O$_2$: Theory: C, 70.57; H, 6.54; N, 12.99. Found: C, 70.29; H, 6.54; N, 12.99.

0.063 gm (0.20 mMol) of 6-(2-furoyl)amino-3-(dimethyl)amino-1,2,3,4-tetrahydro-9H-carbazole were treated with oxalic acid to give 0.052 gm (64%) of the title compound.

m.p.>110° C. (decomp.)

EXAMPLE 55

6-(2-chloro-4-fluorobenzoyl)amino-3-(dimethyl)amino-1,2,3,4-tetrahydro-9H-carbazole Beginning with 0.081 gm (0.245 mMol) 6-(t-butoxycarbonyl)amino-3-(dimethyl)amino-1,2,3,4-tetrahydro-9H-carbazole and 0.046 gm (0.27 mMol) 2-chloro-4-fluorobenzoyl chloride, 0.089 gm (94%) of the title compound were recovered as a light beige solid.

MS(m/e): 385(M$^+$)

IR(KBr): 3626, 3472, 3427, 2975, 2962, 2786, 1666, 1603, 1478 cm$^{-1}$

Calculated for C$_{21}$H$_{21}$N$_3$OClF: Theory: C, 65.37; H, 5.49; N, 10.89. Found: C, 65.17; H, 5.50; N, 10.73.

EXAMPLE 56

6-(indol-5-oyl)amino-3-(dimethyl)amino-1,2,3,4-tetrahydro-9H-carbazole hydrochloride To a solution of 43.5 mg (0.27 mMol) indole-5-carboxylic acid in 1.5 mL dimethylformamide were added 44.3 mg (0.27 mMol) carbonyldiimidazole resulting in immediate gas evolution. The reaction mixture was stirred for 4 hours at room temperature and then 60.0 mg (0.26 mMol) 6-amino-3-(dimethyl)amino-1,2,3,4-tetrahydro-9H-carbazole were added. After 3 days the reaction mixture was concentrated under reduced pressure. The residue was subjected to silica gel chromatography, eluting with 4:1 dichloromethane:2% ammonium hydroxide in methanol. Fractions shown to contain product were combined and concentrated under reduced pressure to give 66.7 mg (69%) of 6-(indol-5-oyl)amino-3-(dimethyl)amino-1,2,3,4-tetrahydro-9H-carbazole. The compound was converted to its corresponding hydrochloride salt, crystallizing from ethanol:diethyl ether.

m.p.=235°–237° C.

Exact Mass: Calculated for C$_{23}$H$_{25}$N$_4$O: Theory: 373.2028; Found: 373.2042.

EXAMPLE 57

6-(4-fluorobenzoyl)amino-3-amino-1,2,3,4-tetrahydro-9H-carbazole hydrochloride

To a solution of 0.187 gm (0.41 mMol) 6-(4-fluorobenzoyl)amino-3-(1-phthalimido)-1,2,3,4-tetrahydro- 9H-carbazole in 6 mL ethanol and 1.5 mL water were added 0.45 mL hydrazine monohydrate and the reaction mixture was stirred at room temperature. After 12 hours the reaction mixture was concentrated under reduced pressure and the residue partitioned between ethyl acetate and saturated aqueous sodium carbonate. The organic phase was washed with water, dried over sodium sulfate and concentrated under reduced pressure. The residue was subjected to silica gel chromatography. Fractions shown to contain product were combined and concentrated under reduced pressure to give 0.101 gm (76%) of 6-(4-fluorobenzoyl)amino-3-amino-1,2,3,4-tetrahydro-9H-carbazole. The compound was converted to its corresponding hydrochloride salt, crystallizing from ethanol:diethyl ether.

m.p.=252°–255° C.

MS(m/e): 323(M+)

Calculated for $C_{19}H_{18}N_3OF \cdot HCl$: Theory: C, 63.42; H, 5.32; N, 11.68. Found: C, 63.20; H, 5.57; N, 11.91.

EXAMPLE 58

6-(4-fluorobenzoyl)amino-3-(ethyl)amino-1,2,3,4-tetrahydro-9H-carbazole hydrobromide and 6-(4-fluorobenzoyl)amino-3-(diethyl)amino-1,2,3,4-tetrahydro-9H-carbazole hydrochloride To a solution of 0.194 gm (0.60 mMol) 6-(4-fluorobenzoyl)amino-3-amino-1,2,3,4-tetrahydro-9H-carbazole in 15 mL ethanol were added 300 mg Raney Nickel and the reaction mixture heated to reflux. After 2 hours the reaction mixture was filtered through a pad of celite. The pad was washed with 400 mL of methanol and the filtrates were concentrated under reduced pressure. The residue was subjected to silica gel chromatography, eluting with 100:10:3 dichloromethane:methanol:ammonium hydroxide. Fractions containing the first eluting product were combined and concentrated under reduced pressure to give 137.3 mg (60.3%) of 6-(4-fluorobenzoyl)amino-3-(diethyl)amino-1,2,3,4-tetrahydro-9H-carbazole. The corresponding hydrochloride salt was prepared.

m.p.=222°–224° C.

Exact Mass: Calculated for $C_{23}H_{27}N_3OF$: Theory: 380.2138; Found: 380.2144.

Fractions containing the second eluting spot were combined and concentrated under reduced pressure to give 0.033 gm (16%) of 6-(4-fluorobenzoyl)amino-3-(ethyl)amino-1,2,3,4-tetrahydro-9H-carbazole. The corresponding hydrobromide salt was prepared.

m.p.=226°–230° C.

Exact Mass: Calculated for $C_{21}H_{23}N_3OF$: Theory: 352.1825; Found: 352.1825.

EXAMPLE 59

6-(4-fluorobenzoyl)amino-3-(2-phenylethyl) amino-1,2,3,4-tetrahydro-9H-carbazole hydrochloride To a mixture of 0.568 gm (1.758 mMol) 6-(4-fluorobenzoyl)amino-3-amino-1,2,3,4-tetrahydro-9H-carbazole, 0.485 gm (3.512 mMol) potassium carbonate and 0.316 gm (2.109 mMol) sodium iodide in 10 mL acetonitrile were added 0.288 mL (2.109 mMol) 2-phenyl-1-ethyl bromide and the reaction mixture was heated at reflux for 5 hours. The reaction mixture was then cooled to room temperature and partitioned between dichloromethane and water. The aqueous phase was extracted well with dichloromethane. The dichloromethane phases were combined, dried over magnesium sulfate and concentrated under reduced pressure. The residue was subjected to silica gel chromatography, eluting with 97:2.5:0.5 dichloromethane:methanol:ammonium hydroxide. Fractions shown to contain product were combined and concentrated under reduced pressure to give 0.543 gm (72.3%) 6-(4-fluorobenzoyl)amino-3-(2-phenethyl)amino-1,2,3,4-tetrahydro-9H-carbazole. The corresponding hydrochloride salt was prepared to provide the title compound.

m.p.207°–208° C.

Calculated for $C_{27}H_{26}N_3OF \cdot HCl$: Theory: C, 68.89; H, 5.87; N, 9.06. Found: C, 68.69; H, 6.07; N, 8.94.

EXAMPLE 60

6-(4-fluorobenzoyl)amino-3-(2-(4-fluorophenyl) ethyl)amino-1,2,3,4-tetrahydro-9H-carbazole hydrochloride Beginning with 0.601 gm (1.860 mMol) 6-(4-fluorobenzoyl)amino-3-amino-1,2,3,4-tetrahydro-9H-carbazole and 0.525 gm (2.405 mMol) 2-(4-fluorophenyl)-1-mesyloxyethane, 0.270 gm (32.8%) of the title compound were prepared by the procedure described in Example 31.

m.p.210°–211° C.

Calculated for $C_{27}H_{25}N_3OF_2 \cdot HCl$: Theory: C, 67.29; H, 5.44; N, 8.72. Found: C, 67.05; H, 5.61; N, 8.45.

EXAMPLE 61

6-(4-fluorobenzoyl)amino-3-(2-(1-methyl-1H-pyrazol-4-yl)ethyl)amino-1,2,3,4-tetrahydro-9H-carbazole hydrochloride To a mixture of 0.40 gm (1.24 mMol) 6-(4-fluorobenzoyl) amino-3-amino-1,2,3,4-tetrahydro-9H-carbazole and 0.257 gm (1.86 mMol) potassium carbonate in 8.0 mL dimethylform-amide were added 0.303 gm (1.49 mMol) 2-(1-methyl-1H-pyrazol-4-yl)-1-mesyloxyethane in 2.0 mL dimethylformamide and the mixture was stirred at 60°–75° C. for 18 hours. An additional 0.101 gm (0.50 mMol) 2-(1-methyl-1H-pyrazol-4-yl)-1-mesyloxyethane were added and the reaction heated to 150° C. After 1.5 hours the reaction mixture was cooled to room temperature and was then partitioned between water and dichloromethane. The aqueous phase was extracted again with dichloromethane. The combined organic phases were dried over sodium sulfate and concentrated under reduced pressure. The residue was subjected to silica gel chromatography, eluting with 95:5:0.5 dichloromethane:methanol:ammonium hydroxide. Fractions shown to contain product were combined and concentrated under reduced pressure to give 0.180 gm (33.6%) of 6-(4-fluorobenzoyl)amino-3-(2-(1-methyl-1H-pyrazol-4-yl)ethyl)amino-1,2,3,4-tetrahydro-9H-carbazole. The corresponding hydrochloride salt was prepared to provide the title compound.

m.p.=185°–190° C.

Exact Mass: Calculated for $C_{25}H_{26}N_5OF$: Theory: 432.2202; Found: 432.2200.

EXAMPLE 62

3-(2-(1-isopropyl-1H-pyrazol-4-yl)ethyl)amino-6-(4-fluorobenzoyl)amino-1,2,3,4-tetrahydro-9H-carbazole hydrochloride Beginning with 0.400 gm (1.24 mMol) 6-(4-fluorobenzoyl)amino-3-amino-1,2,3,4-tetrahydro-9H- carbazole and 0.346 gm (1.49 mMol) 2-(1-methyl-1H-pyrazol-3-yl)-1-mesyloxyethane, 0.0632 gm (10.3%) of the title compound were prepared by the procedure described in Example 33.

Exact Mass: Calculated for $C_{27}H_{30}N_5OF$: Theory: 460.2513; Found: 460.2491.

EXAMPLE 63

6-hydroxy-3-amino-1,2,3,4-tetrahydro-9H-carbazole

To a solution of 0.871 gm (2.98 mMol) 6-benzyloxy-3-amino-1,2,3,4-tetrahydro-9H-carbazole in 200 mL ethanol were added about 2.0 gm Raney Nickel and hydrogen introduced to the reaction mixture under balloon pressure. After stirring for 18 hours at room temperature the balloon was refilled with hydrogen and the reaction stirred an additional 3 days at room temperature. The reaction mixture was filtered and the filtrate concentrated under reduced pressure to give a colorless solid. The residual solid was subjected to silica gel chromatography, eluting with 80:15:5 dichloromethane:methanol:ammonium hydroxide. Fractions shown to contain product were combined and concentrated under reduced pressure to give 0.335 gm (56%) of the title compound.

m.p.=230° C. (decomp.)

Calculated for $C_{12}H_{14}N_2O$: Theory: C, 71.26; H, 6.98; N, 13.85. Found: C, 71.00; H, 7.01; N, 13.70.

EXAMPLE 64

6-hydroxy-3-(methyl)amino-1,2,3,4-tetrahydro-9H-carbazole 6-benzyloxy-3-(t-butyloxycarbonyl)amino-1,2,3,4-tetrahydro-9H-carbazole To a solution of 1.00 gm (3.42 mMol) 6-benzyloxy-3-amino-1,2,3,4-tetrahydro-9H-carbazole in 30 mL tetrahydrofuran were added 1.79 mL 2N sodium hydroxide followed by 0.784 gm (3.59 mMol) di(t-butyl)dicarbonate. The reaction mixture was stirred at room temperature for about 45 minutes and was then concentrated under reduced pressure. The residue was dissolved in dichloromethane and washed well with water. The remaining organics were dried over magnesium sulfate and concentrated under reduced pressure to give 1.339 gm (99%) of the desired compound.

6-benzyloxy-3-(methyl)amino-1,2,3,4-tetrahydro-9H-carbazole

A solution of 1.35 gm (3.44 mMol) 6-benzyloxy-3-(t-butyloxycarbonyl)amino-1,2,3,4-tetrahydro-9H-carbazole in 15 mL tetrahydrofuran were added dropwise over 30–40 minutes to a suspension of 0.46 gm (12.04 mMol) lithium aluminum hydride in 30 mL tetrahydrofuran at 0° C. The reaction mixture was allowed to stir at this temperature for 20 minutes after the addition was complete and was then warmed to 75° C. for 4.5 hours. The reaction mixture was then cooled to room temperature and treated with sodium sulfate decahydrate. The mixture was cooled to 0° C. and was then filtered. The solid collected was washed sequentially with tetrahydrofuran and dichloromethane, and the combined filtrates were concentrated under reduced pressure. The residue was subjected to silica gel chromatography, eluting with ethyl acetate. Fractions shown to contain product were combined and concentrated under reduced pressure to 0.797 gm (76%) of the desired product.

m.p.=146°–147° C.

Calculated for $C_{20}H_{22}N_2O$: Theory: C, 78.40; H, 7.24; N, 9.16. Found: C, 78.53; H, 7.36; N, 9.14.

Hydrogenolysis

Beginning with 0.522 gm (1.70 mMol) 6-benzyloxy-3-(methyl)amino-1,2,3,4-tetrahydro-9H-carbazole, 0.226 mg (61%) of the title compound were recovered as described in Example 35.

m.p.=120°–121° C.

Exact Mass: Calculated for: $C_{13}H_{16}N_2O$: Theory: 217.1341; Found: 217.1336.

EXAMPLE 65

6-hydroxy-3-(ethyl)amino-1,2,3,4-tetrahydro-9H-carbazole 6-benzyloxy-3-(ethyl)amino-1,2,3,4-tetrahydro-9H-carbazole To a solution of 0.225 gm (0.77 mMol) 6-benzyloxy-3-amino-1,2,3,4-tetrahydro-9H-carbazole in 20 mL acetonitrile were added 0.223 gm (1.617 mMol) potassium carbonate followed by 130 µL (1.617 mMol) iodoethane and the reaction mixture was stirred at room temperature for 18 hours. The reaction mixture was then heated at 60° C. for 4 hours and then at 50°–45° C. for 3 hours. The reaction mixture was then concentrated under reduced pressure and the residue partitioned between dichloromethane and water. The organic phase was then dried over magnesium sulfate and concentrated under reduced pressure. The residue was subjected to radial chromatography (silica gel, 2 mm), eluting with 97:3:1 dichloromethane:methanol:ammonium hydroxide. Fractions shown to contain the desired compound were concentrated under reduced pressure to give 0.045 gm (6%) of the desired compound.

Exact Mass: Calculated for: $C_{21}H_{25}N_2O$: Theory: 321.1967; Found: 321.1970.

Hydrogenolysis

Beginning with 0.492 gm (1.536 mMol) 6-benzyloxy-3-(ethyl)amino-1,2,3,4-tetrahydro-9H-carbazole, 0.271 mg (76.6%) of the title compound were recovered as described in Example 35.

m.p.=117°–118° C.

Exact Mass: Calculated for: $C_{14}H_{18}N_2O$: Theory: 231.1497; Found: 231.1490.

EXAMPLE 66

6-hydroxy-3-(propyl)amino-1,2,3,4-tetrahydro-9H-carbazole hydrochloride 6-benzyloxy-3-(propyl)amino-1,2 3,4-tetrahydro-9H-carbazole To a solution of 0.600 gm (2.05 mMol) 6-benzyloxy-3-amino-1,2,3,4-tetrahydro-9H-carbazole in 35 mL acetonitrile were added 0.283 gm (2.05 mMol) potassium carbonate followed by 240 µL (2.46 mMol) iodopropane and the reaction mixture was stirred at room temperature for 2.5 days. Additional iodopropane was added and the reaction stirred at room temperature until all of the starting material had been consumed. The reaction mixture was then partitioned between dichloromethane and water. The aqueous phase was extracted with dichloromethane and the combined organic phases were then dried over magnesium sulfate and concentrated under reduced pressure. The residue was subjected to silica gel chromatography, eluting with 96.5:3:0.5 dichloromethane:isopropanol:ammonium hydroxide. Fractions shown to contain the desired compound were concentrated under reduced pressure to give 0.270 gm (39%) of the desired compound.

Hydrogenolysis

To a solution of 0.27 gm 6-benzyloxy-3-(propyl)amino-1,2,3,4-tetrahydro-9H-carbazole in 50 mL ethanol were added 100 mg 5% palladium on carbon and the reaction mixture was hydrogenated at room temperature for 16 hours with an initial hydrogen pressure of 60 p.s.i. The reaction mixture was then filtered through celite, washing the filter pad well with methanol. The combined filtrates were concentrated under reduced pressure. The residue was subjected to silica gel chromatography, eluting with 90:9:1 dichloromethane:methanol:ammonium hydroxide. Fractions shown to contain product were combined and concentrated under reduced pressure to give 0.083 gm (42%) of the title compound. The corresponding hydrochloride salt was formed and crystallized from methanol/diethyl ether.

m.p.=105° C. (decomp.)

Exact Mass: Calculated for: $C_{15}H_{20}N_2O$: Theory: 245.1654; Found: 245.1659.

The compounds of Examples 67–68 were prepared by the procedure described in detail in Example 66.

EXAMPLE 67

6-hydroxy-3-(diethyl)amino-1,2,3,4-tetrahydro-9H-carbazole hydrochloride

Beginning with 1.00 gm (2.05 mMol) 6-benzyloxy-3-amino 1,2,3,4-tetrahydro-9H-carbazole and 820 μL (10.27 mMol) -iodoethane, 0.0882 gm (10%) of 6-hydroxy-3-(diethyl)amino-1,2,3,4-tetrahydro-9H-carbazole were recovered. The hydrochloride salt was prepared to give the title compound.

m.p.=271°–271° C.

Exact Mass: Calculated for: $C_{16}H_{22}N_2O$: Theory: 259.1810; Found: 259.1816.

EXAMPLE 68

6-hydroxy-3-(dipropyl)amino-1,2,3,4-tetrahydro-9H-carbazole hydrochloride

Beginning with 1.00 gm (2.05 mMol) 6-benzyloxy-3-amino-1,2,3,4-tetrahydro-9H-carbazole and 1.67 mL (17.11 mMol) 1-iodopropane, 0.200 gm (70%) of 6-hydroxy-3-(dipropyl)amino-1,2,3,4-tetrahydro-9H-carbazole were recovered. The hydrochloride salt was prepared to give the title compound.

Calculated for $C_{18}H_{26}N_2O.HCl$: Theory: C, 66.96; H, 8.43; N, 8.68. Found: C, 66.69; H, 8.25; N, 8.90.

EXAMPLE 69

6-hydroxy-3-(2-phenyleth-1-yl)amino-1,2,3,4-tetrahydro-9H-carbazole hydrochloride
6-benzyloxy-3-(2-phenyleth-1-yl)amino-1,2,3,4-tetrahydro-9H-carbazole To a solution of 0.32 gm (1.1 mMol) 6-benzyloxy-3-amino-1,2,3,4-tetrahydro-9H-carbazole in 8 mL acetonitrile were added 0.30 gm (1.68 mMol) potassium carbonate, 0.25 gm (1.68 mMol) sodium iodide and 0.23 mL (1.68 mMol) 2-phenyl-1-ethyl bromide. The resulting mixture was stirred 4 hours at room temperature followed by 5 hours at reflux. The reaction mixture was cooled to room temperature and then partitioned between dichloromethane and water. The aqueous phase was extracted well with dichloromethane. All of the organic phases were combined, dried over magnesium sulfate and concentrated under reduced pressure. The residue was subjected to silica gel chromatography, eluting with 7% methanol in dichloromethane. Fractions shown to contain product were concentrated under reduced pressure to give 0.345 gm (79%) of the desired compound. A portion was converted to the corresponding hydrochloride salt, m.p.=242–244° C. (ethanol/diethyl ether).
Hydrogenolysis Beginning with 0.336 gm (0.85 mMol) 6-benzyloxy-3-(2-phenyleth-1-yl)-amino-1,2,3,4-tetrahydro-9H-carbazole, 0.175 gm (67%) of 6-hydroxy-3-(2-phenylethyl)amino-1,2,3,4-tetrahydro-9H-carbazole were prepared by the procedure described in detail in Example 35. The hydrochloride salt was prepared and crystallized from ethanol/diethyl ether to give the title compound.

m.p.=178°–180° C.

MS(m/e): 307(M$^+$)

Calculated for $C_{20}H_{22}N_2O.HCl$: Theory: C, 70.06; H, 6.76; N, 8.17. Found: C, 70.32; H, 6.78; N, 8.22.

EXAMPLE 70

6-hydroxy-3-(2-(4-fluorophenyl)eth-1-yl)amino-1,2,3,4-tetrahydro-9H-carbazole hydrochloride
6-benzyloxy-3-(2-(4-fluorophenyl)eth-1-yl)amino-1,2,3,4-tetrahydro-9H-carbazole Beginning with 1.00 gm (3.422 mMol) 6-benzyloxy-3-amino-1,2,3,4-tetrahydro-9H-carbazole and 1.274 gm (5.82 mMol) 2-(4-fluorophenyl)-1-mesyloxyethane, 0.896 gm (63%) of 6-benzyloxy-3-(2-(4-fluorophenyl)eth-1-yl)amino-1,2,3,4-tetrahydro-9H-carbazole were recovered by the procedure described in detail in Example 33. A portion was converted to the corresponding hydrochloride salt and crystallized from ethanol/diethyl ether.

m.p.=244°–245° C.

Calculated for $C_{27}H_{27}N_2OF.HCl$: Theory: C, 71.91; H, 6.26; N, 6.21. Found: C, 71.70; H, 6.26; N, 6.09.
Hydrogenolysis To a solution of 0.700 gm (1.69 mMol) 6-benzyloxy-3-(2-(4-fluorophenyl)eth-1-yl)amino-1,2,3,4-tetrahydro-9H-carbazole in 50 mL methanol were added 1.07 gm (16.90 mMol) ammonium formate followed by 0.190 gm 5% palladium on carbon. The resulting mixture was stirred at reflux for 15 minutes. The reaction mixture was then filtered through a bed of celite and the filter cake washed well with methanol. The combined filtrates were concentrated under reduced pressure and the residue partitioned between water and dichloromethane. The phases were separated and the aqueous was extracted again with 4:1 isopropanol:dichloromethane. The combined extracts were dried over magnesium sulfate, concentrated under reduced pressure, and the residue subjected to silica gel chromatography, eluting with 91:8:1 dichloromethane:methanol:ammonium hydroxide. Fractions shown to contain product were combined and concentrated under reduced pressure to give 0.245 gm (52%) of 6-hydroxy-3-(2-(4-fluorophenyl)eth-1-yl)amino-1,2,3,4-tetrahydro-9H-carbazole. The hydrochloride salt was prepared and crystallized from ethanol/diethyl ether to give the title compound.

m.p.=160° C. (decomp.)

Calculated for $C_{20}H_{21}N_2OF.HCl$: Theory: C, 66.57; H, 6.14; N, 7.76. Found: C, 66.34; H, 6.14; N, 7.59.

EXAMPLE 71

6-benzyloxy-3-(2-(4-chlorophenyl)eth-1-yl)amino-1,2,3,4-tetrahydro-9H-carbazole hydrochloride Beginning with 1.00 gm (3.422 mMol) 6-benzyloxy-3-amino-1,2,3,4-tetrahydro-9H-carbazole and 1.371 gm (5.82 mMol) 2-(4-chlorophenyl)-1-mesyloxyethane, 0.833 gm (56%) of 6-benzyloxy-3-(2-(4-chlorophenyl)eth-1-yl)amino-1,2,3,4-tetrahydro-9H-carbazole were recovered by the procedure described in detail in Example 33. A portion was converted to the corresponding hydrochloride salt and crystallized from ethanol/diethyl ether.

m.p.=238°–240° C.

Calculated for $C_{27}H_{27}N_2OCl\cdot HCl$: Theory: C, 68.38; H, 6.04; N, 5.99. Found: C, 68.63; H, 6.17; N, 6.05.

EXAMPLE 72

6-hydroxy-3-(2-(1-methyl-1H-pyrazol-4-yl)ethyl) amino-1,2,3,4-tetrahydro-9H-carbazole hydrochloride 6-benzyloxy-3-(2-(1-methyl-1H-pyrazol-4-yl)ethyl)amino-1,2,3,4-tetrahydro-9H-carbazole To a solution of 1.00 gm (3.422 mMol) 6-benzyloxy-3-amino-1,2,3,4-tetrahydro-9H-carbazole in 50 mL acetonitrile were added 1.04 gm (7.53 mMol) potassium carbonate followed by 1.26 gm (6.16 mMol) 2-(1-methyl-1H-pyrazol-4-yl)-1-mesyloxyethane and the reaction mixture was heated to reflux for 18 hours. To the reaction mixture were then added 0.021 gm (0.171 mMol) 4-dimethylaminopyridine and reflux was continued for 36 additional hours. The reaction mixture was cooled to room temperature and then partitioned between dichloromethane and water. The aqueous phase was extracted well with dichloromethane. All of the organic phases were combined, dried over magnesium sulfate and concentrated under reduced pressure. The residue was subjected to silica gel chromatography, eluting with 2.5% methanol in dichloromethane containing 0.5% ammonium hydroxide. Fractions shown to contain product were concentrated under reduced pressure to give 0.610 gm (44%) of the desired compound.

Hydrogenolysis

Beginning with 0.610 gm (1.524 mMol) 6-benzyloxy-3-(2-(1-methyl-1H-pyrazol-4-yl)ethyl)amino-1,2,3,4-tetrahydro-9H-carbazole, 0.245 gm (52%) of 6-hydroxy-3-(2-(1-methyl-1H-pyrazol-4-yl)ethyl)amino-1,2,3,4-tetrahydro-9H-carbazole were prepared by the hydrogenolysis procedure described in detail in Example 42. The hydrochloride salt was prepared and crystallized from ethanol/diethyl ether to give the title compound.

m.p.=286° C. (decomp.)

Calculated for $C_{18}H_{21}N_4O\cdot HCl$: Theory: C, 62.33; H, 6.68; N, 16.15. Found: C, 62.54; H, 6.71; N, 16.20.

EXAMPLE 73

6-hydroxy-3-(2-(1-isopropyl-1H-pyrazol-4-yl)ethyl) amino-1,2,3,4-tetrahydro-9H-carbazole hydrochloride 6-benzyloxy-3-(2-(1-isopropyl-1H-pyrazol-4-yl)ethyl) amino-1,2,3,4-tetrahydro-9H-carbazole Beginning with 0.698 gm (2.39 mMol) 6-benzyloxy-3-amino-1,2,3,4-tetrahydro-9H-carbazole and 0.787 gm (3.39 mMol) 2-(1-isopropyl-1H-pyrazol-4-yl)-1-mesyloxyethane, 0.649 gm (63.4%) of the desired compound were prepared by the procedure described in detail in Example 72.

MS(m/e): 428(M$^+$)

A portion of the material was converted to its corresponding hydrochloride salt, m.p.=258°–260° C. (ethanol/diethyl ether).

Hydrogenolysis

Beginning with 0.532 gm (1.24 mMol) 6-benzyloxy-3-(2-(1-isopropyl-1H-pyrazol-4-yl)ethyl)amino-1,2,3,4-tetrahydro-9H-carbazole, 0.322 gm (77%) of 6-hydroxy-3-(2-(1-isopropyl-1H-pyrazol-4-yl)ethyl)amino-1,2,3,4-tetrahydro-9H-carbazole were prepared by the hydrogenolysis procedure described in detail in Example 42. The hydrochloride salt was prepared and crystallized from ethanol/diethyl ether to give the title compound.

m.p.=251°–253° C.

MS(m/e): 338(M$^+$)

Calculated for $C_{20}H_{26}N_4O\cdot HCl$: Theory: C, 64.07; H, 7.26; N, 14.94. Found: C, 64.29; H, 7.28; N, 15.17.

EXAMPLE 74

N-methyl-N-(2-phenyleth-1-yl)-6-hydroxy-3-amino-1,2,3,4-tetrahydro-9H-carbazole hydrochloride N-methyl-N-(2-phenyleth-1-yl)-6-benzyloxy-3-amino-1,2,3,4-tetrahydro-9H-carbazole To a solution of 0.30 gm (0.98 mMol) 6-benzyloxy-3-(methyl)amino-1,2,3,4-tetrahydro-9H-carbazole in 15 mL acetonitrile were added 0.271 (1.96 mMol) potassium carbonate, 0.177 gm (1.18 mMol) sodium iodide and 0.161 mL (1.18 mMol) 2-phenyl-1-ethyl bromide. The reaction mixture was heated to reflux for 18 hours. At this time an additional 0.07 mL (0.49 mMol) 2-phenyl-1-ethyl bromide were added and reflux was continued for 4 hours. The reaction mixture was cooled to room temperature and then partitioned between dichloromethane and water. The aqueous phase was extracted well with dichloromethane. All organic phases were combined, dried over magnesium sulfate and concentrated under reduced pressure. The residue was subjected to radial chromatography (4 mm, silica gel), eluting with 4.5% methanol in dichloromethane containing 0.55% ammonium hydroxide. Fractions containing product were combined and concentrated under reduced pressure to give 0.324 gm (80.6%) of the desired compound.

Hydrogenolysis

Beginning with 0.324 gm (0.79 mMol) N-methyl-N-(2-phenyleth-1-yl)-6-benzyloxy-3-amino-1,2,3,4-tetrahydro-9H-carbazole, 0.205 gm (78%) of N-methyl-N-(2-phenylethyl)-6-hydroxy-3-amino-1,2,3,4-tetrahydro-9H-carbazole were prepared by the hydrogenolysis procedure described in detail in Example 70. The hydrochloride salt was prepared and crystallized from ethanol/diethyl ether to give the title compound.

m.p.=159°–160° C.

Calculated for $C_{21}H_{24}N_2O\cdot HCl$: Theory: C, 70.67; H, 7.06; N, 7.85. Found: C, 70.41; H, 7.05; N, 7.83.

EXAMPLE 75

N-methyl-N-(2-(4-fluorophenyl)eth-1-yl)-6-hydroxy-3-amino-1,2,3,4-tetrahydro-9H-carbazole hydrochloride N-methyl-N-(2-(4-fluorophenyl)eth-1-yl)-6-benzyloxy-3-amino-1,2,3,4-tetrahydro-9H-carbazole Beginning with 0.30 gm (0.98 mMol) 6-benzyloxy-3-(methyl)amino-1,2,3,4-tetrahydro-9H-carbazole in 15 mL acetonitrile and 0.406 mg (1.86 mMol) 2-(4-fluorophenyl)-1-mesyloxyethane, 0.262 gm (62%) of the desired compound were recovered by the procedure described in detail in Example 46.

Hydrogenolysis

Beginning with 0.262 gm (0.61 mMol) N-methyl-N-(2-(4-fluorophenyl)eth-1-yl)-6-benzyloxy-3-amino-1,2,3,4-tetrahydro-9H-carbazole, 0.183 gm (88%) of N-methyl-N-(2-(4-fluorophenyl)eth-1-yl)-3-amino-6-hydroxy-1,2,3,4-tetrahydro-9H-carbazole were prepared by the hydrogenolysis procedure described in detail in Example 70. The hydrochloride salt was prepared and crystallized from ethanol/diethyl ether to give the title compound.

m.p.=165°–166° C.

Calculated for $C_{21}H_{23}N_2OF\cdot HCl$: Theory: C, 67.28; H, 6.45; N, 7.47. Found: C, 67.48; H, 6.64; N, 7.52.

EXAMPLE 76

N-methyl-N-(2-(1-isopropyl-1H-pyrazol-4-yl)ethyl)-6-hydroxy-3-amino-1,2,3,4-tetrahydro-9H-carbazole hydrochloride N-methyl-N-(2-(1-isopropyl-1H-pyrazol-4-yl)ethyl)-6-benzyloxy-3-amino-1,2,3,4-tetrahydro-9H-carbazole Beginning with 0.202 gm (0.66 mMol) 6-benzyloxy-3-(methyl)amino-1,2,3,4-tetrahydro-9H-carbazole in 15 mL acetonitrile and 0.284 mg (1.22 mMol) 2-(1-isopropyl-1H-pyrazol-4-yl)-1-mesyloxyethane, 0.253 gm (87%) of the desired compound were recovered by the procedure described in detail in Example 74.

MS(m/e): 442($M^+$)

A portion was converted to the corresponding hydrochloride salt, m.p.=134°–136° C. (ethanol/diethyl ether).

Hydrogenolysis

Beginning with 0.196 gm (0.44 mMol) N-methyl-N-(2-(1-isopropyl-1H-pyrazol-4-yl)ethyl)-6-benzyloxy-3-amino-1,2,3,4-tetrahydro-9H-carbazole, 0.120 gm (77%) of N-methyl-N-(2-(1-isopropyl-1H-pyrazol-4-yl)ethyl)-6-hydroxy-3-amino-1,2,3,4-tetrahydro-9H-carbazole were prepared by the hydrogenolysis procedure described in detail in Example 70. The hydrochloride salt was prepared and crystallized from ethanol/diethyl ether to give the title compound.

m.p.=184°–186° C.
MS(m/e): 352($M^+$)
Calculated for $C_{21}H_{28}N_4O\cdot HCl$: Theory: C, 64.85; H, 7.52; N, 14.40. Found: C, 65.08; H, 7.52; N,14.46.

EXAMPLE 77

7-(4-fluorobenzoyl)amino-4-amino-10H-cyclohepta[7,6-b]indole

To a solution of 0.854 gm (1.827 mMol) of a mixture of 7-(4-fluorobenzoyl)amino-3- and 4-(1-phthalimidoyl)-10H-cyclohepta[7,6-b]indole in 50 mL ethanol were added 3.5 mL hydrazine hydrate and 12 mL water. The mixture was stirred at room temperature for 18 hours. The reaction mixture was then concentrated under reduced pressure and the residue subjected to silica gel chromatography, eluting with 84:15:1 dichloromethane:methanol:ammonium hydroxide. Fractions containing the desired compound were combined and concentrated under reduced pressure to give 0.196 gm (32%) of the title compound.

m.p.=121°–122° C.
Exact Mass: Calculated for: $C_{20}H_{21}N_3OF$: Theory: 338.1669; Found: 338.1679.

EXAMPLE 78

7-(4-fluorobenzoyl)amino-4-(dimethyl)amino-10H-cyclohepta[7,6-b]indole hydrochloride To a solution of 0.165 gm (0.489 mMol) 7-(4-fluorobenzoyl)amino-4-amino-10H-cyclohepta[7,6-b]indole in 15 mL tetrahydrofuran were added 1.96 mL (3.9 mMol) 2N sodium hydroxide followed by 104 μL (1.223 mMol) methyl mesylate and the resulting mixture was stirred at room temperature for 18 hours. The reaction mixture was diluted with 100 mL dichloromethane and was then washed with 1N sodium hydroxide. The remaining organics were dried over magnesium sulfate and then concentrated under reduced pressure. The residue was subjected to radial chromatography (silica gel, 1 mm), eluting with 88.5:10:1.5 dichloromethane:methanol:ammonium hydroxide. Fractions containing the desired compound were concentrated under reduced pressure to give 0.035 gm (19%) 7-(4-fluorobenzoyl)amino-4-(dimethyl)amino-10H-cyclohepta-[7,6-b]indole. The corresponding hydrochloride salt was prepared to give the title compound.

m.p.=198° C.
Exact Mass: Calculated for: $C_{22}H_{25}N_3OF$: Theory: 366.1982; Found: 366.1991.

EXAMPLE 79

7-(benzyloxycarbonyl)amino-4-amino-10H-cyclohepta[7,6-b]indole hydrochloride

Beginning with 1.61 gm (3.36 mMol) of a mixture of 7-(benzyloxycarbonyl)amino-3- and 4-(1-phthalimidoyl)-10H-cyclohepta[7,6-b]indole, 0.527 gm (44.9%) 7-(benzyloxycarbonyl)amino-4-amino-10H-cyclohepta[7,6-b]indole were prepared by the procedure described in detail in Example 49 The corresponding hydrochloride salt was prepared to give the title compound.

m.p.=201°–203° C.
MS(m/e): 350($M^+$)

EXAMPLE 80

7-(benzyloxycarbonyl)amino-4-(dimethyl)amino-10H-cyclohepta[7,6-b]indole hydrobromide To a solution of 0.276 gm (0.79 mMol) 7-(benzyloxycarbonyl)amino-4-amino-10H-cyclohepta[7,6-b]indole in 10 mL acetonitrile were added 0.22 mL (1.5 mMol) triethylamine followed by 0.10 mL (1.6 mMol) iodomethane and the resulting solution stirred for 2 hours at room temperature. To the mixture were then added 3.2 mL (6.4 mMol) 2N sodium hydroxide and the reaction stirred for 48 hours at room temperature. The reaction mixture was then partitioned between dichloromethane and water. The organic phase was dried over sodium sulfate and concentrated under reduced pressure. The residue was subjected to silica gel chromatography, eluting with 88:10:2 dichloromethane:methanol:ammonium hydroxide. Fractions containing product were combined and concentrated under reduced pressure to give 0.056 gm (19%) 7-(benzyloxycarbonyl)amino-4-(dimethyl)-amino-10H-cyclohepta[7,6-b]indole. The corresponding hydrobromide salt was prepared to give the title compound.

m.p.=91°–93° C.
Exact Mass: Calculated for: $C_{23}H_{28}N_3O_2$: Theory: 378.2182; Found: 378.2199.

EXAMPLE 81

7-hydroxy-4-amino-10H-cyclohepta[7,6-b]indole
7-benzyloxy-4-amino-10H-cyclohepta[7,6-b]indole Beginning with 1.19 gm (2.73 mMol) of a mixture of 7-benzyloxy-3- and 4-(1-phthalimidoyl)-10H-cyclohepta[7,6-b]indole, 0.334 gm (40%) 7-benzyloxy-4-amino-10H-cyclohepta[7,6-b]indole were prepared by the procedure described in detail in Example 78

Hydrogenolysis

Beginning with 0.166 gm (0.54 mMol) 7-benzyloxy-4-amino-10H-cyclohepta[7,6-b]indole, 0.054 gm (46%) of the title compound were prepared by the procedure described in detail in Example 63.

m.p.=215° C. (decomp.)

Exact Mass: Calculated for: $C_{13}H_{17}N_2O$: Theory: 217.1341; Found: 217.1306.

EXAMPLE 82

7-hydroxy-4-(methyl)amino-10H-cyclohepta[7,6-b]indole hydrochloride 7-benzyloxy-4-(t-butyloxycarbonyl)amino-10H-cyclohepta[7,6-b]indole To a solution of 1.08 gm (3.52 mMol) 7-benzyloxy-4-amino-10H-cyclohepta[7,6-b]indole in 30 mL tetrahydrofuran were added 1.85 mL 2N sodium hydroxide followed by 0.808 gm (3.7 mMol) di(t-butyl)dicarbonate and the mixture was stirred for 1 hour at room temperature. The reaction mixture was concentrated under reduced pressure and the residue partitioned between dichloromethane and water. The organic phase was separated, dried over sodium sulfate and concentrated under reduced pressure. The residue was subjected to silica gel chromatography, eluting with 30% hexane in ethyl acetate. Fractions containing product were combined and concentrated under reduce pressure to give 1.37 gm (96%) of the desired compound.

7-benzyloxy-4-(methyl)amino-10H-cyclohepta[7,6-b]indole

A solution of 1.37 gm (3.37 mMol) 7-benzyloxy-4-(t-butyloxycarbonyl)amino-10H-cyclohepta[7,6-b]indole in 15 mL tetrahydrofuran was added dropwise over 30 minutes to a suspension of 0.47 gm (12.4 mMol) lithium aluminum hydride in 30 mL tetrahydrofuran at 0° C. After the addition was complete, the reaction mixture was stirred for 30 minutes at room temperature and then for 4 hours at reflux. The reaction mixture was cooled to room temperature and then to it was added sodium sulfate decahydrate until no more gas evolution was observed. The resulting suspension was filtered and the filter cake washed with dichloromethane. The combined filtrates were concentrated under reduced pressure and the residue subjected to silica gel chromatography, eluting with 10% methanol in dichloromethane containing 0.5% ammonium hydroxide. Fractions containing product were combined and concentrated under reduced pressure to give 0.97 gm (90%) of the desired compound.

Hydrogenolysis

Beginning with 0.233 gm (0.73 mMol) 7-benzyloxy-4-(methyl)amino-10H-cyclohepta[7,6-b]indole, 0.104 gm (62%) of 7-hydroxy-4-(methyl)amino-10H-cyclohepta[7,6-b]indole were prepared by the procedure described in detail in Example 73. The corresponding hydrochloride was prepared and crystallized from ethanol/diethyl ether to give the title compound.

m.p.=262° C. (decomp.)

Exact Mass: Calculated for: $C_{14}H_{19}N_2O$: Theory: 231.1497; Found: 231.1487.

EXAMPLE 83

7-hydroxy-4-(dimethyl)amino-10H-cyclohepta[7,6-b]indole hydrochloride 7-benzyloxy-4-(dimethyl)amino-10H-cyclohepta[7,6-b]indole Beginning with 0.483 gm (1.5 mMol) 7-benzyloxy-4-(methyl)amino-10H-cyclohepta[7,6-b]indole, 0.410 gm (82%) of the desired product were prepared by the acylation/hydride reduction sequence described in detail in Example 82.

Hydrogenolysis

Beginning with 0.405 gm (1.21 mMol) 7-benzyloxy-4-(dimethyl)amino-10H-cyclohepta[7,6-b]indole, 0.305 gm (90%) of 7-hydroxy-4-(dimethyl)amino-10H-cyclohepta[7,6-b]indole were prepared by the procedure described in detail in Example 63. The corresponding hydrochloride was prepared and crystallized from ethanol/diethyl ether to give the title compound.

m.p.=186°–194° C.

Exact Mass: Calculated for: $C_{15}H_{21}N_2O$: Theory: 245.1654; Found: 245.1655.

EXAMPLE 84

7-hydroxy-4-(ethyl)amino-10H-cyclohepta[7,6-b]indole hydrochloride

Beginning with 0.288 gm (0.94 mMol) 7-benzyloxy-4-amino-10H-cyclohepta[7,6-b]indole, 0.140 gm (69%) of 7-hydroxy-4-(ethyl)-amino-10H-cyclohepta[7,6-b]indole were prepared by the procedure described in detail in Example 35, except that the reaction mixture was heated to 60° C. during the course of the reaction. The corresponding hydrochloride was prepared and crystallized from ethanol/diethyl ether to give the title compound.

m.p.=270° C. (decomp.)

MS(m/e): 245($M^+$)

Calculated for $C_{15}H_{20}N_2O\cdot HCl$: Theory: C, 64.16; H, 7.54; N, 9.98. Found: C, 64.46; H, 7.54; N, 9.94.

EXAMPLE 85

N,N-diethyl-6-hydroxy-3-aminomethyl-1,2,3,4-tetrahydro-9H-carbazole hydrochloride N,N-diethyl-6-benzyloxy-3-carboxamido-1,2,3,4-tetrahydro-9H-carbazole To a solution of 0.322 gm (1.00 mMol) 6-benzyloxy-3-carboxy-1,2,3,4-tetrahydro-9H-carbazole in 2.5 mL tetrahydrofuran at 0° C. were added a solution of 96.0 µL (1.10 mMol) oxalyl chloride in 1.5 mL tetrahydrofuran dropwise followed by 73 µL (0.90 mMol) pyridine. The reaction mixture was allowed to stir at room temperature for 3 hours. The reaction mixture was then concentrated under reduced pressure and the residue redissolved in 15 mL tetrahydrofuran. This solution was then cooled to 0° C. and to it was added a solution of 145 µL diethylamine in 1.5 mL tetrahydrofuran dropwise. The resulting solution was stirred at room temperature for 18 hours. The reaction mixture was then partitioned between saturated aqueous potassium carbonate and dichloromethane. The organic phase was washed well with 2N sodium hydroxide, dried over magnesium sulfate and concentrated under reduced pressure. The residue was subjected to silica gel chromatography, eluting with 98:2 dichloromethane:methanol. Fractions containing product were combined and concentrated under reduced pressure to give 0.155 gm (41%) of the desired compound.

N,N-diethyl-6-benzyloxy-3-aminomethyl-6-benzyloxy-1,2,3,4-tetrahydro-9H-carbazole A solution of 0.368 gm (0.978 mMol) N,N-diethyl-6-benzyloxy-3-carboxamido-1,2,3,4-tetrahydro-9H-carbazole in 15 mL tetrahydrofuran were added dropwise to a suspension of 56.0 mg (1.47 mMol) lithium aluminum hydride in 10 mL tetrahydrofuran at 0° C. The reaction was stirred for 2.5 hours at room temperature after the addition was complete. The reaction mixture was then again cooled to 0° C. and 100 mg sodium sulfate decahydrate were added. After 2 hours the reaction mixture was diluted with dichloromethane, dried over magnesium sulfate and concentrated under reduced pressure to give the desired compound.

Hydrogenolysis

Beginning with 0.354 gm (0.978 mMol) N,N-diethyl-6-benzyloxy-3-aminomethyl-1,2,3,4-tetrahydro-9H- carbazole, 0.145 gm (55%) of N,N-diethyl-6-hydroxy-3-aminomethyl-1,2,3,4-tetrahydro-9H-carbazole were prepared by the procedure described in detail in Example 63. The corresponding hydrochloride salt was prepared to give the title compound.

m.p.=240° C. (decomp.)

Calculated for $C_{17}H_{24}N_2O \cdot HCl$: Theory: C, 66.11; H, 8.16; N, 9.07. Found: C, 66.38; H, 8.27; N, 8.81.

EXAMPLE 86

N-methyl-6-hydroxy-3-aminomethyl-1,2,3,4-tetrahydro-9H-carbazole hydrochloride

Beginning with 1.00 gm 6-benzyloxy-3-carboxy-1,2,3,4-tetrahydro-9H-carbazole, 0.195 gm (27%) of N-methyl-6-hydroxy-3-aminomethyl-1,2,3,4-tetrahydro-9H-carbazole were prepared by the procedure described in detail in Example 85. The corresponding hydrochloride salt was prepared to give the title compound.

m.p.=145°–146° C.

Exact Mass: Calculated for: $C_{14}H_{18}N_2O$: Theory: 231.1497; Found: 231.1485.

EXAMPLE 87

N,N-dimethyl-6-hydroxy-3-aminomethyl-1,2,3,4-tetrahydro-9H-carbazole

Beginning with 1.00 gm 6-benzyloxy-3-carboxy-1,2,3,4-tetrahydro-9H-carbazole, 0.141 gm (18%) of the title compound were prepared by the procedure described in detail in Example 85.

m.p.=107°–108° C.

Calculated for $C_{15}H_{20}N_2O$: Theory: C, 73.73; H, 8.25; N, 11.47. Found: C, 73.95; H, 8.49; N, 11.32.

EXAMPLE 88

N,N-dipropyl-6-hydroxy-3-aminomethyl-1,2,3,4-tetrahydro-9H-carbazole hydrochloride Beginning with 1.00 gm 6-benzyloxy-3-carboxy-1,2,3,4-tetrahydro-9H-carbazole, 0.096 gm (10%) of N,N-dipropyl-6-hydroxy-3-aminomethyl-1,2,3,4-tetrahydro-9H-carbazole were prepared by the procedure described in detail in Example 85. The corresponding hydrochloride salt was prepared to give the title compound.

m.p.=261°–263° C. (decomp.)

Calculated for $C_{19}H_{28}N_2O \cdot HCl$: Theory: C, 67.74; H, 8.68; N, 8.31. Found: C, 67.51; H, 8.77; N, 8.22.

EXAMPLE 89

N-ethyl-N-propyl-6-hydroxy-3-aminomethyl-1,2,3,4-tetrahydro-9H-carbazole hydrochloride Beginning with 0.811 gm 6-benzyloxy-3-carboxy-1,2,3,4-tetrahydro-9H-carbazole, 0.189 gm (16%) of N-ethyl-N-propyl-6-hydroxy-3-aminomethyl-1,2,3,4-tetrahydro-9H-carbazole were prepared by the procedure described in detail in Example 85, except that the hydrogenolysis was performed at 50° C. The corresponding hydrochloride salt was prepared to give the title compound.

m.p.>220° C. (decomp.)

MS(m/e): 286(M$^+$)

Calculated for $C_{18}H_{26}N_2O \cdot HCl$: Theory: C, 66.96; H, 8.43; N, 8.68. Found: C, 66.68; H, 8.24; N, 8.60.

General procedure for the coupling of carboxylic acids with 6-amino-3-(dimethyl)amino-1,2,3,4-tetrahydro-9H-carbazole To a suspension of 4–5 equivalents of polymer bound 1-ethyl-3-(3-dimethylaminopropyl)carbodiimide (Desai, et al., *Tetrahedron Letters*, 34(48), 7685 (1993)) in chloroform are added 1 equivalent of 6-amino-3-(dimethyl)amino-1,2,3,4-tetrahydro-9H-carbazole and 2–3 equivalents of the carboxylic acid. The reaction is agitated until the reaction is complete, heat may be applied if necessary. The resin is removed by filtration and the product isolated by evaporation of solvent. This procedure is illustrated by Examples 90–108.

EXAMPLE 90

6-(2-thienoyl)amino-3-(dimethyl)amino-1,2,3,4-tetrahydro-9H-carbazole

Beginning with 8.7 mg (0.038 mMol) 6-amino-3-(dimethyl)amino-1,2,3,4-tetrahydro-9H-carbazole and 11.0 mg (0.086 mMol) thiophene-2-carboxylic acid, 6.0 mg (47%) of the title compound were recovered as a beige solid.

MS(m/e): 339(M$^+$)

EXAMPLE 91

6-(5-methylfur-3-oyl)amino-3-(dimethyl)amino-1,2,3,4-tetrahydro-9H-carbazole

Beginning with 8.7 mg (0.038 mMol) 6-amino-3-(dimethyl)amino-1,2,3,4-tetrahydro-9H-carbazole and 10.0 mg (0.090 mMol) 5-methylfuran-3-carboxylic acid, 7.9 mg (62%) of the title compound were recovered as a beige solid.

MS(m/e): 337(M$^+$)

EXAMPLE 92

6-(2-methylfur-3-oyl)amino-3-(dimethyl)amino-1,2,3,4-tetrahydro-9H-carbazole

Beginning with 8.7 mg (0.038 mMol) 6-amino-3-(dimethyl)amino-1,2,3,4-tetrahydro-9H-carbazole and 11 mg (0.087 mMol) 2-methylfuran-3-carboxylic acid, 12.7 mg (99%) of the title compound were recovered as a beige solid.

MS(m/e): 337(M$^+$)

EXAMPLE 93

6-(5-methylfur-2-oyl)amino-3-(dimethyl)amino-1,2,3,4-tetrahydro-9H-carbazole

Beginning with 8.7 mg (0.038 mMol) 6-amino-3-(dimethyl)amino-1,2,3,4-tetrahydro-9H-carbazole and 11.0 mg (0.084 mMol) 5-methylfuran-2-carboxylic acid, 6.8 mg (53%) of the title compound were recovered as a beige solid.

MS(m/e): 337(M$^+$)

EXAMPLE 94

6-(3-methylthien-2-oyl)amino-3-(dimethyl)amino-1,2,3,4-tetrahydro-9H-carbazole

Beginning with 8.7 mg (0.038 mMol) 6-amino-3-(dimethyl)amino-1,2,3,4-tetrahydro-9H-carbazole and 12 mg (0.084 mMol) 3-methylthiophene-2-carboxylic acid, the title compound was recovered as a beige solid.

EXAMPLE 95

6-(4-methoxythien-3-oyl)amino-3-(dimethyl)amino-1,2,3,4-tetrahydro-9H-carbazole

Beginning with 8.7 mg (0.038 mMol) 6-amino-3-(dimethyl)amino-1,2,3,4-tetrahydro-9H-carbazole and 13.0 mg (0.082 mMol) 5-methoxythiophene-2-carboxylic acid, 9.6 mg (69%) of the title compound were recovered as a beige solid.

MS(m/e): 369(M$^+$)

EXAMPLE 96

6-(2,6-dichlorobenzoyl)amino-3-(dimethyl)amino-1,2,3,4-tetrahydro-9H-carbazole

Beginning with 8.7 mg (0.038 mMol) 6-amino-3-(dimethyl)amino-1,2,3,4-tetrahydro-9H-carbazole and 18.0 mg (0.086 mMol) 2,6-dichlorobenzoic acid, 2.4 mg (16%) of the title compound were recovered as a beige solid.

MS(m/e): 401(M$^+$)

EXAMPLE 97

6-(3-furoyl)amino-3-(dimethyl)amino-1,2,3,4-tetrahydro-9H-carbazole

Beginning with 8.7 mg (0.038 mMol) 6-amino-3-(dimethyl)amino-1,2,3,4-tetrahydro-9H-carbazole and 10.0 mg (0.089 mMol) furan-3-carboxylic acid, 5.8 mg (47%) of the title compound were recovered as a beige solid.

MS(m/e): 324(M$^+$)

EXAMPLE 98

6-(3-thienoyl)amino-3-(dimethyl)amino-1,2,3,4-tetrahydro-9H-carbazole

Beginning with 8.7 mg (0.038 mMol) 6-amino-3-(dimethyl)amino-1,2,3,4-tetrahydro-9H-carbazole and 11.0 mg (0.086 mMol) thiophene-3-carboxylic acid, 6.8 mg (53%) of the title compound were recovered as a beige solid.

MS(m/e): 339(M$^+$)

EXAMPLE 99

6-(4-methansulfonylbenzoyl)amino-3-(dimethyl)amino-1,2,3,4-tetrahydro-9H-carbazole Beginning with 8.7 mg (0.038 mMol) 6-amino-3-(dimethyl)amino-1,2,3,4-tetrahydro-9H-carbazole and 17.0 mg (0.085 mMol) 4-methanesulfonylbenzoic acid, 2.0 mg (13%) of the title compound were recovered as a beige solid.

MS(m/e): 411 (M$^+$)

EXAMPLE 100

6-(4-pyridinecarbonyl)amino-3-(dimethyl)amino-1,2,3,4-tetrahydro-9H-carbazole

Beginning with 9.2 mg (0.040 mMol) 6-amino-3-(dimethyl)amino-1,2,3,4-tetrahydro-9H-carbazole and 12.5 mg (0.101 mMol) 4-pyridinecarboxylic acid, 5.0 mg (37%) of the title compound were recovered as a beige solid.

MS(m/e): 334(M$^+$)

EXAMPLE 101

6-(3-pyridinecarbonyl)amino-3-(dimethyl)amino-1,2,3,4-tetrahydro-9H-carbazole

Beginning with 9.2 mg (0.040 mMol) 6-amino-3-(dimethyl)amino-1,2,3,4-tetrahydro-9H-carbazole and 12.5 mg (0.101 mMol) 3-pyridinecarboxylic acid, 7.2 mg (54%) of the title compound were recovered as a beige solid.

MS(m/e): 334(M$^+$)

EXAMPLE 102

6-(2-chloro-3-pyridinecarbonyl)amino-3-(dimethyl)amino-1,2,3,4-tetrahydro-9H-carbazole Beginning with 9.2 mg (0.040 mMol) 6-amino-3-(dimethyl)amino-1,2,3,4-tetrahydro-9H-carbazole and 15.9 mg (0.101 mMol) 2-chloro-3-pyridinecarboxylic acid, the title compound was recovered as a white solid.

EXAMPLE 103

6-(6-chloro-3-pyridinecarbonyl)amino-3-(dimethyl)amino-1,2,3,4-tetrahydro-9H-carbazole Beginning with 9.2 mg (0.040 mMol) 6-amino-3-(dimethyl)amino-1,2,3,4-tetrahydro-9H-carbazole and 4.9 mg (0.101 mMol) 6-chloro-3-pyridinecarboxylic acid, 4.9 mg (31%) of the title compound were recovered as a brown solid.

MS(m/e): 369(M$^+$)

EXAMPLE 104

6-(cyclopentanoyl)amino-3-(dimethyl)amino-1,2,3,4-tetrahydro-9H-carbazole

Beginning with 9.2 mg (0.040 mMol) 6-amino-3-(dimethyl)amino-1,2,3,4-tetrahydro-9H-carbazole and 11.6 mg (0.101 mMol) cyclopentanecarboxylic acid, 7.5 mg (53%) of the title compound were recovered as a light beige solid.

MS(m/e): 326(M$^+$)

EXAMPLE 105

6-(4-nitrobenzoyl)amino-3-(dimethyl)amino-1,2,3,4-tetrahydro-9H-carbazole

Beginning with 9.2 mg (0.040 mMol) 6-amino-3-(dimethyl)amino-1,2,3,4-tetrahydro-9H-carbazole and 16.9 mg (0.101 mMol) 4-nitrobenzoic acid, 1.2 mg (8%) of the title compound were recovered as a dark brown solid.

MS(m/e): 379(M$^+$)

EXAMPLE 106

6-(4-trifluoromethylbenzoyl)amino-3-(dimethyl)amino-1,2,3,4-tetrahydro-9H-carbazole Beginning with 9.2 mg (0.040 mMol) 6-amino-3-(dimethyl)amino-1,2,3,4-tetrahydro-9H-carbazole and 19.2 mg (0.101 mMol) 4-trifluoromethylbenzoic acid, 5.7 mg (35%) of the title compound were recovered as a beige solid.

MS(m/e): 401(M$^+$)

EXAMPLE 107

6-(4-cyanobenzoyl)amino-3-(dimethyl)amino-1,2,3,4-tetrahydro-9H-carbazole

Beginning with 9.2 mg (0.040 mMol) 6-amino-3-(dimethyl)amino-1,2,3,4-tetrahydro-9H-carbazole and 14.9 mg (0.101 mMol) 4-cyanobenzoic acid, 6.7 mg (47%) of the title compound were recovered as a beige solid.

MS(m/e): 358(M$^+$)

EXAMPLE 108

6-(4-acetylbenzoyl)amino-3-(dimethyl)amino-1,2,3,4-tetrahydro-9H-carbazole

Beginning with 9.2 mg (0.040 mMol) 6-amino-3-(dimethyl)amino-1,2,3,4-tetrahydro-9H-carbazole and 16.6 mg (0.101 mMol) 4-acetylbenzoic acid, 7.8 mg (52%) of the title compound were recovered as a beige solid.

MS(m/e): 375(M+)

EXAMPLE 109

6-(dimethylsulfonyl)amino-3-(dimethyl)amino-1,2,3,4-tetrahydro-9H-carbazole hydrochloride To a solution of 0.197 gm (0.86 mMol) 6-amino-3-(dimethyl)amino-1,2,3,4-tetrahydro-9H-carbazole in 8 mL dichloromethane at 0° C. were added 0.14 mL (6.18 mMol) pyridine followed by 0.14 mL (6.51 mMol) dimethylsulfamoyl chloride. The reaction mixture was stirred at 0° C. for 2 hours and was then allowed to warm to room temperature over 2 hours. After storage at 0° C. for 18 hours, the reaction mixture was partitioned between 2N sodium hydroxide and 8% methanol in dichloromethane. The phases were separated and the aqueous phase was extracted several times with 8% methanol in dichloromethane. The organic phases were combined, dried over sodium sulfate and concentrated under reduced pressure. The residue was subjected to silica gel chromatography, eluting with dichloromethane containing 15% methanol and 2% ammonium hydroxide. Fractions containing product were combined and concentrated under reduced pressure to give 0.20 gm (69%) of 6-(dimethylsulfonyl)amino-3-(dimethyl)amino-1,2,3,4-tetrahydro-9H-carbazole. The corresponding hydrochloride salt was prepared to give the title compound which crystallized from ethanol/diethyl ether.

m.p.=217°–219° C.

Exact Mass: Calculated for: $C_{16}H_{25}N_4O_2S$. Theory: 337.1698; Found: 337.1688.

EXAMPLE 110

(R)- and (S)-N-((R)-(+)-a-methyl-(4-nitrophenyl)ethyl)-6-bromo-2-amino-1,2,3,4-tetrahydro-9H-carbazole Reductive Amination To a solution of 20.0 gm (100.9 mMol) 1,4-cyclohexanedione mono-(2,2-dimethyl)propane-1,3-diol monoketal in 250 mL methanol were added 35.0 gm (172.7 mMol) R-(+)-a-methyl-(4-nitrophenyl)ethylamine hydrochloride, 25.0 gm (398 mMol) sodium cyanoborohydride and 10 mL acetic acid. The reaction mixture was allowed to stir for 18 hours at room temperature. To the reaction mixture were then added an additional charge of 25.0 gm (398 mMol) sodium cyanoborohydride and the reaction mixture stirred for an additional 18 hours at room temperature. The reaction mixture was then diluted with dilute aqueous tartaric acid and the solution exhaustively extracted with dichloromethane. The remainining aqueous phase was made basic with aqueous sodium hydroxide and extracted well with dichloromethane. These dichloromethane extracts were combined, dried over sodium sulfate and concentrated under reduced pressure to give 33.7 gm (96%) of N-((R)-(+)-a-methyl-(4-nitrophenyl)ethyl)-4-aminocyclohexanone 2,2-dimethylpropane-1,2-diol ketal as a brownish yellow oil.

MS(m/e): 348(M+)

Ketal Deprotection

A solution of 33.42 gm (95.91 mMol) N-((R)-(+)-a-methyl-(4-nitrophenyl)ethyl)-4-aminocyclohexanone 2,2-dimethylpropane-1,2-diol ketal in 250 mL 98% formic acid was heated to 40° C. for 66 hours. The reaction mixture was concentrated under reduced pressure to a volume of about 50 mL and was then treated with aqueous potassium carbonate. The basic aqueous mixture was extracted well with dichloromethane. These organic phases were combined, dried over sodium sulfate and concentrated under reduced pressure to give 22.36 gm (89%) N-((R)-(+)-a-methyl-(4-nitrophenyl)ethyl)-4-aminocyclohexanone as a brown oil.

Preparation of phenylhydrazone

To a solution of 22.3 gm (85.01 mMol) N-((R)-(+)-a-methyl-(4-nitrophenyl)ethyl)-4-aminocyclohexanone in 375 mL ethanol were added 19.0 gm (85.0 mMol) 4-bromophenylhydrazine hydrochloride and 6.73 gm (85.1 mMol) pyridine. The reaction mixture was heated to 80° C. for 48 hours. The reaction mixture was cooled to room temperature and concentrated under reduced pressure. The residue was dissolved in dichloromethane and the organic solution was washed sequentially with aqueous potassium carbonate and saturated aqueous sodium chloride. The remaining organics were dried over sodium sulfate and concentrated under reduced pressure to give 31.66 gm (86%) N-((R)-(+)-a-methyl-(4-nitrophenyl)ethyl)-4-aminocyclohexanone 4-bromophenylhydrazone as a brown solid.

Fischer indole reaction

A solution of 31.66 gm (73.4 mMol) N-((R)-(+)-a-methyl-(4-nitrophenyl)ethyl)-4-aminocyclohexanone 4-bromophenylhydrazone in 500 mL 3.7M ethanolic hydrogen chloride was stirred at reflux for 18 hours. The reaction mixture was cooled to room temperature and was then concentrated under reduced pressure. The residue was partitioned between 1N sodium hydroxide and dichloromethane. The aqueous phase was extracted well with dichloromethane. The organic phases were combined, dried over sodium sulfate and concentrated under reduced pressure. The residue was subjected to silica gel chromatography, eluting with 5% methanol in dichloromethane which contained 1% ammonium hydroxide.

(S)-(−)-N-((R)-(+)-a-methyl-(4-nitrophenyl)ethyl)-6-bromo-3-amino-1,2,3,4-tetrahydro-9H-carbazole The fastest eluting diastereomer was recovered as 9.47 gm (31%) of a reddish-brown oil.

MS(m/e): 415(M+)

IR(CHCl$_3$): 3471, 2970, 2926, 2845, 1522, 1471, 1348, 857 cm$^{-1}$ $[a]_D^{20}$(c=10, methanol): −122.3°

Calculated for $C_{20}H_{20}N_3O_2Br$: Theory: C, 57.78; H, 4.87; N, 10.14. Found: C, 58.23; H, 5.03; N, 10.12.

(R)-(+)-N-((R)-(+)-a-methyl-(4-nitrophenyl)ethyl)-6-bromo-3-amino-1,2,3,4-tetrahydro-9H-carbazole The slower eluting diastereomer was recovered as 8.13 gm (27%) of pale green crystals.

MS(m/e): 415(M+)

IR(CHCl$_3$): 3471, 3012, 2970, 2952, 2846, 1522, 1471, 1348, 857 cm$^{-1}$ $[a]_D^{20}$(c=10, methanol): +337.90°

Calculated for $C_{20}H_{20}N_3O_2Br$: Theory: C, 57.78; H, 4.87; N, 10.14. Found: C, 58.26; H, 5.03; N, 9.93

X-Ray crystallography determined that the slower eluting diastereomer was of the S,R absolute configuration.

EXAMPLE 110

(R)-(+)-6-bromo-2-(dimethyl)amino-1,2,3,4-tetrahydro-9H-carbazole hydroiodide

Quaternization

To a solution of 5.00 gm (12.1 mMol) (R)-(+)-N-((R)-(+)-a-methyl-(4-nitrophenyl)ethyl)-6-bromo-2-amino-1,2,3,4-tetrahydro-9H-carbazole in 150 mL acetonitrile were added 10.0 mL iodomethane followed by 5.0 gm potassium carbonate. The mixture was stirred for 2 days at room temperature and then for 18 hours at reflux. The reaction mixture was then cooled to room temperature and the resulting yellow precipitate filtered, washed with methanol and dried under reduced pressure to give 3.65 gm (53%) (R)-(+)-N,N-dimethyl-N-((R)-(+)-a-methyl-(4-nitrophenyl)ethyl)-6-bromo-2-amino-1,2,3,4-tetrahydro-9H-carbazole iodide as a yellow solid.

Calculated for $C_{22}H_{25}N_3O_2BrI$: Theory: C, 46.34; H, 4.42; N, 7.37. Found: C, 46.22; H, 4.41; N, 7.30.

Hydrogenolysis

A mixture of 0.70 gm (1.23 mMol) (R)-(+)-N,N-dimethyl-N-((R)-(+)-a-methyl-(4-nitrophenyl)ethyl)-6-bromo-2-amino-1,2,3,4-tetrahydro-9H-carbazole iodide and 0.20 gm sulfided platinum on carbon in 150 mL methanol were hydrogenated at room temperature for 18 hours at an initial hydrogen pressure of 40 p.s.i. The reaction mixture was then degassed and warmed to effect methanolysis. The reaction mixture was filtered and concentrated under reduced pressure to give 0.471 gm (91%) of the title compound as a light yellow solid.

m.p.=252° C.

MS(m/e): 293($M^+$)

IR(KBr): 3271, 3016, 2924, 2842, 2737, 2709, 1469, 1460, 1435, 1308, 793 $cm^{-1}$ $[a]_D^{20}$(c=10, methanol): +54.7°

Calculated for $C_{14}H_{18}N_2BrI$: Theory: C, 39.93; H, 4.31; N, 6.65. Found: C, 39.87; H, 4.19; N, 6.38.

EXAMPLE 111

Resolution of Racemic 6-bromo-2-(dimethyl)amino-1,2,3,4-tetrahydro-9H-carbazole

To a solution of 5.0 gm (17.06 mMol) 6-bromo-2-(dimethyl)amino-1,2,3,4-tetrahydro-9H-carbazole in 200 mL of warm ethyl acetate was added a solution of 6.59 gm (17.06 mMol) di-p-toluoyl-D-tartaric acid in 100 mL ethyl acetate with mixing. After standing for 4 hours, the resulting precipitate was filtered and dried to give 12.0 gm of the salt. A suspension of 1.0 gm of this solid was heated to boiling in 10 mL of methanol. This mixture was then cooled to room temperature and allowed to stand for 18 hours. The remaining solid was filtered and dried to give 0.65 gm. This solid was again suspended in 10 mL boiling methanol and allowed to cool and stand for 18 hours to give 0.52 gm of solid after filtration and vacuum drying. This solid was partitioned between dichloromethane and dilute aqueous sodium hydroxide. The phases were separated and the organics were washed with saturated aqueous sodium chloride, dried over sodium sulfate and concentrated under reduced pressure. The residue was dissolved in 7 mL of toluene and allowed to stand at room temperature for 18 hours. The solution was filtered to remove the solid which had formed and the filtrate was concentrated under reduced pressure to give 0.133 gm of an oil which gradually crystallized.

m.p.=131°-3° C.

$[a]_D^{20}$(c=10, methanol): -83°

The two methanol filtrates were combined and concentrated under reduced pressure to give 0.33 gm of a glass. The glass was treated as described above to give 0.121 gm of an oil which gradually crystallized.

m.p.=131°-4° C.

$[a]_D^{20}$(c=10, methanol): +78°

EXAMPLE 112

(R)-(+)-6-(t-butyloxycarbonyl)amino-2-(dimethyl) amino-1,2,3,4-tetrahydro-9H-carbazole Beginning with (R)-(+)-6-bromo-2-(dimethyl)amino-1,2,3,4-tetrahydro-9H-carbazole, the title compound was prepared by the procedure described in Preparation III.

$[a]_D^{20}$(c=10, methanol): +73°

EXAMPLE 113

(S)-(-)-6-(t-butyloxycarbonyl)amino-2-(dimethyl) amino-1,2,3,4-tetrahydro-9H-carbazole Beginning with (S)-(-)-6-bromo-2-(dimethyl)amino-1,2,3,4-tetrahydro-9H-carbazole, the title compound was prepared by the procedure described in Preparation III.

$[a]_D^{20}$(c=10, methanol): -72°

EXAMPLE 114

(R)-(+)-6-(4-fluorobenzoyl)amino-2-(dimethyl) amino-1,2,3,4-tetrahydro-9H-carbazole Beginning with (R)-(+)-6-bromo-2-(dimethyl)amino-1,2,3,4-tetrahydro-9H-carbazole, the title compound was prepared by the procedure described in Example 52.

$[a]_D^{20}$(c=10, methanol): +75°

EXAMPLE 115

(S)-(-)-6-(4-fluorobenzoyl)amino-2-(dimethyl) amino-1,2,3,4-tetrahydro-9H-carbazole Beginning with (S)-(-)-6-bromo-2-(dimethyl)amino-1,2,3,4-tetrahydro-9H-carbazole, the title compound was prepared by the procedure described in Example 52.

$[a]_D^{20}$(c=10, methanol): -70°

To demonstrate the use of the compounds of this invention in the treatment of migraine, their ability to bind to the 5-$HT_{1F}$ receptor subtype was determined. The ability of the compounds of this invention to bind to the 5-$HT_{1F}$ receptor subtype was measured essentially as described in N. Adham, et al., *Proceedings of the National Academy of Sciences (USA)*, 90, 408–412 (1993).

Membrane Preparation: Membranes were prepared from transfected Ltk- cells which were grown to 100% confluency. The cells were washed twice with phosphate-buffered saline, scraped from the culture dishes into 5 mL of ice-cold phosphate-buffered saline, and centrifuged at 200×g for 5 minutes at 4° C. The pellet was resuspended in 2.5 mL of ice-cold Tris buffer (20 mM Tris HCl, pH=7.4 at 23° C., 5 mM EDTA) and homogenized with a Wheaton tissue grinder. The lysate was subsequently centrifuged at 200×g for 5 minutes at 4° C. to pellet large fragments which were discarded. The supernatant was collected and centrifuged at 40,000×g for 20 minutes at 4° C. The pellet resulting from this centrifugation was washed once in ice-cold Tris wash buffer and resuspended in a final buffer containing 50 mM Tris HCl and 0.5 mM EDTA, pH=7.4 at 23° C. Membrane preparations were kept on ice and utilized within two hours for the radioligand binding assays. Protein concentrations were determined by the method of Bradford (*Anal. Biochem.*, 72, 248–254 (1976)).

Radioligand Binding: [$^3$H-5-HT] binding was performed using slight modifications of the 5-$HT_{1D}$ assay conditions reported by Herrick-Davis and Titeler (*J. Neurochem.*, 50, 1624–1631 (1988)) with the omission of masking ligands.

Radioligand binding studies were achieved at 37° C. in a total volume of 250 mL of buffer (50 mM Tris, 10 mM $MgCl_2$, 0.2 mM EDTA, 10 mM pargyline, 0.1% ascorbate, pH=7.4 at 37° C.) in 96 well microtiter plates. Saturation studies were conducted using [$^3$H]5-HT at 12 different concentrations ranging from 0.5 nM to 100 mM. Displacement studies were performed using 4.5–5.5 nM [$^3$H]5-HT. The binding profile of drugs in competition experiments was accomplished using 10–12 concentrations of compound. Incubation times were 30 minutes for both saturation and displacement studies based upon initial investigations which determined equilibrium binding conditions. Nonspecific binding was defined in the presence of 10 mM 5-HT. Binding was initiated by the addition of 50 mL membrane homogenates (10–20 µg). The reaction was terminated by rapid filtration through presoaked (0.5% poylethyleneimine) filters using 48R Cell Brandel Harvester (Gaithersburg, Md.). Subsequently, filters were washed for 5 seconds with ice cold buffer (50 mM Tris HCl, pH=7.4 at 4° C.), dried and placed into vials containing 2.5 mL Readi-Safe (Beckman, Fullerton, Calif.) and radioactivity was measured using a Beckman LS 5000TA liquid scintillation counter. The efficiency of counting of [$^3$H]5-HT averaged between 45–50%. Binding data was analyzed by computer-assisted nonlinear regression analysis (Accufit and Accucomp, Lunden Software, Chagrin Falls, Ohio). $IC_{50}$ values were converted to $K_i$ values using the Cheng-Prusoff equation (*Biochem. Pharmacol.*, 22, 3099–3108 (1973). All experiments were performed in triplicate. All of the compounds of the invention exemplified exhibited an $IC_{50}$ at the 5-$HT_{1F}$ receptor of at least 5 µmol.

As was reported by R. L. Weinshank, et al., WO93/14201, the 5-$HT_{1F}$ receptor is functionally coupled to a G-protein as measured by the ability of serotonin and serotonergic drugs to inhibit forskolin stimulated cAMP production in NIH3T3 cells transfected with the 5-$HT_{1F}$ receptor. Adenylate cyclase activity was determined using standard techniques. A maximal effect is achieved by serotonin. An $E_{max}$ is determined by dividing the inhibition of a test compound by the maximal effect and determining a percent inhibition. (N. Adham, et al., supra; R. L. Weinshank, et al., *Proceedings of the National Academy of Sciences (USA)*, 89,3630–3634 (1992)), and the references cited therein.

Measurement of cAMP formation

Transfected NIH3T3 cells (estimated Bmax from one point competition studies=488 fmol/mg of protein) were incubated in DMEM, 5 mM theophylline, 10 mM HEPES (4-[2-hydroxyethyl]-1-piperazineethanesulfonic acid) and 10 µm pargyline for 20 minutes at 37° C., 5% $CO_2$. Drug dose-effect curves were then conducted by adding 6 different final concentrations of drug, followed immediately by the addition of forskolin (10 mM). Subsequently, the cells were incubated for an additional 10 minutes at 37° C., 5% $CO_2$. The medium was aspirated and the reaction was stopped by the addition of 100 mM HCl. To demonstrate competitive antagonism, a dose-response curve for 5-HT was measured in parallel, using a fixed dose of methiothepin (0.32 mM). The plates were stored at 4° C. for 15 minutes and then centrifuged for 5 minutes at 500×g to pellet cellular debris, and the supernatant was aliquoted and stored at −20° C. before assessment of cAMP formation by radioimmunoassay (cAMP radioimmunoassay kit; Advanced Magnetics, Cambridge, Mass.). Radioactivity was quantified using a Packard COBRA Auto Gamma counter, equipped with data reduction software. All of the compounds exemplified were tested and found to be agonists at the 5-$HT_{1F}$ receptor in the cAMP assay.

The discovery that the pain associated with migraine and associated disorders is inhibited by agonists of the 5-$HT_{1F}$ receptor required the analysis of data from diverse assays of pharmacological activity. To establish that the 5-$HT_{1F}$ receptor subtype is responsible for mediating neurogenic meningeal extravasation which leads to the pain of migraine, the binding affinity of a panel of compounds to serotonin receptors was measured first, using standard procedures. For example, the ability of a compound to bind to the 5-$HT_{1F}$ receptor subtype was performed as described supra. For comparison purposes, the binding affinities of compounds to the 5-$HT_{1Da}$, 5-$HT_{1Db}$, 5-$HT_{1E}$ and 5-$HT_{1F}$ receptors were also determined as described supra, except that different cloned receptors were employed in place of the 5-$HT_{1F}$ receptor clone employed therein. The same panel was then tested in the cAMP assay to determine their agonist or antagonist character. Finally, the ability of these compounds to inhibit neuronal protein extravasation, a functional assay for migraine pain, was measured.

The panel of compounds used in this study represents distinct structural classes of compounds which were shown to exhibit a wide range of affinities for the serotonin receptors assayed. Additionally, the panel compounds were shown to have a wide efficacy range in the neuronal protein extravasation assay as well. The panel of compounds selected for this study are described below.

Compound I

3-[2-(dimethylamino)ethyl]-N-methyl-1H-indole-5-methanesulfonamide butane-1,4-dioate (1:1) (Sumatriptan succinate)

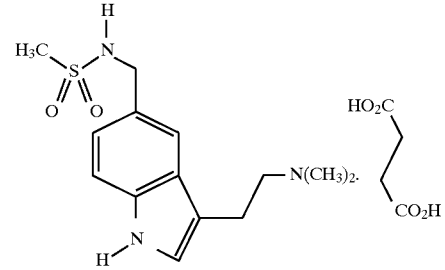

Sumatriptan succinate is commercially available as Imitrex™ or may be prepared as described in U.S. Pat. No. 5,037,845, issued Aug. 6, 1991, which is herein incorporated by reference.

Compound II 5-fluoro-3-<1-<2-<1-methyl-1H-pyrazol-4-yl>ethyl>-4-piperidinyl>-1H-indole hydrochloride

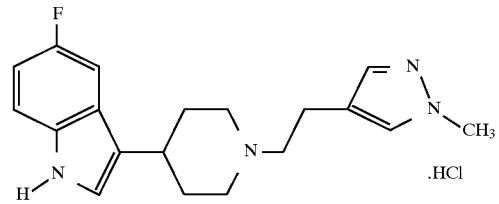

Compound II is available by the following procedure.
2-(1-methyl-3-pyrazolo)-1-ethanol To a mixture of 200 gm (2.85 mole) 2,3-dihydrofuran and 800 mL (4.81 mole) triethylorthoformate were added 0.8 mL (6.5 mMol) boron trifluoride diethyl etherate dropwise. After an initial exotherm the reaction mixture was allowed to stir at ambient temperature for four days. To the reaction mixture was then added 4.0 gm potassium carbonate and the reaction mixture was distilled under 6.0 mm Hg. Fractions distilling between 60° C. and 130° C. were collected to give 261.64 gm (42.1%) of a light yellow oil.

MS(m/e): 219($M^+$)

To a solution of 87.2 gm (0.40 mole) of the previously prepared yellow oil in 787 mL 1N HCl were added 21.3 mL (0.40 mole) methyl hydrazine and the reaction mixture was stirred at reflux for four hours. The reaction mixture was cooled to ambient temperature and the volatiles were removed under reduced pressure. The residual oil was treated with 2N NaOH until basic and the aqueous extracted well with dichloromethane. The combined organic extracts were dried over sodium sulfate and concentrated under reduced pressure to give 32.15 gm (64.5%) of the title compound as a brown oil.

MS(m/e): 126($M^+$)

$^1$H-NMR(DMSO-$d_6$): d7.45 (s, 1H); 7.25 (s, 1H); 4.65 (t, 1H); 3.75 (s,3H); 3.55 (m, 2H); 2.55 (t, 2H).

1-methyl-4-(2-methanesulfonyloxyethyl)pyrazole

To a solution of 16.0 gm (127 mMol) 2-(1-methyl-3-pyrazolo)-1-ethanol and 27 mL (193 mMol) triethylamine in 550 mL tetrahydrofuran were added 10.8 mL (140 mMol) methanesulfonyl chloride with icebath cooling. Once the addition was complete, the reaction mixture was stirred at ambient for 4 hours. The volatiles were then removed under reduced pressure and the residue partitioned between water and dichloromethane. The organic phase was washed with water followed by saturated aqueous sodium chloride and the remaining organics dried over sodium sulfate. The solvent was removed under reduced pressure to give a crude yield of 28.4 gm of the title compound as a brown oil. The product was used without further purification.

5-fluoro-3-[1,2,3,6-tetrahydro-4-pyridyl]-1H-indole

To a solution of 74 gm potassium hydroxide in 673 mL methanol were added 10.0 gm (74 mMol) 5-fluoroindole and 23.3 gm (151 mMol) 4-piperidone.HCl.H$_2$O. The reaction mixture was stirred at reflux for 18 hours. The reaction mixture was diluted with 1.3 L of water and the resulting precipitate recovered by filtration and dried under reduced pressure to give 10.75 gm (67.2%) of 5-fluoro-3-[1,2,5,6-tetrahydro-4-pyridyl]-1H-indole as a yellow solid.

5-fluoro-3-(4-piperidinyl)-1H-indole

To a solution of 10.75 gm (50 mMol) 5-fluoro-3-[1,2,5,6-tetrahydro-4-pyridyl]-1H-indole in 500 mL ethanol were added 2.0 gm 5% palladium on carbon and the reaction mixture hydrogenated at ambient temperature for 18 hours at an initial hydrogen pressure of 60 p.s.i. The reaction mixture was then filtered through a pad of celite and the filtrate concentrated under reduced pressure to give an off-white solid. The solid was recrystallized from methanol to give 8.31 gm (76.2%) of the title compound as a colorless solid.

m.p.=229°–230° C.

MS(m/e): 218($M^+$)

Calculated for $C_{13}H_{15}N_2F$: Theory: C, 71.53; H, 6.93; N, 12.83. Found: C, 71.81; H, 7.02; N, 12.80.

Alkylation

To a solution of 2.0 gm (9.2 mMol) 5-fluoro-3-(4-piperidinyl)-1H-indole and 2.4 gm (23 mMol) sodium carbonate in 50 mL dimethylformamide were added 1.87 gm (9.2 mMol) 1-methyl-4-(2-methanesulfonyloxyethyl) pyrazole in 5 mL dimethylformamide. The reaction mixture was stirred at 100° C. for 18 hours. The reaction mixture was cooled to ambient and the solvent removed under reduced pressure. The residue was partitioned between dichloromethane and water and the phases separated. The organic phase was washed well with water followed by saturated aqueous sodium chloride. The remaining organic phase was dried over sodium sulfate and concentrated under reduced pressure. The residual oil was subjected to silica gel chromatography, eluting with 20:1 dichloromethane:methanol. Fractions shown to contain the desired compound were combined and concentrated under reduced pressure to give a yellow oil. The oil was converted to the hydrochloride salt and was crystallized from ethyl acetate/methanol. 1.61 gm (51.1%) of Compound II were recovered as colorless crystals.

m.p.=239° C.

MS(m/e): 326($M^+$)

Calculated for $C_{19}H_{23}N_4F.HCl$: Theory: C, 62.89; H, 6.67; N, 15.44. Found: C, 62.80; H, 6.85; N, 15.40.

Compound III 5-hydroxy-3-(4-piperidinyl)-1H-indole oxalate

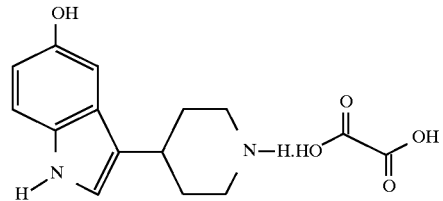

Compound III is available by the following procedure.

5-benzyloxy-3-[1,2,5,6-tetrahydro-4-pyridinyl]-1H-indole

Starting with 5.0 gm (22 mMol) 5-benzyloxyindole and 6.88 gm (45 mMol) 4-piperidone.HCl.H$_2$O, 6.53 gm (97.6%) of 5-benzyloxy-3-[1,2,5,6-tetrahydro-4-pyridinyl]-1H-indole were recovered as a light yellow solid by the procedure described in Preparation I. The material was used in the subsequent step without further purification.

Hydrogenation/Hydrogenolysis

To a solution of 1.23 gm (4 mMol) 5-benzyloxy-3-[1,2,5,6-tetrahydro-4-pyridinyl]-1H-indole in 50 mL 1:1 tetrahydrofuran:ethanol were added 0.3 gm 5% palladium on carbon and the reaction mixture hydrogenated at ambient temperature for 18 hours with an initial hydrogen pressure of 60 p.s.i. The reaction mixture was then filtered through a celite pad and the filtrate concentrated under reduced pressure. The residue was converted to the oxalate salt and 0.98 gm (80.0%) of Compound III were recovered as a brown foam.

m.p.=67° C.

MS(m/e): 216($M^+$)

Calculated for $C_{13}H_{16}N_2O.C_2H_2O_4$: Theory: C, 58.81; H, 5.92; N, 9.14. Found: C, 58.70; H, 5.95; N, 9.39.

Compound IV 8-chloro-2-diethylamino-1,2,3,4-tetrahydronaphthalene hydrochloride

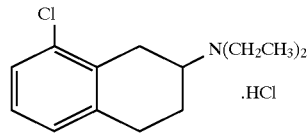

Compound IV is available by the following procedure.

8-chloro-2-tetralone

A mixture of 30.0 gm (0.176 mole) of o-chlorophenylacetic acid and 40.0 mL of thionyl chloride was stirred at ambient temperature for 18 hours. The volatiles were then removed in vacuo to give 32.76 gm (99.0%) of o-chlorophenylacetyl chloride as a transparent, pale yellow, mobile liquid.

NMR(CDCl$_3$): 7.5–7.1 (m, 4H), 4.2 (s, 2H).

To a slurry of 46.5 gm (0.348 mole) AlCl$_3$ in 400 mL dichloromethane at −78° C. was added a solution of 32.76 gm (0.174 mole) of the previously prepared o-chlorophenylacetyl chloride in 100 mL dichloromethane dropwise over 1 hour. The dry ice/acetone bath then was replaced with an ice/water bath and ethylene was bubbled into the reaction mixture during which time the temperature rose to 15° C. The ethylene addition was discontinued at the end of the exotherm and the reaction mixture was stirred at about 5° C. for 4 hours. Ice was then added to the reaction mixture to destroy aluminum complexes. Upon termination of the exotherm, the reaction mixture was diluted with 500 mL of water and stirred vigorously until all solids had dissolved. The phases were separated and the organic phase was washed with 3×400 mL 1N hydrochloric acid and 2×400 mL saturated aqueous sodium bicarbonate. The remaining organic phase was then dried over sodium sulfate and concentrated in vacuo to give a pale orange residue. The residue was dissolved in 1:1 hexane:diethyl ether and was poured over a flash silica column which was then eluted with 1:1 hexane:diethyl ether to give a light yellow residue which was crystallized from 4:1 hexane:diethyl ether to give 10.55 gm of the title compound.

NMR(CDCl$_3$): 7.5–7.2 (m, 3H), 3.7 (s, 2H), 3.3–3.0 (t, J=7 Hz, 2H), 2.8–2.4 (t, J=7 Hz, 2H).

MS: 180(60), 165(9), 138(100), 117(52), 115(50), 103 (48), 89(20), 76(25), 74(18), 63(30), 57(9), 52(28), 51(20), 42(6), 39(32).

IR(nujol mull): 2950 cm$^{-1}$, 2927 cm$^{-1}$, 1708 cm$^{-1}$, 1464 cm$^{-1}$, 1450 cm$^{-1}$, 1169 cm$^{-1}$, 1141 cm$^{-1}$.

Reductive Amination

To a solution of 0.5 gm (2.78 mMol) 8-chloro-2-tetralone in 25 mL cyclohexane were added 1.4 mL (13.9 mMol) diethylamine followed by 0.1 gm p-toluenesulfonic acid monohydrate. The reaction mixture was then heated at reflux with constant water removal (Dean-Stark Trap) for 18 hours. The reaction mixture was then cooled to ambient and the volatiles removed under reduced pressure. The residue was then dissolved in 15 mL methanol to which were then added 1.5 mL acetic acid followed by the portionwise addition of 0.5 gm sodium borohydride. The reaction mixture was then stirred for 1 hour at ambient.

The reaction mixture was then diluted with 20 mL 10% HCl and stirred for an additional hour. The mixture was then extracted with diethyl ether and the remaining aqueous phase was poured over ice, made basic with ammonium hydroxide and extracted well with dichloromethane. These extracts were combined, dried over sodium sulfate and concentrated under reduced pressure. The residue was redissolved in dichloromethane and subjected to chromatography over basic alumina, eluting with dichloromethane. Fractions shown to contain product were combined and concentrated under reduced pressure. The residual oil was dissolved in diethyl ether and the solution saturated with hydrogen chloride. The viscous residue was crystallized from acetone/diethyl ether to give 0.20 gm (23.2 %) of Compound IV as colorless crystals.

m.p.=158°–159° C.
MS(m/e): 273
Calculated for C$_{14}$H$_{21}$NCl.HCl: Theory: C, 61.32; H, 7.72; N, 5.11. Found: C, 61.62; H, 7.94; N, 5.03.

Compound V 6-hydroxy-3-dimethylamino-1,2,3,4-tetrahydrocarbazole

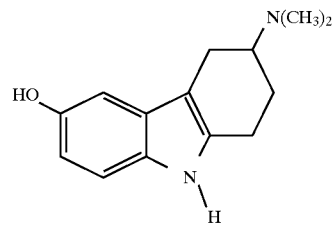

Compound V is available by the following procedure.
4-dimethylamino-1-cyclohexanone ethylene ketal To a solution of 5.0 gm (32 mMol) 1,4-cyclohexanedione mono-ethylene ketal and 10.80 gm (240 mMol) dimethylamine were added 2.0 mL acetic acid and the mixture was stirred at 0° C. for 1.5 hours. To this solution were then added 3.62 gm (58 mMol) sodium cyanoborohydride and the reaction stirred for an additional hour at ambient. The pH of the reaction mixture was adjusted to ~7 with 16 mL acetic acid and stirred 18 hours at ambient. The volatiles were removed under reduced pressure and the residue dissolved in cold 5% tartaric acid solution and then the aqueous phase was made basic with 5N sodium hydroxide. This aqueous phase was extracted well with dichloromethane. These organic extracts were combined and concentrated under reduced pressure to give 5.04 gm (85%) of the title compound as an oil.

4-dimethylamino-1-cyclohexanone 4.96 gm (26.8 mMol) 4-dimethylamino-1-cyclohexanone ethylene ketal were dissolved in 50 mL formic acid and the solution stirred at reflux for 18 hours. The reaction mixture was then cooled to ambient and the volatiles removed under reduced pressure to give 3.78 gm (100%) of the title compound.

6-benzyloxy-3-dimethylamino-1,2,3,4-tetrahydrocarbazole

To a solution of 3.78 gm (26.8 mMol) 4-dimethylamino-1-cyclohexanone and 6.69 gm (26.8 mMol) 4-benzyloxyphenylhydrazine hydrochloride in 50 mL ethanol were added 2.17 mL (26.8 mMol) pyridine. To this solution were added 5×10 mL portions of water and the reaction mixture then stored at 0° C. for 18 hours. The reaction mixture was then diluted with an additional 50 mL of water and the mixture extracted well with dichloromethane. The combined organic extracts were dried over sodium sulfate and the volatiles removed under reduced pressure. The residual oil was subjected to flash silica gel chromatography, eluting with 9:1 chloroform:methanol. Fractions shown to contain the desired product were combined and concentrated under reduced pressure to give 2.14 gm (24.9%) of the title compound.

Hydrogenolysis

To a solution of 2.14 gm (6.7 mMol) 6-benzyloxy-3-dimethylamino-1,2,3,4-tetrahydrocarbazole in 50 mL ethanol were added 0.20 gm 10% palladium on carbon and the reaction mixture was hydrogenated at ambient temperature with an initial hydrogen pressure of 40 p.s.i. After 5 hours an additional charge of 0.20 gm 10% palladium on carbon were added and the reaction mixture repressurized with hydrogen to 40 p.s.i. for 4 hours. The reaction mixture was then filtered through a pad of celite and the filtrate concentrated under reduced pressure. The residue was subjected to Florisil chromatography, eluting with 9:1 chloroform- :methanol. Fractions shown to contain the desired compound were combined and concentrated under reduced pressure. The residue was again subjected to Florisil chromatography, eluting with a gradient consisting of chloroform containing 2–10% methanol. Fractions shown to contain product were combined and concetnrated under reduced pressure to give Compound V as a crystalline solid.

MS(m/e): 230(M$^+$)

Calculated for $C_{14}H_{18}N_2O$: Theory: C, 73.01; H, 7.88; N, 12.16. Found: C, 72.75; H, 7.83; N, 11.97.

Binding Assays

The binding affinities of compounds for various serotonin receptors were determined essentially as described above except that different cloned receptors are employed in place of the 5-HT$_{1F}$ receptor clone employed therein. The results of these binding experiments are summarized in Table II.

TABLE II

BINDING TO SEROTONIN (5-HT$_1$) RECEPTOR SUBTYPES ($K_i$ nM)

| Compound | 5-HT$_{1Da}$ | 5-HT$_{1DB}$ | 5-HT$_{1E}$ | 5-HT$_{1F}$ |
|---|---|---|---|---|
| I | 4.8 | 9.6 | 2520.0 | 25.7 |
| II | 21.7 | 53.6 | 50.3 | 2.5 |
| III | 163.2 | 196.5 | 3.9 | 22.0 |
| IV | 13.5 | 145.3 | 813.0 | 129.2 |
| V | 791.0 | 1683.0 | 73.6 | 10.3 | cAMP Formation

All of the compounds of the panel were tested in the cAMP formation assay described supra and all were found to be agonists of the 5-HT$_{1F}$ receptor.

Protein Extravasation

Harlan Sprague-Dawley rats (225–325 g) or guinea pigs from Charles River Laboratories (225–325 g) were anesthetized with sodium pentobarbital intraperitoneally (65 mg/kg or 45 mg/kg respectively) and placed in a stereotaxic frame (David Kopf Instruments) with the incisor bar set at −3.5 mm for rats or −4.0 mm for guinea pigs. Following a midline sagital scalp incision, two pairs of bilateral holes were drilled through the skull (6 mm posteriorly, 2.0 and 4.0 mm laterally in rats; 4 mm posteriorly and 3.2 and 5.2 mm laterally in guinea pigs, all coordinates referenced to bregma). Pairs of stainless steel stimulating electrodes (Rhodes Medical Systems, Inc.) were lowered through the holes in both hemispheres to a depth of 9 mm (rats) or 10.5 mm (guinea pigs) from dura.

The femoral vein was exposed and a dose of the test compound was injected intravenously (1 mL/kg). Approximately 7 minutes later, a 50 mg/kg dose of Evans Blue, a fluorescent dye, was also injected intravenously. The Evans Blue complexed with proteins in the blood and functioned as a marker for protein extravasation. Exactly 10 minutes post-injection of the test compound, the left trigeminal ganglion was stimulated for 3 minutes at a current intensity of 1.0 mA (5 Hz, 4 msec duration) with a Model 273 potentiostat/galvanostat (EG&G Princeton Applied Research).

Fifteen minutes following stimulation, the animals were killed and exsanguinated with 20 mL of saline. The top of the skull was removed to facilitate the collection of the dural membranes. The membrane samples were removed from both hemispheres, rinsed with water, and spread flat on microscopic slides. Once dried, the tissues were coverslipped with a 70% glycerol/water solution.

A fluorescence microscope (Zeiss) equipped with a grating monochromator and a spectrophotometer was used to quantify the amount of Evans Blue dye in each sample. An excitation wavelength of approximately 535 nm was utilized and the emission intensity at 600 nm was determined. The microscope was equipped with a motorized stage and also interfaced with a personal computer. This facilitated the computer-controlled movement of the stage with fluorescence measurements at 25 points (500 μm steps) on each dural sample. The mean and standard deviation of the measurements was determined by the computer.

The extravasation induced by the electrical stimulation of the trigeminal ganglion was an ipsilateral effect (i.e. occurs only on the side of the dura in which the trigeminal ganglion was stimulated). This allows the other (unstimulated) half of the dura to be used as a control. The ratio of the amount of extravasation in the dura from the stimulated side compared to the unstimulated side dura was calculated. Saline controls yielded a ratio of approximately 2.0 in rats and 1.8 in guinea pigs. In contrast, a compound which effectively prevented the extravasation in the dura from the stimulated side would have a ratio of approximately 1.0. A dose-response curve was generated and the dose that inhibited the extravasation by 50% (ID$_{50}$) was approximated. This data is presented in Table III.

TABLE III

Inhibition of Protein Extravasation (ID$_{50}$ mMol/kg)

| Compound | i.v. ID$_{50}$ (mMol/kg) |
|---|---|
| I | $2.6 \times 10^{-8}$ |
| II | $8.6 \times 10^{-10}$ |
| III | $8.9 \times 10^{-9}$ |
| IV | $1.2 \times 10^{-7}$ |
| V | $8.7 \times 10^{-9}$ |

To determine the relationship of binding at various serotonin receptors to inhibition of neuronal protein extravasation, the binding affinity of all of the compounds to each of the 5-HT$_{1Da}$, 5-HT$_{1Db}$, 5-HT$_{1E}$ and 5-HT$_{1F}$ receptors was plotted against their ID$_{50}$ in the protein extravasation model. A linear regression analysis was performed on each set of data and a correlation factor, $R^2$, calculated. The results of this analysis are summarized in Table IV.

TABLE IV

Correlation Factor ($R^2$) for Specific 5-HT$_1$ Subtype Binding Affinity vs Inhibition of Protein Extravasation

| 5-HT$_1$ Subtype | Correlation Factor ($R^2$) |
|---|---|
| 5-HT$_{1Da}$ | 0.07 |
| 5-HT$_{1Db}$ | 0.001 |
| 5-HT$_{1E}$ | 0.31 |
| 5-HT$_{1F}$ | 0.94 |

An ideally linear relationship would generate a correlation factor of 1.0, indicating a cause and effect relationship between the two variables. The experimentally determined correlation factor between inhibition of neuronal protein extravasation and 5-HT$_{1F}$ binding affinity is 0.94. This nearly ideal dependence of the ID$_{50}$ in the protein extravasation model on binding affinity to the 5-HT$_{1F}$ receptor clearly demonstrates that the 5-HT$_{1F}$ receptor mediates the inhibition of protein extravasation resulting from stimulation of the trigeminal ganglia.

Sumatriptan exhibits low bioavailability and relatively short duration of action. Its affinity for a number of serotonin receptor subtypes gives rise to undesirable side effects, particularly vasoconstriction, which severely limits its utility in the treatment of migraine. The compounds of this invention, however, are highly bioavailable through several routes of administration including, but not limited to, oral, buccal, intravenous, subcutaneous and rectal. They exhibit a rapid onset and long duration of action, typically requiring only a single dose per day to maintain therapeutic levels. Since compounds of this invention are potent agonists of the 5-HT$_{1F}$ receptor, extremely low doses are required to maintain therapeutic levels. Additionally, due to the high selectivity of compounds of this invention for the 5-HT$_{1F}$ receptor, complications due to vasoconstriction are avoided. Compounds of this invention also inhibit protein extravasation if administered prior or subsequent to stimulation of the trigeminal ganglia, suggesting they may be administered prior to or during a migraine attack to alleviate pain.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See. e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Example 1

Hard gelatin capsules containing the following ingredients are prepared:

| Ingredient | Quantity (mg/capsule) |
| --- | --- |
| Compound of Example 24 | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Compound of Example 52 | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Compound of Example 102 | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
| --- | --- |
| Compound of Example 114 | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
| --- | --- |
| Compound of Example 103 | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
| --- | --- |
| Compound of Example 95 | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
| --- | --- |
| Compound of Example 77 | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament, are made as follows:

| Ingredient | Quantity (mg/capsule) |
| --- | --- |
| Compound of Example 83 | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9

An intravenous formulation may be prepared as follows:

| Ingredient | Quantity |
| --- | --- |
| Compound of Example 86 | 250.0 mg |
| Isotonic saline | 1000 ml |

Formulation Example 10

A topical formulation may be prepared as follows:

| Ingredient | Quantity |
|---|---|
| Compound of Example 87 | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

Sublingual or buccal tablets, each containing 10 mg of active ingredient, may be prepared as follows:

| Ingredient | Quantity Per Tablet |
|---|---|
| Compound of Example 72 | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50°–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

We claim:

1. A method for increasing activation of the 5-HT$_{1F}$ receptor in mammals comprising the administration to a mammal in need of such activation an effective dose of a compound of formula:

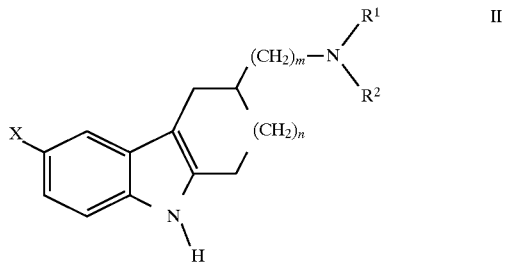

wherein:

R$^1$ and R$^2$ are independently hydrogen, C$_1$–C$_4$ alkyl, or —CH$_2$CH$_2$-Aryl where Aryl is phenyl, phenyl monosubstituted with halo, or 1-(C$_1$–C$_6$ alkyl)pyrazol-4-yl;

X is —NHC(O)R$^3$, —NHC(Y)NHR$^4$, —NHC(O)OR$^5$, or —NHSO$_2$R$^7$;

R$^3$ is C$_2$–C$_6$ alkenyl, C$_3$–C$_8$ cycloalkyl, phenyl, substituted phenyl, naphthyl, (C$_1$–C$_4$ alkylene) phenyl, thienylmethyl, or a heterocycle;

R$^4$ is C$_1$–C$_6$ alkyl, phenyl, or phenyl disubstituted with halo;

R$^5$ is C$_1$–C$_6$ alkyl, C$_2$–C$_6$ alkenyl, benzyl or phenyl monosubstituted with halo;

R$^6$ is C$_1$–C$_6$ alkyl, phenyl, or phenyl monosubstituted with halo or C$_1$–C$_4$ alkoxy;

R$^7$ is dimethylamino, phenyl or phenyl monosubstituted with halo or C$_1$–C$_4$ alkyl;

m is 0 or 1;

n is 1 or 2; and

Y is S or O; and pharmaceutically acceptable salts and hydrates thereof.

2. The method of claim 1 wherein the compound is R-(+)-6-(4-fluorobenzoyl)amino-3-(dimethyl)amino-1,2,3,4-tetrahydro-9H-carbazole, and pharmaceutically acceptable salts, solvates or hydrates thereof.

3. A pharmaceutical formulation for use in the activation of the 5-HT$_{1F}$ receptor comprising an effective dose of a compound of formula

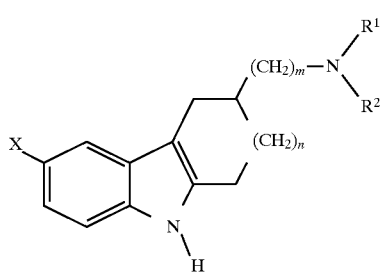

II wherein:
R¹ and R² are independently hydrogen, $C_1$–$C_4$ alkyl, or —$CH_2CH_2$-Aryl where Aryl is phenyl, phenyl monosubstituted with halo, or 1-($C_1$–$C_6$ alkyl)pyrazol-4-yl;

X is —NHC(O)R³, —NHC(Y)NHR⁴, —NHC(O)OR⁵, or —NHSO₂R⁷;

R³ is $C_2$–$C_6$ alkenyl, $C_3$–$C_8$ cycloalkyl, phenyl, substituted phenyl, naphthyl, ($C_1$–$C_4$ alkylene)-phenyl, thienylmethyl, or a heterocycle;

R⁴ is $C_1$–$C_6$ alkyl, phenyl, or phenyl disubstituted with halo;

R⁵ is $C_1$–$C_6$ alkyl, $C_2$–$C_6$ alkenyl, benzyl or phenyl monosubstituted with halo;

R⁶ is $C_1$–$C_6$ alkyl, phenyl, or phenyl monosubstituted with halo or $C_1$–$C_4$ alkoxy;

R⁷ is dimethylamino, phenyl or phenyl monosubstituted with halo or $C_1$–$C_4$ alkyl;

m is 0 or 1;

n is 1 or 2; and

Y is S or O; and pharmaceutically acceptable salts and hydrates thereof, together with at least one pharmaceutically acceptable carrier, diluent or excipient.

* * * * *